United States Patent
Geneste et al.

(10) Patent No.: US 9,163,019 B2
(45) Date of Patent: Oct. 20, 2015

(54) INHIBITOR COMPOUNDS OF PHOSPHODIESTERASE TYPE 10A

(71) Applicants: AbbVie Deutschland GmbH & Co. KG, Wiesbaden (DE); AbbVie Inc., North Chicago, IL (US)

(72) Inventors: Hervë Geneste, Ludwigshafen (DE); Michael Ochse, Ludwigshafen (DE); Karla Drescher, Ludwigshafen (DE); Berthold Behl, Ludwigshafen (DE); Loic Laplanche, Ludwigshafen (DE); Jürgen Dinges, North Chicago, IL (US); Clarissa Jakob, North Chicago, IL (US)

(73) Assignees: AbbVie Deutschland GmbH & Co. KG, Wiesbaden (DE); AbbVie Inc., North Chicago, IL (US)

( * ) Notice: Subject to any disclaimer, the term of this patent is extended or adjusted under 35 U.S.C. 154(b) by 0 days.

(21) Appl. No.: 14/208,067

(22) Filed: Mar. 13, 2014

(65) Prior Publication Data

US 2014/0303153 A1 Oct. 9, 2014

Related U.S. Application Data

(60) Provisional application No. 61/781,648, filed on Mar. 14, 2013.

(51) Int. Cl.
*A61K 31/54* (2006.01)
*C07D 471/02* (2006.01)
*C07D 471/04* (2006.01)
*C07D 519/00* (2006.01)

(52) U.S. Cl.
CPC ............ *C07D 471/04* (2013.01); *C07D 519/00* (2013.01)

(58) Field of Classification Search
None
See application file for complete search history.

(56) References Cited

U.S. PATENT DOCUMENTS

2007/0155779 A1  7/2007  Verhoest et al.

FOREIGN PATENT DOCUMENTS

| WO | 03/093499 | 11/2003 |
|---|---|---|
| WO | 2005/012485 | 2/2005 |
| WO | 2005/120514 | 12/2005 |
| WO | 2006/028957 | 3/2006 |
| WO | 2007/022280 | 2/2007 |
| WO | 2007/082546 | 7/2007 |
| WO | 2007/085954 | 8/2007 |
| WO | 2007/096743 | 8/2007 |
| WO | 2007/098169 | 8/2007 |
| WO | 2007/098214 | 8/2007 |
| WO | 2007/100880 | 9/2007 |
| WO | 2007/103370 | 9/2007 |
| WO | 2007/103554 | 9/2007 |
| WO | 2007/137819 | 12/2007 |
| WO | 2007/137820 | 12/2007 |
| WO | 2008/001182 | 1/2008 |
| WO | 2008/004117 | 1/2008 |
| WO | 2008/006372 | 1/2008 |
| WO | 2008/020302 | 2/2008 |
| WO | 2009/025823 | 2/2009 |
| WO | 2009/025839 | 2/2009 |
| WO | 2009/029214 | 3/2009 |
| WO | 2009/036766 | 3/2009 |
| WO | 2009/068246 | 6/2009 |
| WO | 2009/068320 | 6/2009 |
| WO | 2009/070583 | 6/2009 |
| WO | 2009/070584 | 6/2009 |
| WO | 2012/058133 | 5/2012 |
| WO | 2013/000994 | 1/2013 |

OTHER PUBLICATIONS

Silva, T. Mini Rev Med Chem 2005 vol. 5 pp. 893-914.*
Cantin, L-D. et al., "PDE-10A inhibitors as insulin secretagogues," Bioorg. Med. Chem. Lett. (2007) 17:2869-2873.
Chappie, T. et al., "PDE10A inhibitors: an assessment of the current CNS drug discovery landscape," Curr. Opin. in Drug Discovery & Development (2009) 12(4):438-467.
Diaz, G.J. et al., "The [3H]dofetilide binding assay is a predictive screening tool for hERG blockade and proarrhythmia: comparison of intact cell and membrane preparations and effects of altering [K+]o," J. Pharm. Toxicol. Meth. (2004) 50:187-199.

(Continued)

*Primary Examiner* — Heidi Reese
(74) *Attorney, Agent, or Firm* — Lisa V. Mueller; Michael Best & Friedrich LLP

(57) ABSTRACT

The present invention relates to compounds of the formula I, the N-oxides, tautomers, the prodrugs and the pharmaceutically acceptable salts thereof:

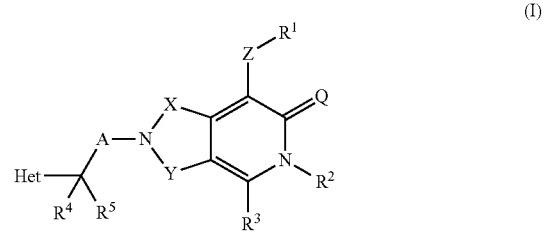

In formula I the variables Het, A, X, Y, Z, R1, R2, R3, R4, R5 and Q are as defined in the claims.
The compounds of the formula I, the N-oxides, tautomers, the prodrugs and the pharmaceutically acceptable salts thereof are inhibitors of phosphodiesterase type 10A. Thus, the invention also relates to the use of the compounds of the formula I, the N-oxides, tautomers, the prodrugs and the pharmaceutically acceptable salts thereof for the manufacture of a medicament and which thus are suitable for treating or controlling of medical disorders selected from neurological disorders and psychiatric disorders, for ameliorating the symptoms associated with such disorders and for reducing the risk of such disorders.

26 Claims, No Drawings

(56) References Cited

OTHER PUBLICATIONS

Francis, S.H. et al., "Mammalian cyclic nucleotide phosphodiesterases: molecular mechanisms and physiological functions," Physiol. Rev. (2011) 91:651-690.

Grauer, S.M. et al., "PDE10A inhibitor activity in preclinical models of the postive, cognitive and negative symptoms of schizophrenia," JPET Fast Forward (2006) 66 pages.

Nishi, A. et al., "Distinct roles of PDE4 and PDE10A in the regulation of cAMP/PKA signaling in the striatum," J. Neurosci. (2008) 28(42):10460-10471.

Rodefer, J.S. et al., "PDE10A inhibition reverses subchronic PCP-induced deficits in attentional set-shifting in rats," Eur. J. Neurosci. (2005) 21:1070-1076.

Schmidt, C.J. et al., "Preclinical characterization of selective phosphodiesterase 10A inhibitors: a new therapeutic approach to the treatment of schizophrenia," J. Pharm. Exp. Ther. (2008) 325(2):681-690.

Seeger, T.F. et al., "Immunohistochemical localization of PDE10A in the rat brain," Brain Res. (2003) 985:113-126.

Sotty, F. et al., "Phosphodiesterase 10A inhibition modulates the sensitivity of the mesolimbic dopaminergic system to D-amphetamine: involvement of the D1-regulated feedback control of midbrain dopamine neurons," J. Neurochem. (2009) 109:766-775.

* cited by examiner

INHIBITOR COMPOUNDS OF PHOSPHODIESTERASE TYPE 10A

CROSS-REFERENCE TO RELATED APPLICATIONS

This claims priority to U.S. Patent Application No. 61/781,648, filed on Mar. 14, 2013, the contents of which are fully incorporated herein by reference.

The present invention relates to compounds which are inhibitors of phosphodiesterase type 10A and to their use for the manufacture of a medicament and which thus are suitable for treating or controlling of medical disorders selected from neurological disorders and psychiatric disorders, for ameliorating the symptoms associated with such disorders and for reducing the risk of such disorders.

BACKGROUND OF THE INVENTION

Phosphodiesterase type 10A (hereinafter PDE10A) is a dual-substrate phosphodiesterase that can convert both cAMP to AMP and cGMP to GMP. PDE10A is highly prominent in the mammalian brain. In the rat, as well as in other mammalian species, PDE10A and the mRNA of PDE10A are highly enriched in the GABAergic medium spiny projection neurons (MSNs) of the striatal complex (caudate nucleus, nucleus accumbens, and olfactory tubercle) where the output is regulated by the effect of PDE10A on cAMP and cGMP signalling cascades (see e.g. C. J. Schmidt et al, The Journal of Pharmacology and Experimental Therapeutics 325 (2008) 681-690, A. Nishi, The Journal of Neuroscience 2008, 28, 10450-10471).

MSNs express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the substantia nigra and globus pallidus (Seeger, T. F. et al. Brain Research, 2003, 985, 1 13-126) Inhibition of PDE10A results in striatal activation and behavioral suppression such as dampened locomotion, inhibition of conditioned avoidance response (CAR), and activity in the rat auditory gating model, suggesting that inhibitors of phosphodiesterase type 10A represent a novel class of antipsychotic agents.

The hypotheses around the physiological role of PDE10A and the therapeutic utility of PDE10A inhibitors derive in part from studies with papaverine (J. A. Siuciak et al. loc. cit.), the first extensively profiled pharmacological tool compound for this target. The PDE10A inhibitor papaverine was shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine-induced hyperactivity was insignificant (WO 03/093499). These models suggest that PDE10A inhibition has the classic antipsychotic potential that would be expected from theoretical considerations. Papaverine, however has significant limitations in this regard with relatively poor potency and selectivity and a very short exposure half-life after systemic administration. It was found that inhibition of PDE10A reverses subchronic PCP-induced deficits in attentional set-shifting in rats suggesting that PDE10A inhibitors might alleviate cognitive deficits associated with schizophrenia. (Rodefer et al., Eur. J. Neurosci., 4 (2005) 1070-1076).

The discovery of a new class of PDE10A inhibitors with improved potency, selectivity, and pharmacokinetic properties, provided an opportunity to further explore the physiology of PDE10A and the potential therapeutic utility of inhibiting this enzyme. The new class of inhibitors are exemplified by MP-10 (PF-2545920: 2-{4-[1-methylpyridine-4-yl-1-H-pyrazol-3-3ly]phenoxymethyl}-quinoline) and TP-10, i.e. 2-{4-[pyridine-4-yl-1-(2,2,2-trifluoroethyl)-1-H-pyrazol-3-3ly]phenoxymethyl}-quinoline. The compounds offer a therapeutic approach to the treatment of schizophrenia (see C. J. Schmidt et al., loc cit.; S. M. Grauer et al., Journal of Pharmacology and Experimental Therapeutics, fast forward DOI 10.1124 JPET 109.155994). Positive signals in rodent models of schizophrenia include the: attenuation of conditioned avoidance response (CAR), inhibition of hyperactivity caused by amphetamine-induced dopamine release or phencyclidine (PCP) mediated NMDA receptor blockade, attenuation of pharmacologically impaired social or object recognition, and antagonism of apomorphine-induced climbing. Taken together, these data suggest a broad suppression of all 3 symptoms clusters (positive symptoms, negative symptoms & cognitive dysfunctions) linked to schizophrenia (see C. J. Schmidt et al., loc cit.; S. M. Grauer et al., loc. cit).

Beyond schizophrenia, selective PDE10 inhibitors may have the potential for the treatment of Huntington's disease (S. H. Francis et al., Physiol. Rev., 91 (2011) 651-690) and they may be an therapeutic option for substance abuse disorders (F. Sotty et al., J. Neurochem., 109 (2009) 766-775). Furthermore, it has been suggested that PDE10A inhibitors may be useful for treatment of obesity and non-insulin dependent diabetes (see e.g. WO 2005/120514, WO 2005/012485, Cantin et al, Bioorganic & Medicinal Chemistry Letters 17 (2007) 2869-2873).

In summary, inhibitors of PDE10A offer a promising therapeutic approach to the treatment or prevention of neurological and psychiatric disorders, in particular schizophrenia and related disorders, including symptoms linked to schizophrenia such as cognitive dysfunction.

Several classes of compounds which are inhibitors of PDE10A have been described in the art, the recent compound groups are:

Imidazo[1,5-a]pyrido[3,2-e]pyridazines and structurally related tricyclic Imidazo[1,5-a]pyridazines—see WO 2007/137819, WO 2007/137820, WO 2009/068246, WO 2009/068320, WO 2009/070583, WO 2009/070584, WO 010/054260 and WO 2011/008597;

4-substituted phthalazines and quinazolines WO 2007/085954, WO 2007/022280, WO 2007/096743, WO 2007/103370, WO 2008/020302, WO 2008/006372 and WO 2009/036766;

4-substituted cinnazolines—see WO 2006/028957, WO 2007/098169, WO 2007/098214, WO 2007/103554, WO 2009/025823 and WO 2009/025839;

Isoquinolines and isoquinolinones—see WO 2007/100880 and WO 2009/029214;

MP10 and MP10 like compounds: WO 2006/072828, WO 2008/001182 and WO 2008/004117; and Isoindolinones—see WO 2012/058133 and WO 2013/000994;

Pyrrolopyridin—5-ones—see WO 2013/000994;

Benzodiazepines—see WO 2007/082546.

For a further review see also T. Chappie et al. Current Opinion in Drug Discovery & Development 12(4), (2009) 458-467) and the literature cited therein as well as Jan Kehler, Phosphodiesterase 10A inhibitors: a 2009-2012 patent update, Expert Opin. Ther. Patents (2013) 23(1).

Although some of the compounds of prior art are known to inhibit PDE10A effectively having $IC_{50}$ values of less than 50 nM, there is still an ongoing need for compounds which inhibit PDE10A. In particular, there is an ongoing need for compounds which have one of the following characteristics:

i. Selective inhibition of PDE10A, in particular vis-à-vis inhibition of other phosphodiesterases such as PDE2, PDE3 or PDE4;

ii. metabolic stability, in particular microsomal stability, e.g. measured in vitro, in liver microsomes from various species (e.g. rat or human) in human cells, such as hepatocytes;

iii. no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

iv. a suitable solubility in water (in mg/ml);

v. suitable pharmacokinetics (time course of the concentration of the compound of the invention in plasma or in tissue, for example brain). The pharmacokinetics can be described by the following parameters: half-life, volume of distribution (in $l·kg^{-1}$), plasma clearance (in $l·h^{-1}·kg^{-1}$), AUC (area under the curve, area under the concentration-time curve (in $ng·h·l^{-1}$), oral bioavailability, (the dose-normalized ratio of AUC after oral administration and AUC after intravenous administration), the so-called brain-plasma ratio (the ratio of AUC in brain tissue and AUC in plasma);

vi. no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187-199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

vii. high free fraction in brain, i.e. the fraction of the compound bound to proteins should be low.

viii. low lipophilicity.

BRIEF DESCRIPTION OF THE INVENTION

The present invention is thus based on the object of providing compounds which inhibit PDE10A at low concentrations.

The compounds are further intended to display at least one of the properties i. to viii. mentioned above, in particular high selectivity with regard to inhibition of PDE10A, high selectivity vis-à-vis other phosphodiesterases such as, enhanced metabolic stability, in particular microsomal stability, cytosolic stability or hepatocyte stability, low affinity to the HERG receptor, low inhibition of cytochrome P450 (CYP) enzymes, suitable solubility in water and suitable pharmacokinetics.

This object and further objects are achieved by the compounds of the general formula I described below, the N-oxides, the prodrugs, the hydrates and the tautomers thereof and the pharmaceutically suitable salts thereof:

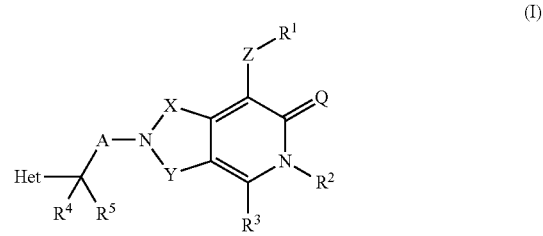

wherein

X is $CR^{x1}R^{x2}$ or $C(O)$, where $R^{x1}$ and $R^{x2}$, independently of each other are hydrogen, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, optionally substituted by 1, 2 or 3 methyl groups, and fluorinated $C_3$-$C_6$-cycloalkyl or the radicals $R^{x1}$ and $R^{x2}$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

Y is $CR^{y1}R^{y2}$ or $C(O)$, where $R^{y1}$ and $R^{y2}$, independently of each other are hydrogen, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, optionally substituted by 1, 2 or 3 methyl groups, and fluorinated $C_3$-$C_6$-cycloalkyl or the radicals $R^{y1}$ and $R^{y2}$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

provided that one or both of X and Y is/are C(O);
A is O, $[C(R^6,R^7)]_k$ with k=1 or 2, $OC(R^6,R^7)$, $C(R^8)=C(R^9)$ or $C\equiv C$;
Het is selected from the group consisting of
  i. monocyclic 5- or 6-membered hetaryl having 1 or 2 nitrogen atoms and optionally a further heteroatom selected from the group consisting of O, S and N as ring members, which is unsubstituted or may carry 1, 2, 3 or 4 identical or different substituents $R^a$,
  ii. fused 8-, 9- or 10-membered bicyclic hetaryl having one heteroatom selected from the group consisting of O, S and N and optionally 1, 2 or 3 nitrogen atoms as ring members, where the fused bicyclic hetaryl is unsubstituted or may carry 1, 2, 3 or 4 identical or different substituents $R^a$,
  iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^{aa}$, and where hetaryl is unsubstituted or carries 1, 2 or 3 radicals $R^a$;

$R^a$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, cyclopropyl substituted by 1, 2 or 3 methyl groups, fluorinated $C_3$-$C_6$-cycloalkyl, O—$C_3$-$C_6$-cycloalkyl, benzyloxy, C(O)O—($C_1$-$C_4$-alkyl), O—($C_1$-$C_4$-alkyl)-$CO_2$H, $C_1$-$C_4$ alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $NR^{13}R^{14}$, $C(O)NR^{13}R^{14}$, $C_1$-$C_4$-alkyl-$NR^{13}R^{14}$, —$NR^{15}$—C(O)—$NR^{13}R^{14}$, $NR^{15}$—C(O)O—($C_1$-$C_4$-alkyl), —$NR^{15}$—$SO_2$—$R^{12}$, CN, —$SF_5$, —$OSF_5$, —$SO_2R^{12}$, —$SR^{12}$ and trimethylsilyl, or two radicals $R^a$, which are bound to adjacent ring atoms may also form linear $C_3$-$C_5$-alkanediyl, wherein 1 or 2 $CH_2$ moieties can be replaced by C=O, O, S, S(=O), $S(=O)_2$ or NR', and where alkanediyl is unsubstituted or may carry 1 or 2 radicals selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy;

$R^{aa}$ has one of the meanings given for $R^a$ or one radical $R^{aa}$ may also be phenyl or a 5- or 6-membered hetaryl having 1 or 2 nitrogen atoms and optionally a further heteroatom selected from the group consisting of O, S and N as ring members, where phenyl and hetaryl are unsubstituted or may carry 1, 2 or 3 radicals selected from the group consisting of halogen, OH, $C_1$-$C_4$-alkyl, $C_1$-$C_4$ haloalkyl $C_1$-$C_4$-alkoxy and $C_1$-$C_4$-haloalkoxy;

Q is O or S;
Z is selected from the group consisting of a chemical bond, $CH_2$, O, O—$CH_2$, C(O)O, C(O), $NR^z$, $NR^z$—$CH_2$, $S(O)_2$—$NR^z$, C(O)—$NR^z$, S, S(O), $S(O)_2$, C(O)—O—$CH_2$, C(O)—$NR^z$—$CH_2$, 1,2-ethanediyl, 1,2-ethenediyl and 1,2-ethynediyl, where $R^z$ is selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;

$R^1$ is selected from the group consisting of phenyl, naphthyl, $C_3$-$C_8$-cycloalkyl, 3- to 8-membered saturated or partially unsaturated heteromonocyclic radicals, saturated or partially unsaturated 7- to 10-membered heterobicyclic radicals, 5- or 6-membered monocyclic hetaryl, and 8- to 10-membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_8$-cycloalkyl, the saturated or partially unsaturated heteromonocyclic and heterobicyclic radicals are unsubstituted or carry 1, 2, 3, 4 or 5 radicals $R^{C1}$ or one radical Y'—$R^{C2}$ and 0, 1, 2, 3 or 4 radicals $R^{C1}$;

where phenyl, naphthyl, the mono and bicyclic heteroaromatic radicals are unsubstituted or carry 1, 2, 3, 4 or 5 radicals $R^{C3}$ or one radical Y'—$R^{C2}$ and 0, 1, 2, 3 or 4 radicals $R^{c3}$; where $R^{C1}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^h$, Z'—$C(O)OR^b$, Z'—$C(O)NR^cR^d$, $NR^gSO_2R^h$, $S(O)_2NR^cR^d$ and Z'—$NR^eR^f$, where $R^b$, $R^g$ independently of each other are selected from the group consisting of hydrogen, $C_1$-$C_4$-alkyl, $C_2$-$C_4$-alkenyl and $C_1$-$C_4$-fluoroalkyl, $R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ independently of each other are selected from the group consisting of hydrogen, $C_1$-$C_4$-alkyl, $C_1$-$C_4$-fluoroalkyl, $C_1$-$C_4$-hydroxyalkyl, $C_1$-$C_4$-alkoxy-$C_1$-$C_4$-alkyl, $C_1$-$C_4$-alkoxy and $C_1$-$C_4$-fluoroalkoxy, $R^h$ is selected from the group consisting of $C_1$-$C_4$-alkyl and $C_1$-$C_4$-fluoroalkyl, Z' is a covalent bond or $C_1$-$C_4$-alkanediyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N, or two radicals $R^{C1}$ which are bound at the same carbon atom may form an oxygen atom, where the fused and the spiro radicals are unsubstituted or carry 1, 2, 3 or 4 radicals $R^{c4}$;

Y' is a chemical bond, $CH_2$, O, O—$CH_2$, C(O), $S(O)_2$, $NR^{3'}$, $NR^{3'}$-$CH_2$ or $NR^{3'}$-$S(O)_2$, where $R^{3'}$ is selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;

$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{C4}$;

$R^{C3}$ is selected from the group consisting of halogen, OH, CN, NO$_2$, C$_1$-C$_4$-alkyl, C$_1$-C$_4$-alkoxy, C$_1$-C$_4$-alkylsulfanyl, hydroxy-C$_1$-C$_4$-alkyl, C$_1$-C$_4$-alkoxy-C$_1$-C$_4$-alkyl, C$_1$-C$_4$-alkoxy-C$_1$-C$_4$-alkoxy, cyano-C$_1$-C$_4$-alkyl, C$_1$-C$_4$-fluoroalkyl, C$_1$-C$_4$-fluoroalkoxy, C$_1$-C$_4$-alkylsulfonyl, C(O)R$^h$, Z'—C(O)OR$^b$, Z'—C(O)NR$^c$R$^d$, NR$^g$SO$_2$R$^h$, S(O)$_2$NR$^c$R$^d$ and Z'—NR$^e$R$^f$, wherein Z', R$^b$, R$^c$, R$^d$, R$^e$ and R$^f$ and R$^h$ are as defined above,
or two radicals $R^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{C4}$;

$R^{C4}$ is selected from the group consisting of halogen, OH, CN, C$_1$-C$_4$-alkyl, C$_1$-C$_4$-alkoxy, hydroxy-C$_1$-C$_4$-alkyl, C$_1$-C$_4$-alkoxy-C$_1$-C$_4$-alkyl, cyano-C$_1$-C$_4$-alkyl, C$_1$-C$_4$-fluoroalkyl, C$_1$-C$_4$-fluoroalkoxy, C$_2$-C$_6$-alkenyl, C(O)R$^h$, benzyl, Z'—C(O)OR$^b$, Z'—C(O)NR$^c$R$^d$, S(O)$_2$NR$^c$R$^d$ and Z'—NR$^e$R$^f$, where, Z', R$^b$, R$^c$, R$^d$, R$^e$ and R$^f$ and R$^h$ are as defined above or two radicals $R^{C4}$ which are bound at the same atom may form an oxygen atom;

$R^2$ is selected from the group consisting of hydrogen, C$_1$-C$_6$-alkyl, C$_2$-C$_6$-alkenyl, C$_2$-C$_6$-alkynyl, C$_1$-C$_4$-alkyl-CN, C$_1$-C$_4$-alkyl-OR$^{21}$, C$_1$-C$_4$-alkyl-SR$^{22}$, C$_1$-C$_4$-alkyl-NR$^{23}$R$^{24}$, C$_1$-C$_6$-fluoroalkyl, C$_3$-C$_6$-cycloalkyl, C$_3$-C$_6$-cycloalkyl-C$_1$-C$_4$-alkyl, where the cycloalkyl moiety in the last two radicals is unsubstituted, partially or completely fluorinated, or substituted by 1, 2 or 3 methyl groups,
phenyl, phenyl-C$_1$-C$_4$-alkyl, 5- or 6-membered hetaryl and 5- or 6-membered hetaryl-C$_1$-C$_4$-alkyl, where hetaryl has 1 heteroatom selected from the group consisting of O, S and N as ring member and 0, 1 or 2 further N atoms as ring members, and wherein phenyl and hetaryl in the last four mentioned radicals are unsubstituted or carry 1 or 2 radicals selected from the group consisting of halogen, OH, CN, C$_1$-C$_4$-alkyl, C$_1$-C$_4$-alkoxy, hydroxy-C$_1$-C$_4$-alkyl, C$_1$-C$_4$-alkoxy-C$_1$-C$_4$-alkyl, cyano-C$_1$-C$_4$-alkyl, C$_1$-C$_4$-fluoroalkyl, C$_1$-C$_4$-fluoroalkoxy, C$_2$-C$_6$-alkenyl, C(O)R$^h$, benzyl, Z'—C(O)OR$^b$, Z'—C(O)NR$^c$R$^d$, S(O)$_2$NR$^c$R$^d$ and Z'—NR$^e$R$^f$, where Z', R$^b$, R$^c$, R$^d$, R$^e$, R$^f$ and R$^h$ are as defined above;

$R^3$ is selected from the group consisting of hydrogen, halogen, C$_1$-C$_4$-alkyl, C$_1$-C$_4$-alkoxy, C$_1$-C$_4$-fluoroalkyl, C$_1$-C$_4$-fluoroalkoxy, C$_3$-C$_6$-cycloalkyl, cyclopropyl substituted by 1, 2 or 3 methyl groups, fluorinated cyclopropyl, OH, hydroxy-C$_1$-C$_4$-alkyl, O—C$_3$-C$_6$-cycloalkyl, benzyloxy, C(O)O—(C$_1$-C$_4$-alkyl), O—(C$_1$-C$_4$-alkyl)-CO$_2$H, C$_1$-C$_4$-alkyl-OR$^{31}$, C$_1$-C$_4$-alkyl-SR$^{32}$, C$_1$-C$_4$-alkyl-NR$^{33}$R$^{34}$, OC$_1$-C$_4$-alkyl-OR$^{11}$, OC$_1$-C$_4$-alkyl-SR$^{32}$, OC$_1$-C$_4$-alkyl-NR$^{33}$R$^{34}$, NR$^{33}$R$^{34}$, C(O)NR$^{33}$R$^{34}$, C$_1$-C$_4$-alkyl-NR$^{33}$R$^{34}$, —NR$^{35}$—C(O)—NR$^{33}$R$^{34}$, NR$^{35}$—C(O)O—(C$_1$-C$_4$-alkyl), —NR$^{35}$—SO$_2$—R$^{32}$, phenyl, CN, —SF$_5$, —OSF$_5$, —SO$_2$R$^{32}$, —SR$^{32}$ and trimethylsilyl;

$R^4$, $R^5$ independently of each other are selected from the group consisting of hydrogen, halogen, C$_1$-C$_4$-alkyl, trimethylsilyl, C$_1$-C$_4$-fluoroalkyl, C$_1$-C$_4$-alkoxy, C$_1$-C$_4$-fluoroalkoxy, C$_3$-C$_6$-cycloalkyl, or the radicals $R^4$, $R^5$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

$R^6$, $R^7$ independently of each other are selected from the group consisting of hydrogen, halogen, C$_1$-C$_4$-alkyl, trimethylsilyl, C$_1$-C$_4$-fluoroalkyl, C$_1$-C$_4$-alkoxy, C$_1$-C$_4$-fluoroalkoxy, C$_3$-C$_6$-cycloalkyl, or the radicals $R^6$, $R^7$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

$R^8$, $R^9$ independently of each other are selected from the group consisting of hydrogen, halogen, C$_1$-C$_4$-alkyl and C$_1$-C$_4$-fluoroalkyl,
the moiety C(R$^4$,R$^5$)-A may also form a moiety C(R$^8$)=C(R$^9$), C≡C, C(R$^8$)=C(R$^9$)—C(R$^6$,R$^7$) or C≡C—C(R$^6$,R$^7$),
the moiety C(R$^4$,R$^5$)-A may also form a cyclopropane-1,2-diyl or cyclopropane-1,2-diyl-C(R$^6$,R$^7$), where the cyclopropane-1,2-diyl moiety is unsubstituted or carries 1 or 2 radicals selected from the group consisting of halogen, C$_1$-C$_4$-alkyl, trimethylsilyl, C$_1$-C$_4$-fluoroalkyl, C$_1$-C$_4$-alkoxy and C$_1$-C$_4$-fluoroalkoxy;

and where
$R^{11}$, $R^{12}$, $R^{21}$, $R^{22}$, $R^{31}$ and $R^{32}$ independently of each other are selected from the group consisting of hydrogen, C$_1$-C$_4$-alkyl, C$_1$-C$_4$-fluoroalkyl, C$_3$-C$_6$-cycloalkyl, C$_3$-C$_6$-cycloalkyl-C$_1$-C$_4$-alkyl, where $R^{11}$ may also be C$_1$-C$_4$-alkylsulfonyl and C$_1$-C$_4$-fluoroalkylsulfonyl;

$R^{13}$, $R^{14}$ independently of each other are selected from the group consisting of hydrogen, C$_1$-C$_4$-alkyl, C$_1$-C$_4$-fluoroalkyl, C$_3$-C$_6$-cycloalkyl and C$_3$-C$_6$-cycloalkyl-C$_1$-C$_4$-alkyl, or
$R^{13}$ and $R^{14}$ together with the N atom to which they are attached form a 3- to 7-membered, nitrogen heterocycle which may have 1, 2 or 3 further different or identical heteroatoms or heteroatom containing groups selected from the group consisting of O, N, S, SO and SO$_2$ as ring members and which may carry 1, 2, 3, 4, 5 or 6 C$_1$-C$_4$-alkyl substituents;

$R^{23}$, $R^{24}$, $R^{33}$ and $R^{34}$ have one of the meanings given for $R^{13}$, $R^{14}$;

$R^{15}$, $R^{35}$ independently of each other are selected from the group consisting hydrogen, C$_1$-C$_4$-alkyl, C$_1$-C$_4$-fluoroalkyl, C$_3$-C$_6$-cycloalkyl and C$_3$-C$_6$-cycloalkyl-C$_1$-C$_4$-alkyl; and R' is hydrogen, hydrogen, C$_1$-C$_4$-alkyl, C$_1$-C$_4$-fluoroalkyl, C$_3$-C$_6$-cycloalkyl or C$_3$-C$_6$-cycloalkyl-C$_1$-C$_4$-alkyl.

The present invention therefore relates to the compounds of the general formula I, the N-oxides, the tautomers, and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I. The present invention in particular relates to the compounds of the general formula I and to their pharmaceutically acceptable salts.

The present invention also relates to the compounds of the general formula I, the N-oxides, the tautomers and the hydrates thereof, the pharmaceutically acceptable salts of the compounds of formula I, the prodrugs of the compounds of formula I and the pharmaceutically acceptable salts of said N-oxides, prodrugs, tautomers or hydrates of the compounds of formula I for the use in the treatment of a medical disorder, selected from neurological and psychiatric disorders which can be treated by modulation of phosphodiesterase type 10.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates effectively inhibit PDE10A even at low concentrations. They are additionally distinguished by a high selectivity in relation to the inhibition of the PDE10A vis-à-vis inhibition of other phosphodiesterase, such as PDE2, PDE3 or PDE4. The compounds of the invention may additionally have one or more of the above mentioned properties ii. to viii.

The compounds of the formula I, their pharmaceutically acceptable salts, their N-oxides, their prodrugs, their hydrates and their tautomers and the pharmaceutically acceptable salts of said N-oxides, prodrugs, tautomers or hydrates are therefore particularly suitable for treating disorders and conditions in creatures, especially human creatures, which can be treated or controlled by inhibition of phosphodiesterase type 10A.

The invention therefore also relates to the use of the compounds of the formula I, their N-oxides, their tautomers, their hydrates and their pharmaceutically acceptable salts and the pharmaceutically acceptable salts of said N-oxides, prodrugs, tautomers or hydrates for the manufacture of a medicament, in particular of a medicament which is suitable for the treatment of a disorder or a condition which can be treated by inhibition of phosphodiesterase type 10A.

The invention further relates to a medicament, in particular a medicament which is suitable for the treatment of a disorder or a condition which can be treated by inhibition of phosphodiesterase type 10A. The medicament comprises at least one compound of the formula I, as described herein, or an N-oxide, a tautomer, or a hydrate or a prodrug of said compound I, or a pharmaceutically acceptable salt of the compound of the formula I or a pharmaceutically acceptable salt of the N-oxide, the tautomer, the hydrate or the prodrug of compound of the formula I.

DETAILED DESCRIPTION OF THE INVENTION

The terms "compound of the formula I" and "compounds I" are used as synonyms.

The term "prodrugs" means compounds which are metabolized in vivo to the compounds I of the invention. Typical examples of prodrugs are described in C. G. Wermuth (editor): The Practice of Medicinal Chemistry, Academic Press, San Diego, 1996, pages 671-715. These include for example phosphates, carbamates, amino acids, esters, amides, peptides, ureas and the like. Suitable prodrugs in the present case may be for example derivatives of those compounds I carrying an OH or $NH_2$-group, where the OH or $NH_2$-group forms an ester/amide/peptide linkage, i.e. where one of the hydrogen atoms of the OH or $NH_2$-group is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an acyl group derived from an amino acid, e.g. glycine, alanine, serine, phenylalanine and the like, which is linked to the oxygen or nitrogen of the OH or $NH_2$-group via the carbonyl group of the amino acid. Further suitable prodrugs are alkylcarbonyloxyalkyl carbonates or carbamates of compounds I carrying an OH— or $NH_2$-group in which one of the hydrogen atoms of the OH— or $NH_2$-group has been replaced by a group of the formula —C(=O)—O—CHR$^p$—O—C(=O)—R$^q$ in which R$^p$ and R$^q$ are independently of one another $C_1$-$C_4$-alkyl. Such carbonates and carbamates are described for example in J. Alexander, R. Cargill, S. R. Michelson, H. Schwam, J. Medicinal Chem. 1988, 31(2), 318-322. These groups can then be eliminated under metabolic conditions and result in compounds I. Therefore, said prodrugs and their pharmaceutically acceptable salts are also part of the invention.

The term "pharmaceutically acceptable salts" refers to cationic or anionic salts compounds, wherein the counter ion is derived from pharmaceutically acceptable non-toxic bases or acids including inorganic or organic bases and inorganic or organic acids.

When the compound of formula I or its prodrug, tautomer, hydrate or N-oxide is acidic, salts may be prepared from pharmaceutically acceptable non-toxic bases, including inorganic and organic bases. Salts derived from inorganic bases include salts, wherein the counter ion is aluminium, ammonium, calcium, copper, ferric, ferrous, lithium, magnesium, manganic, manganous, potassium, sodium, zinc ion and the like. Particularly preferred are the ammonium, calcium, magnesium, potassium, and sodium ions. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of formula I or its prodrug, tautomer, hydrate or N-oxide is basic, salts may be prepared from pharmaceutically acceptable non-toxic acids, including inorganic and organic acids. Such acids include acetic, trifluoroacetic acid, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of formula I are meant to also include the pharmaceutically acceptable salts.

The compounds of the invention may be in the form of a mixture of diastereomers, or of a mixture of diastereomers in which one of the two diastereomers is enriched, or of essentially diastereomerically pure compounds (diastereomeric excess de>90%). The compounds are preferably in the form of essentially diastereomerically pure compounds (diastereomeric excess de>90%). The compounds I of the invention may furthermore be in the form of a mixture of enantiomers (for example as racemate), of a mixture of enantiomers in which one of the two enantiomers is enriched, or essentially in enantiomerically pure compounds (enantiomeric excess ee>90%). It is preferred to employ the compounds enantiomerically pure or diastereomerically pure.

The present invention moreover relates to compounds as defined herein, wherein one or more of the atoms depicted in formula I have been replaced by a stable isotope (e.g., hydrogen by deuterium, $^{12}C$ by $^{13}C$, $^{14}N$ by $^{15}N$, $^{16}O$ by $^{18}O$) or by an instable, i.e. radioactive isotope (e.g. $^{12}C$ by $^{11}C$, $^{16}O$ by $^{15}O$, $^{19}F$ by $^{18}F$), preferably by a stable isotope, or enriched with regard to said isotope beyond the natural level. Of course, the compounds according to the invention contain more of the respective isotope than this naturally occurs and thus is anyway present in the compounds I.

The compounds of the formula I and their salts in the solid form may exist in more than one crystal structure (polymorphism), and may also be in the form of hydrates or other solvates. The present invention includes any polymorph of the compound I or its salt as well as any hydrate or other solvate.

In the context of the present description, unless stated otherwise, the terms "alkyl", "alkenyl", "alkynyl", "alkoxy", "fluorooalkyl", "fluoroalkoxy", "cycloalkyl", "fluorinated cycloalkyl", "alkanediyl", "heterocyclyl", "hetaryl", "aryl" and radicals derived therefrom, such as "hydroxylalkyl", "alkoxylalkyl", "alkoxyalkoxy", "alkylsulfanyl", "alkylsulfonyl", "fluorinated alkylsulfanyl", "fluorinated alkylsulfonyl", "cycloalkylalkyl", represent groups of individual radicals. The groups of noncyclic radicals "alkyl", "alkenyl", "alkynyl", "alkoxy", "fluoroalkyl", "fluoroalkoxy", "alkylene", "alkanediyl", and the groups of radicals derived therefrom always include both unbranched and branched "alkyl", "alkenyl", "alkynyl", "alkoxy", "fluoroalkyl", "fluoroalkoxy", "alkylene" and "alkanediyl", respectively.

The prefix $C_n$-$C_m$— indicates the respective number of carbons in the hydrocarbon unit. Unless indicated otherwise, fluorinated substituents preferably have one to five identical or different fluorine atoms.

The term "halogen" designates in each case, fluorine, bromine, chlorine or iodine, specifically fluorine, chlorine or bromine The term "partially or completely fluorinated" indicates that at least on, e.g. 1, 2, 3, 4, 5 or 6 of the hydrogen atoms or all of the hydrogen atoms of the respective moiety are replaced by halogen atoms, in particular by fluorine atoms Examples of other meanings are:

Alkyl, and the alkyl moieties for example in alkoxy, alkoxyalkyl, alkoxyalkoxy, alkylsulfanyl, alkylsulfonyl: saturated, straight-chain or branched hydrocarbon radicals having one or more C atoms, e.g. 1 to 6 or 1 to 4 carbon atoms. Examples of $C_1$-$C_4$-alkyl are methyl, ethyl, propyl, 1-methylethyl, n-butyl, 1-methylpropyl, 2-methylpropyl and 1,1-dimethylethyl. $C_1$-$C_6$-alkyl are, apart those mentioned for $C_1$-$C_4$-alkyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Fluoroalkyl and the fluoroalkyl moieties for example in fluoroalkyl, fluorinated alkylsulfanyl and fluorinated alkylsulfonyl: an alkyl radical having ordinarily 1 to 6 C atoms, frequently 1 to 4 C atoms, in particular 1 or 2 C-atoms ($C_1$-$C_2$-fluoralkyl) as mentioned above, whose hydrogen atoms are partly or completely replaced by fluorine atoms such as fluoromethyl, difluoromethyl, trifluoromethyl, 2-fluoroethyl, 2,2-difluoroethyl, 2,2,2-trifluoroethyl, pentafluoroethyl, 2-fluoro-1-methylethyl, 2,2-difluoro-1-methylethyl, 2,2-trifluoro-1-methylethyl, 2-fluoropropyl, 3-fluoropropyl, 2,2-difluoropropyl, 2,3-difluoropropyl, 3,3,3-trifluoropropyl, 2,3,3,3-pentafluoropropyl, heptafluoropropyl, 1-(fluoromethyl)-2-fluoroethyl, 4-fluorobutyl, and nonafluorobutyl.

Cycloalkyl, and the cycloalkyl moieties for example in cycloalkoxy, cycloalkyl-$C_1$-$C_4$-alkyl or cycloalkyl-$C_1$-$C_4$-alkoxy: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl.

Fluorinated cycloalkyl, and the fluorinated cycloalkyl moieties for example in fluorinated cycloalkoxy or fluorinated cycloalkyl-$C_1$-$C_4$-alkyl: monocyclic, saturated hydrocarbon groups having three or more C atoms, e.g. 3, 4, 5, 6, 7 or 8 carbon ring members, such as cyclopropyl, cyclobutyl, cyclopentyl, cyclohexyl and cycloheptyl, wherein at least one, e.g. 1, 2, 3, 4, 5 or 6 or all of the hydrogen atoms are replaced by fluorine atoms, examples including 1-fluorocyclopropyl, 2-fluorocyclopropyl, 2,2-difluorocyclopropyl, 1,2-difluorocyclopropyl, 2,3-difluorocyclopropyl, etc.

Cycloalkylalkyl: a cycloalkyl radical as defined above which is linked via an alkylene group, in particular via a methylene, 1,1-ethylene or 1,2-ethylene group, e.g. cyclopropylmethyl, cyclobutylmethyl, cyclopentylmethyl, cyclohexylmethyl, 1-cyclopropylethyl, 1-cyclobutylethyl, 1-cyclopentylethyl, 1-cyclohexylethyl, 2-cyclopropylethyl, 2-cyclobutylethyl, 2-cyclopentylethyl or 2-cyclohexylethyl.

Fluorinated cycloalkylalkyl: a halogenated, in particular a fluorinated cycloalkyl radical as defined above which is linked via an alkylene group, in particular via a methylene, 1,1-ethylene or 1,2-ethylene group, e.g. 1-fluorocyclopropylmethyl, 2-fluorocyclopropylmethyl, 2,2-difluorocyclopropylmethyl, 1,2-difluorocyclopropylmethyl, 2,3-difluorocyclopropylmethyl, 1-(1-fluorocyclopropyl)ethyl, 1-(2-fluorocyclopropyl)ethyl, 1-(2,2-difluorocyclopropyl)ethyl, 1-(1,2-difluorocyclopropyl)ethyl, 1-(2,3-difluorocyclopropyl)ethyl, 2-(1-fluorocyclopropyl)ethyl, 2-(2-fluorocyclopropyl)ethyl, 2-(2,2-difluorocyclopropyl)ethyl, 2-(1,2-difluorocyclopropyl)ethyl or 2-(2,3-difluorocyclopropyl)ethyl.

Alkenyl: monounsaturated, straight-chain or branched hydrocarbon radicals having two or more C atoms, e.g. 2 to 8, especially 2 to 4 carbon atoms and one C=C-double bond in any position, e.g. $C_2$-$C_4$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl.

Alkynyl: monounsaturated, straight-chain or branched hydrocarbon radicals having two or more C atoms, e.g., e.g. 2 to 8, especially 2 to 6 carbon atoms and one C≡C-triple bond in any position, e.g. $C_2$-$C_4$-alkenyl such as ethynyl, 1-propynyl, 2-propynyl, 1-butynyl, 2-butynyl, 3-butynyl, 1-methyl-2-propynyl, 1-methyl-2-butynyl and 2-methyl-3-butynyl.

Alkoxy or alkoxy moieties for example in alkoxyalkyl and alkoxyalkoxy:

an alkyl radical as defined above having normally 1 to 6 C atoms, in particular 1 to 4 C atoms, which is connected to the remainder of the molecule via an O atom: e.g. methoxy, ethoxy, n-propoxy, 1-methylethoxy, butoxy, 1-methylpropoxy, 2-methylpropoxy or 1,1-dimethylethoxy.

Fluoroalkoxy: alkoxy as described above, in which the hydrogen atoms of these groups are partly or completely replaced by fluorine atoms, i.e. for example $C_1$-$C_4$-fluoroalkoxy, in particular $C_1$-$C_2$-fluoroalkoxy, such as fluoromethoxy, difluoromethoxy, trifluoromethoxy, 2-fluoroethoxy, 2,2-difluoroethoxy, 2,2,2-trifluoroethoxy, pentafluoroethoxy, 2-fluoropropoxy, 3-fluoropropoxy, 2,2- difluoropropoxy, 2,3-difluoropropoxy, 3,3,3-trifluoropropoxy, 2,2,3,3,3-pentafluoropropoxy, heptafluoropropoxy, 1-(fluoromethyl)-2-fluoroethoxy, specifically fluoromethoxy, difluoromethoxy, trifluoromethoxy, 2-fluoroethoxy, or 2,2,2-trifluoroethoxy.

Alkylsulfanyl: an alkyl radical as defined above having normally 1 to 6 C atoms, in particular 1 to 4 C atoms, which is connected to the remainder of the molecule via an sulfur atom: e.g. methylsulfanyl, ethylsulfanyl, n-propylsulfanyl, 1-methylethsulfanyl, butylsulfanyl, 1-methylpropylsulfanyl, 2-methylpropylsulfanyl or 1,1-dimethylethylsulfanyl.

Fluorinated alkylsulfanyl: alkylsulfanyl as described above, in which the hydrogen atoms of these groups are partly or completely replaced by fluorine atoms, i.e. for example $C_1$-$C_4$-fluoroalkylsulfanyl, in particular $C_1$-$C_2$-fluoroalkylsulfanyl, such as fluoromethylsulfanyl, difluoromethylsulfanyl, trifluoromethylsulfanyl, 2-fluoroethylsulfanyl, 2,2-difluoroethylsulfanyl, 2,2,2-trifluoroethylsulfanyl, pentafluoroethylsulfanyl, 2-fluoropropylsulfanyl, 3-fluoropropylsulfanyl, 2,2-difluoropropylsulfanyl, 2,3-difluoropropylsulfanyl, 3,3,3-trifluoropropylsulfanyl, 2,2,3,3,3-pentafluoropropylsulfanyl, heptafluoropropylsulfanyl, 1-(fluoromethyl)-2-fluoroethylsulfanyl, specifically fluoromethylsulfanyl, difluoromethylsulfanyl, trifluoromethylsulfanyl, 2-fluoroethylsulfanyl, or 2,2,2-trifluoroethylsulfanyl.

Alkylsulfonyl: an alkyl radical as defined above having normally 1 to 6 C atoms, in particular 1 to 4 C atoms, which is connected to the remainder of the molecule via an $S(O)_2$ moiety: e.g. methylsulfonyl, ethylsulfonyl, n-propylsulfonyl, 1-methylethsulfonyl, butylsulfonyl, 1-methylpropylsulfonyl, 2-methylpropylsulfonyl or 1,1-dimethylethylsulfonyl.

Fluorinated alkylsulfonyl: alkylsulfonyl as described above, in which the hydrogen atoms of these groups are partly or completely replaced by fluorine atoms, i.e. for example $C_1$-$C_4$-fluoroalkylsulfonyl, in particular $C_1$-$C_2$-fluoroalkylsulfonyl, such as fluoromethylsulfonyl, difluoromethylsulfonyl, trifluoromethylsulfonyl, 2-fluoroethylsulfonyl, 2,2-difluoroethylsulfonyl, 2,2,2-trifluoroethylsulfonyl, pentafluoroethylsulfonyl, 2-fluoropropylsulfonyl, 3-fluoropropylsulfonyl, 2,2-difluoropropylsulfonyl, 2,3-difluoropropylsulfonyl, 3,3,3-trifluoropropylsulfonyl, 2,2,3,3,3-pentafluoropropylsulfonyl, heptafluoropropylsulfonyl, 1-(fluoromethyl)-2-fluoroethylsulfonyl, specifically fluoromethylsulfonyl, difluoromethylsulfonyl, trifluoromethylsulfonyl, 2-fluoroethylsulfonyl, or 2,2,2-trifluoroethylsulfonyl.

Hydroxyalkyl: an alkyl radical ordinarily having 1 to 4 C atoms, in which one hydrogen atom is replaced by an OH radical. Examples thereof are $CH_2$—OH, 1-hydroxyethyl, 2-hydroxyethyl, 1-hydroxypropyl, 2-hydroxypropyl, 1-methyl-1-hydroxyethyl, 1-methyl-2-hydroxyethyl, 3-hydroxypropyl, 2-hydroxybutyl, 3-hydroxybutyl, 4-hydroxybutyl, 1-methyl-2-hydroxypropyl, 1,1-dimethyl-2-hydroxyetyl, 1-methyl-1-hydroxypropyl etc.

Alkoxyalkyl: an alkyl radical ordinarily having 1 to 4 C atoms, in which one hydrogen atom is replaced by an alkoxy radical ordinarily having 1 to 4 C atoms. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl, 4-(1,1-dimethylethoxy)butyl, etc.

Alkoxyalkoxy: an alkoxyalkyl radical as defined above ordinarily having 1 to 4 C atoms both in the alkoxy and the alkyl moiety which is connected to the remainder of the molecule via an O atom: Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy)methoxy, $OCH_2$—$OC(CH_3)_3$, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

Alkylen or alkanediyl, respectively: a saturated hydrocarbon chain having ordinarily from 1 to 4 carbon atoms, such as methylen (—$CH_2$—), 1,2-ethylen (—$CH_2CH_2$—), 1,1-ethanediyl (—$CH(CH_3)$—), 1,2-propanediyl, 1,3-propanediyl, 1,4-butanediyl, 1,2-butandiyl, 1,3-butanediyl, 1-methyl-1,2-propanediyl, 2-methyl-1,3-propanediyl, 1-methyl-1,1-ethanediyl, 1-methyl-1,2-propanediyl etc.

Saturated or partially unsaturated, heterocyclic radicals include saturated or partially unsaturated, monocyclic heterocyclic radical ordinarily having 3, 4, 5, 6, 7 or 8 ring atoms and heterobicyclic radical ordinarily having 7, 8, 9 or 10 ring atoms. Besides carbon atoms, 1, 2 or 3, of the ring atoms are heteroatoms such as N, S or O, or heteroatom moieties such as NR, S(=O) or S(=O)$_2$.

Examples of saturated heteromonocyclic radicals are in particular

Saturated heteromonocyclic radical which ordinarily has 3, 4, 5, 6 or 7 ring atoms, where ordinarily 1, 2 or 3 of the ring atoms are heteroatoms such as N, S or O, besides carbon atoms as ring members. These include for example:

C-bonded, 3- or 4-membered saturated rings such as 2-oxiranyl, 2-oxetanyl, 3-oxetanyl, 2-aziridinyl, 3-thiethanyl, 1-azetidinyl, 2-azetidinyl.

C-bonded, 5-membered saturated rings such as tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl.

C-bonded, 6-membered saturated rings such as: tetrahydropyran-2-yl, tetrahydropyran-3-yl, tetrahydropyran- 4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl.

N-bonded, 5-membered saturated rings such as: tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl.

N-bonded, 6-membered saturated rings such as: piperidin-1-yl, hexahydropyrimidin-1-yl, hexahydropyrazin-1-yl, hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl.

saturated heterobicyclic radicals which ordinarily have 8, 9 or 10 ring atoms, where ordinarily 1, 2 or 3 of the ring atoms are heteroatoms such as S or O or heteroatom moieties such as NH, N-alkyl, besides carbon atoms as ring members. These include e.g. 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, 2,3,4,4a,5,6,7,7a-octahydro-1H-cyclopenta[b]pyridinyl, 2,3,3a,4,5,6,7,7a-octahydro-1H-indolyl, 1,2,3,4,4a,5,6,7,8,8a-decahydroquinolinyl and 1,2,3,4,4a,5,6,7,8,8a-decahydroisoquinolinyl and the N—$C_1$-$C_4$-alkyl analogues;

Unsaturated heteromonocyclic radicals which ordinarily have 4, 5, 6 or 7 ring atoms, where ordinarily 1, 2 or 3 of the ring atoms are heteroatoms such as N, S or O, besides carbon atoms as ring members. These include for example:

C-bonded, 5-membered, partially unsaturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl.

C-bonded, 6-membered, partially unsaturated rings such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin- 4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl.

N-bonded, 5-membered, partially unsaturated rings such as: 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl.

N-bonded, 6-membered, partially unsaturated rings such as: 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

partially unsaturated heterobicyclic radicals, also termed which ordinarily have 8, 9 or 10 ring atoms, where ordinarily 1, 2 or 3 of the ring atoms are heteroatoms such as S or O or heteroatom moieties such as NH, N-alkyl, besides carbon atoms as ring members. These include e.g. 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, 2,3,4,4a,5,6,7,7a-octahydro-1H-cyclopenta[b]pyridinyl, 2,3,3a,4,5,6,7,7a-octahydro-1H-indolyl, 1,2,3,4,4a,5,6,7,8,8a-decahydroquinolinyl and 1,2,3,4,4a,5,6,7,8,8a-decahydroisoquinolinyl and the N—$C_1$-$C_4$-alkyl analogues;

Examples of partially unsaturated heterobicycles are in particular radicals corresponding to saturated or partially unsaturated bicarbocyclic radicals, wherein 1, 2 or 3 CH or $CH_2$ moieties have been replaced by N, NH, O, S, S(=O) or $S(=O)_2$, such as 2-oxa-6-azaspiro-[3,4]octyl, 2-azabicyclo[2.2.1]heptyl, 5-azabicyclo[2.2.1]heptyl, 2,5-diazabicyclo[2.2.1]heptyl, 3-azabicyclo[3.2.1]octyl, 8-azabicyclo[3.2.1]octyl, 3,8-diazabicyclo[3.2.1]octyl, dihydroindolyl, dihydroindolizynyl, dihydroisoindolyl, dihydroquinolinyl, dihydroisoquinolinyl, chromenyl and chromanyl.

Hetaryl: a 5- or 6-membered aromatic heteromonocyclic radical (also termed 5- or 6-membered monocyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members and a 8-, 9- or 10-membered aromatic heterobicyclic radical (also termed 8-, 9- or 10-membered bicyclic hetaryl) which ordinarily has 1, 2, 3 or 4 heteroatoms as ring members, which are selected from O, S and N, and which has in particular 1, 2, 3 or 4 nitrogen atoms or a heteroatom selected from oxygen and sulfur and, if appropriate, 1 or 2 nitrogen atoms as ring members besides carbon atoms as ring members: for example C-bonded, 5-membered monocyclic hetaryl having 1, 2 or 3 or 4 nitrogen atoms or a heteroatom selected from oxygen and sulfur and, if appropriate, having 1, 2 or 3 nitrogen atoms as ring members, such as:

2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol- 5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl.

C-bonded, 6-membered monocyclic hetaryl having 1, 2 or 3 nitrogen atoms as ring members, such as:

pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl.

N-bonded, 5-membered heteroaromatic radicals having 1, 2, 3 or 4 nitrogen atoms as ring members, such as:

pyrrol-1-yl, pyrazol-1-yl, imidazol-1-yl, 1,2,3-triazol-1-yl, 1,2,4-triazol-1-yl, tetrazol-1-yl.

bicyclic 8-, 9-10-membered hetaryl, hetaryl which has one of the aforementioned 5- or 6-membered heteroaromatic rings and a further aromatic carbocycle or 5- or 6-membered heterocycle fused thereto, for example a fused benzene, thiophene, furane, pyrrole, pyrazole, imidazole, pyridine or pyrimidine ring. These bicyclic hetaryl include for example quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

In relation to their use as inhibitors of PDE10A, the variables Q, X, Y, Z, Het, A, $R^1$, $R^2$, $R^3$, $R^4$, $R^5$, $R^6$, $R^7$, $R^8$ and $R^9$ preferably have the following meanings, where these represent, both considered on their own and in combination with at least one other or all, special configurations of the compounds of the formula I:

An embodiment of the invention relates to compounds of the formula I, where

X is $CR^{x1}R^{x2}$ or C(O), where
  $R^{x1}$ and $R^{x2}$, independently of each other are hydrogen, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, optionally substituted by 1, 2 or 3 methyl groups, and fluorinated $C_3$-$C_6$-cycloalkyl or the radicals $R^{x1}$ and $R^{x2}$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

Y is $CR^{y1}R^{y2}$ or C(O)
  $R^{y1}$ and $R^{y2}$, independently of each other are hydrogen, halogen, $C_1$-$C_4$-alkyl, trimethylsilyl, $C_1$-$C_4$-fluoroalkyl, $C_1$-$C_4$-fluoroalkoxy, $C_3$-$C_6$-cycloalkyl, optionally substituted by 1, 2 or 3 methyl groups, and fluorinated $C_3$-$C_6$-cycloalkyl or the radicals $R^{y1}$ and $R^{y2}$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;
  provided that one or both of X and Y is/are C(O);

A is O, $[C(R^6,R^7)]_k$ with k=1 or 2, $OC(R^6,R^7)$, $C(R^8)=C(R^9)$ or C≡C;

Het is selected from the group consisting of
  i. monocyclic 5- or 6-membered hetaryl having 1 or 2 nitrogen atoms and optionally a further heteroatom selected from the group consisting of O, S and N as ring members, which is unsubstituted or may carry 1, 2, 3 or 4 identical or different substituents $R^a$,
  ii. fused 8-, 9- or 10-membered bicyclic hetaryl having one heteroatom selected from the group consisting of O, S and N and optionally 1, 2 or 3 nitrogen atoms as ring members, where the fused bicyclic hetaryl is unsubstituted or may carry 1, 2, 3 or 4 identical or different substituents $R^a$,
  iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^{aa}$, and where hetaryl is unsubstituted or carries 1, 2 or 3 radicals $R^a$;
  $R^a$ is selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, O—$C_3$-$C_6$-cycloalkyl, benzyloxy, C(O)O—($C_1$-$C_4$-alkyl), O—($C_1$-$C_4$-alkyl)-$R^{14}$, $CO_2H$, $C_1$-$C_4$ alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $NR^{13}R^{14}$, $C(O)NR^{13}R^{14}$, $C_1$-$C_4$-alkyl-$NR^{13}R^{14}$, —$NR^{15}$—C(O)—$NR^{13}R^{14}$, $NR^{15}$—C(O)O—($C_1$-$C_4$-alkyl), —$NR^{15}$—$SO_2$—$R^{12}$, CN, —$SF_5$, —$OSF_5$, —$SO_2R^{12}$, —$SR^{12}$ and trimethylsilyl, or
    two radicals $R^a$, which are bound to adjacent ring atoms may also form linear $C_3$-$C_5$-alkandiyl, wherein 1 or 2 $CH_2$ moieties can be replaced by C=O, O, S, S(=O), S(=O)$_2$ or NR', and where alkanediyl is unsubstituted or may carry 1 or 2 radicals selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy;
  $R^{aa}$ has one of the meanings given for $R^a$ or one radical $R^{aa}$ may also be phenyl or a 5- or 6-membered hetaryl having 1 or 2 nitrogen atoms and optionally a further heteroatom selected from the group consisting of O, S and N as ring members, where phenyl and hetaryl are unsubstituted or may carry 1, 2 or 3 radicals selected from the group consisting of halogen, OH, $C_1$-$C_4$-alkyl, $C_1$-$C_4$-haloalkyl, $C_1$-$C_4$-alkoxy and $C_1$-$C_4$-haloalkoxy;

Q is O or S;

Z is selected from the group consisting of a chemical bond, $CH_2$, O, O—$CH_2$, C(O)O, C(O), $NR^z$, $NR^z$—$CH_2$, S(O)$_2$—$NR^z$, C(O)—$NR^z$, S, S(O), S(O)$_2$, C(O)—O—$CH_2$, C(O)—$NR^z$—$CH_2$, 1,2-ethandiyl, 1,2-ethendiyl and 1,2-ethyndiyl, where $R^z$ is selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;

$R^1$ is selected from the group consisting of phenyl, naphthyl, $C_3$-$C_8$-cycloalkyl, 3- to 8-membered saturated or partially unsaturated heteromonocyclic radicals, saturated or partially unsaturated 7- to 10-membered heterobicyclic radicals, 5- or 6-membered monocyclic hetaryl, and 8- to 10-membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, $SO_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_8$-cycloalkyl, the saturated or partially unsaturated heteromonocyclic and heterobicyclic radicals are unsubstituted or carry 1, 2, 3, 4 or 5 radicals $R^{C1}$ or one radical Y'—$R^{C2}$ and 0, 1, 2, 3 or 4 radicals $R^{C1}$; where phenyl, naphthyl, the mono and bicyclic heteroaromatic radicals are unsubstituted or carry 1, 2, 3, 4 or 5 radicals $R^{C3}$ or one radical Y'—$R^{C2}$ and 0, 1, 2, 3 or 4 radicals $R^{C3}$; where $R^{C1}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^h$, Z'—$C(O)OR^b$, Z'—$C(O)NR^cR^d$, $NR^gSO_2R^h$, $S(O)_2NR^cR^d$ and Z'—$NR^eR^f$, where
  $R^b$, $R^g$ independently of each other are selected from the group consisting of hydrogen, $C_1$-$C_4$-alkyl, $C_2$-$C_4$-alkenyl and $C_1$-$C_4$-fluoroalkyl,
  $R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy,
  $R^e$, $R^f$ independently of each other are selected from the group consisting of hydrogen, $C_1$-$C_4$-alkyl, $C_1$-$C_4$-fluoroalkyl, $C_1$-$C_4$-hydroxyalkyl, $C_1$-$C_4$-alkoxy-$C_1$-$C_4$-alkyl, $C_1$-$C_4$-alkoxy and $C_1$-$C_4$-fluoroalkoxy,
  $R^h$ is selected from the group consisting of $C_1$-$C_4$-alkyl and $C_1$-$C_4$-fluoroalkyl,
  Z' is a covalent bond or $C_1$-$C_4$-alkanediyl,
  or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are selected from the group consisting of O, S and N;
  or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are selected from the group consisting of O, S and N,
  or two radicals $R^{C1}$ which are bound at the same carbon atom may form an oxygen atom,
  where the fused and the spiro radicals are unsubstituted or carry 1, 2, 3 or 4 radicals $R^{c4}$;
Y' is a chemical bond, $CH_2$, O, O—$CH_2$, C(O), $S(O)_2$, $NR^{3''}$, $NR^{3''}$-$CH_2$ or $NR^{3''}$-$S(O)_2$, where $R^{3''}$ is selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;
$R^{C2}$ is a carbocyclic or heterocyclic radical selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{c4}$;
$R^{C3}$ is selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, $C(O)R^h$, Z'—$C(O)OR^b$, Z'—$C(O)NR^cR^d$, $NR^gSO_2R^h$, $S(O)_2NR^cR^d$ and Z'—$NR^eR^f$, wherein Z', $R^b$, $R^c$, $R^d$, $R^e$ and $R^f$ and $R^h$ are as defined above, or two radicals $R^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are selected from the group consisting of O, S and N, where the carbocyclic and the heterocyclic radical are unsubstituted or carry 1, 2, 3, 4 or 5 radicals $R^{c4}$;
$R^{C4}$ is selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^h$, benzyl, Z'—$C(O)OR^b$, Z'—$C(O)NR^cR^d$, $S(O)_2NR^cR^d$ and Z'—$NR^eR^f$, where, Z', $R^b$, $R^e$, $R^d$, $R^e$ and $R^f$ and $R^h$ are as defined above or two radicals $R^{C3}$ which are bound at the same atom may form an oxygen atom;
$R^2$ is selected from the group consisting of hydrogen, $C_1$-$C_6$-alkyl, $C_2$-$C_6$-alkenyl, $C_2$-$C_6$-alkynyl, $C_1$-$C_4$-alkyl-CN, $C_1$-$C_4$—$OR^{21}$, $C_1$-$C_4$-alkyl-$SR^{22}$, $C_1$-$C_4$-alkyl-$NR^{23}R^{24}$, $C_1$-$C_6$-fluoroalkyl, $C_3$-$C_6$-cycloalkyl, $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups, phenyl, phenyl-$C_1$-$C_4$-alkyl, 5- or 6-membered hetaryl and 5- or 6-membered hetaryl-$C_1$-$C_4$-alkyl, where hetaryl has 1 heteroatom selected from the group consisting of O, S and N as ring member and 0, 1 or 2 further N atoms as ring members, and wherein phenyl and hetaryl in the last four mentioned radicals are unsubstituted or carry 1 or 2 radicals selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^h$, benzyl, Z'—$C(O)OR^b$, Z'—$C(O)NR^cR^d$, $S(O)_2NR^cR^d$ and Z'—$NR^eR^f$, where, Z', $R^b$, $R^c$, $R^d$, $R^e$, $R^f$ and $R^h$ are as defined above;
$R^3$ is selected from the group consisting of hydrogen, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, OH, hydroxy-$C_1$-$C_4$-alkyl, O—$C_3$-$C_6$-cycloalkyl, benzyloxy, C(O)O—($C_1$-$C_4$-alkyl), O—($C_1$-$C_4$-alkyl)-$CO_2H$, $C_1$-$C_4$-alkyl-$OR^{31}$, $C_1$-$C_4$-alkyl-$SR^{32}$, $C_1$-$C_4$-alkyl-$NR^{33}R^{34}$, $OC_1$-$C_4$-alkyl-$OR^{11}$, $OC_1$-$C_4$-alkyl-$SR^{32}$, $OC_1$-$C_4$-alkyl-$NR^{33}R^{34}$, $NR^{33}R^{34}$, $C(O)NR^{33}R^{34}$, $C_1$-$C_4$-alkyl-$NR^{33}R^{34}$, —$NR^{35}$—C(O)—$NR^{33}R^{34}$, $NR^{35}$—C(O)O—($C_1$-$C_4$-alkyl), —$NR^{35}$—$SO_2$—$R^{32}$, phenyl, CN, —$SF_5$, —$OSF_5$, —$SO_2R^{32}$, —$SR^{32}$ and trimethylsilyl;
$R^4$, $R^5$ independently of each other are selected from the group consisting of hydrogen, halogen, $C_1$-$C_4$-alkyl, trimethylsilyl, $C_1$-$C_4$-fluoroalkyl, $C_1$-$C_4$-alkoxy, $C_1$-$C_4$-fluoroalkoxy, $C_3$-$C_6$-cycloalkyl, or the radicals $R^4$, $R^5$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;
$R^6$, $R^7$ independently of each other are selected from the group consisting of hydrogen, halogen, $C_1$-$C_4$-alkyl, trimethylsilyl, $C_1$-$C_4$-fluoroalkyl, $C_1$-$C_4$-alkoxy, $C_1$-$C_4$-fluoroalkoxy, $C_3$-$C_6$-cycloalkyl, or the radicals $R^4$, $R^5$ together with the carbon atom to which they are bound form a saturated 3- to 6-membered carbocycle or a saturated 3- to 6-membered heterocycle having 1 or 2 non-adjacent heteroatoms, which are selected from the group consisting of O, S and N, as ring members, where the carbocycle and the heterocycle are unsubstituted or may carry 1, 2, 3 or 4 substituents selected from the group consisting of fluorine and methyl;

$R^8$, $R^9$ independently of each other are selected from the group consisting of hydrogen, halogen, $C_1$-$C_4$-alkyl and $C_1$-$C_4$-fluoroalkyl, the moiety $C(R^4,R^5)$-A may also form a moiety $C(R^8)=C(R^9)$, $C\equiv C$, $C(R^8)=C(R^9)-C(R^6,R^7)$ or $C\equiv C-C(R^6,R^7)$, the moiety $C(R^4,R^5)$-A may also form a cyclopropane-1,2-diyl or cyclopropane-1,2-diyl-$C(R^6,R^7)$, where the cyclopropane-1,2-diyl moiety is unsubstituted or carries 1 or 2 radicals selected from the group consisting of halogen, $C_1$-$C_4$-alkyl, trimethylsilyl, $C_1$-$C_4$-fluoroalkyl, $C_1$-$C_4$-alkoxy and $C_1$-$C_4$-fluoroalkoxy;

and where $R^{11}$, $R^{12}$, $R^{21}$, $R^{22}$, $R^{31}$ and $R^{32}$ independently of each other are selected from the group consisting of hydrogen, $C_1$-$C_4$-alkyl, $C_1$-$C_4$-fluoroalkyl, $C_3$-$C_6$-cycloalkyl, $C_3$-$C_6$-cycloalkyl-$C_1$-$C_4$-alkyl, where $R^{11}$ may also be $C_1$-$C_4$-alkylsulfonyl and $C_1$-$C_4$-fluoroalkylsulfonyl;

$R^{13}$, $R^{14}$ independently of each other are selected from the group consisting of hydrogen, $C_1$-$C_4$-alkyl, $C_1$-$C_4$-fluoroalkyl $C_3$-$C_6$-cycloalkyl and $C_3$-$C_6$-cycloalkyl-$C_1$-$C_4$-alkyl, or $R^{13}$ and $R^{14}$ together with the N atom to which they are attached form a 3- to 7-membered, nitrogen heterocycle which may have 1, 2 or 3 further different or identical heteroatoms or heteroatom containing groups selected from the group consisting of O, N, S, SO and $SO_2$ as ring members and which may carry 1, 2, 3, 4, 5 or 6 $C_1$-$C_4$-alkyl substituents;

$R^{23}$, $R^{24}$, $R^{33}$ and $R^{34}$ have one of the meanings given for $R^{13}$, $R^{14}$;

$R^{15}$, $R^{35}$ independently of each other are selected from the group consisting hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl; and R' is hydrogen, hydrogen, $C_1$-$C_4$-alkyl, $C_1$-$C_4$-fluoroalkyl, $C_3$-$C_6$-cycloalkyl or $C_3$-$C_6$-cycloalkyl-$C_1$-$C_4$-alkyl;

and the N-oxides, the prodrugs, the tautomers and the hydrates thereof, and the pharmaceutically acceptable salts thereof.

In a first group of particular embodiments of the invention, the variable X is C(O) while the variable Y is $C(R^{y1},R^{y2})$. In these groups of embodiments, $R^{y1}$ and $R^{y2}$, independently of each other, are in particular selected from the group consisting of hydrogen, fluorine and methyl. $R^{y1}$ and $R^{y2}$ are especially hydrogen. These compounds are hereinafter also termed compounds I.A.

In a second group of particular embodiments of the invention, the variable X is $C(R^{x1},R^{x2})$ while the variable Y is C(O). In these groups of embodiments, $R^{x1}$ and $R^{x2}$, independently of each other, are in particular selected from the group consisting of hydrogen, fluorine and methyl. $R^{x1}$ and $R^{x2}$ are especially hydrogen. These compounds are hereinafter also termed compounds I.B.

In a third group of particular embodiments of the invention, the variables X and Y are both C(O). These compounds are hereinafter also termed compounds I.C.

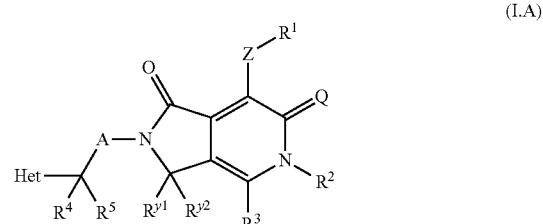

(I.A)

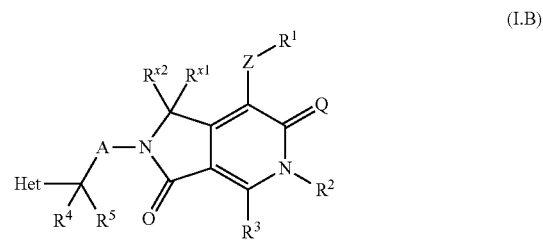

(I.B)

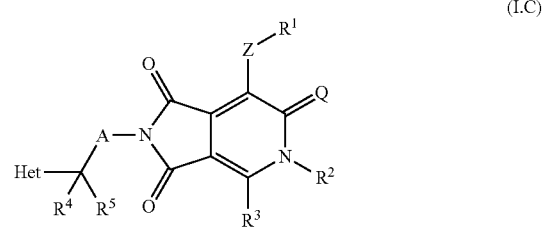

(I.C)

In formula I and likewise in formulae I.A, I.B and I.C, the variable A is in particular $C(R^6,R^7)$, $[C(R^6,R^7)]_k$ with k=2, such as 1,2-propanediyl, 1,2-ethanediyl or ethynediyl. In formula I and likewise in formulae I.A, I.B and I.C, the variable A is more particularly $C(R^6,R^7)$. In this context, $R^6$, $R^7$ are preferably hydrogen, fluorine or methyl or the moiety $C(R^6,R^7)$ is 1,1-cyclopropanediyl. Especially, A is $CH_2$.

In formula I and likewise in formulae I.A, I.B and I.C, the variable Z is in particular, a bond, O or NH. Especially Z is a bond.

In particularly preferred embodiments of the invention, X is C(O), Y is $C(R^{y1},R^{y2})$ and A is $CH_2$, i.e. formula I can be described by the following formula I.A.a:

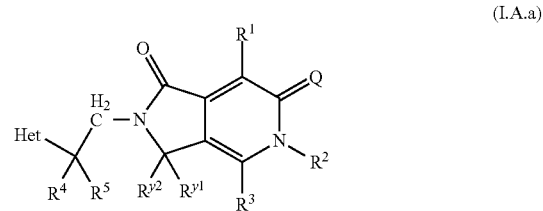

(I.A.a)

where Het, Q, $R^1$, $R^2$, $R^3$, $R^4$, $R^5$, $R^{y1}$ and $R^{y2}$ are as described herein.

In another particular group of embodiments of the invention, X is $C(R^{x1},R^{x2})$, Y is C(O) and A is $CH_2$, i.e. formula I can be described by the following formula I.B.a:

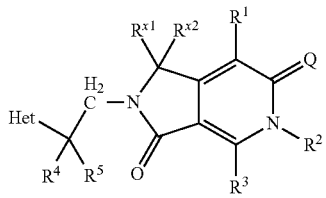

(I.B.a)

where Het, Q, $R^1$, $R^2$, $R^3$, $R^4$, $R^5$, $R^{x1}$ and $R^{x2}$ are as described herein.

In yet another particular group of embodiments of the invention, X is C(O), Y is C(O) and A is $CH_2$, i.e. formula I can be described by the following formula I.C.a:

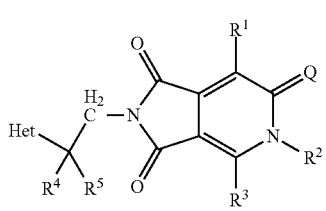

(I.C.a)

where Het, Q, $R^1$, $R^2$, $R^3$, $R^4$ and $R^5$ are as described herein.

In formula I and likewise in formulae I.A, I.B, I.C, I.A.a, I.B.a and I.C.a, the variable Q is in particular O.

In formula I and likewise in formulae I.A, I.B, I.C, I.A.a, I.B.a and I.C.a, the radical $R^1$ is in particular selected from the radicals of the following groups (i) and (ii):

(i) Group (i) radicals are selected from the group consisting of saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom containing group as ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$, in particular 1, 2, or 3 radicals $R^{C1}$, or one radical Y'—$R^{C2}$ and 0, 1, 2, 3 or 4 radicals $R^{C1}$, in particular 0, 1, or 2 radicals $R^{C1}$, where $R^{C1}$, $R^{C2}$ and Y' are as defined herein and wherein Y' is in particular a chemical bond;

(ii) Group (ii) radicals are selected from the group consisting of phenyl, 5- or 6-membered monocyclic hetaryl, and 9- or 10-membered bicyclic hetaryl, where hetaryl has one heteroatom, selected from the group consisting of O, S and N as ring member and optionally one or two further nitrogen atoms as ring members, where phenyl and the hetaryl radical are unsubstituted or either carry, independently of each other, 1, 2, 3, 4 or 5 radicals $R^{C3}$, in particular 1, 2, or 3 radicals $R^{C3}$, or one radical Y'—$R^{C2}$ and 0, 1, 2, 3 or 4 radicals $R^{C3}$, in particular 0, 1, or 2 radicals $R^{C3}$.

In a first particular group of embodiments, $R^1$ is a group (i) radical.

If $R^1$ is a group (i) radical, Z is in particular selected from a single bond, O and NH. In this regard, $R^{C1}$ is preferably selected from the group consisting of fluorine, chlorine, CN, methyl, difluoromethyl, trifluoromethyl, methoxy and $NH_2$. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated heteromonocyclic radicals, having 1, 2 or 3 heteroatoms as ring members, which are selected from O, S and N, where phenyl and the saturated heteromonocyclic radical are unsubstituted or carry 1, 2 or 3 radicals $R^{C4}$, which are preferably selected from fluorine, chlorine, CN, methyl, difluoromethyl, trifluoromethyl, methoxy and $NH_2$.

If $R^1$ is a group (i) radical, $R^1$ is in particular an unsubstituted cyclic radical or a cyclic radical which carries 1, 2 or 3 radicals $R^{C1}$.

If $R^1$ is a group (i) radical, $R^1$ is in particular a saturated 4-, 5-, 6- or 7-membered heteromonocycle, where the heteromonocycle has one nitrogen or oxygen atom as ring member and may have one further heteroatom or heteroatom containing group as ring member, which is selected from the group consisting of O, S, S(=O), S(=O)$_2$ and N, where the saturated heteromonocycle is unsubstituted or carries 1, 2, or 3 radicals $R^{C1}$, where $R^{C1}$ is as defined herein If $R^1$ is a group (i) radical, the moiety Z—$R^1$ is in more particularly selected from the group consisting of 1-piperidinyl, 4,4-difluoro-1-piperidinyl, 4-hydroxylpiperidin-1-yl, 4-piperidinyl, 1-methyl-4-piperidinyl, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino.

If $R^1$ is a group (i) radical, the moiety Z—$R^1$ is more particularly 4-morpholinyl, oxetan-3-ylamino or 4-morpholinylmethyl and especially 4-morpholinyl.

In a further particular group of embodiments, $R^1$ is a group (ii) radical.

If $R^1$ is a group (ii) radical, Z is in particular a single bond.

In this regard, $R^{C3}$ is preferably selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)$NH_2$ and $NH_2$, especially from the group consisting of fluorine, chlorine, OH, CN, methyl, difluoromethyl, trifluoromethyl, methoxy, 2-methoxyethyl, C(O)$NH_2$, C(O)OCH$_3$ and $NH_2$, or, if $R^1$ is phenyl, two radicals $R^{C3}$ which are bound to adjacent carbon atoms, together with the phenyl ring to which they are bound, form a bicyclic heterocyclic radical, which is selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl. In this regard, $R^{C2}$ is preferably selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, such as 1-piperidinyl, 1-piperazinyl, 4-methyl-1-piperazinyl, 4-morpholinyl, pyridyl, pyrimidinyl, 1-pyrazolyl, or 1-imidazolyl, where phenyl and the saturated or aromatic heteromonocyclic radicals are unsubstituted or carry 1, 2 or 3 radicals $R^{C4}$, which are as defined above and which are preferably selected from the group consisting of fluorine, chlorine, CN, methyl, difluoromethyl, trifluoromethyl, methoxy and $NH_2$.

If $R^1$ is a group (ii) radical, the moiety Z—$R^1$ is in particular selected from the group consisting of phenyl, 5- or 6-membered monocyclic hetaryl selected from the group consisting of pyridyl, pyrimidinyl, furyl, thienyl, pyrrolyl, imidazolyl, pyrazolyl, oxazolyl and thiazolyl, 9- or 10-membered bicyclic hetaryl selected from the group consisting of indolyl, quinolinyl, isoquinolinyl, quinazolinyl, benzimidazolyl, 1,3-bezoxazolyl, 1,3-benzothiazolyl, benzotriazolyl, benzopyrazolyl, benzothienyl and benzofuryl, where phenyl, the monocyclic and bicyclic hetaryl are unsubstituted or carry 1, 2 or 3 radicals $R^{C3}$ which are in particular selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)NH$_2$ and NH$_2$, especially from the group consisting of fluorine, chlorine, OH, CN, methyl, difluoromethyl, trifluoromethyl, methoxy, 2-methoxyethyl, C(O)NH$_2$, C(O)OCH$_3$ and NH$_2$, or carry one radical Y'—$R^{C2}$, where Y' is a bond, CH$_2$ or C(O) and $R^{C2}$ is in particular 1-piperidinyl, 1-piperazinyl, 4-methyl-1-piperazinyl, 4-morpholinyl, pyridyl, pyrimidinyl, 1-pyrazolyl, or 1-imidazolyl, or, if $R^1$ is phenyl, two radicals $R^{C3}$ which are bound to adjacent carbon atoms, together with the phenyl ring to which they are bound, form a bicyclic heterocyclic radical, which is in particular selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

If $R^1$ is a group (ii) radical, $R^1$ is more particularly selected from the group consisting of phenyl and 5- or 6 membered hetaryl, selected from pyridyl, pyrimidinyl, furyl, thienyl, pyrrolyl, imidazolyl, pyrazolyl, oxazolyl and thiazolyl, where phenyl and the 5- or 6 membered hetaryl are unsubstituted or carry 1, 2, 3, 4 or 5, in particular 1, 2, or 3 radicals $R^{C1}$ or one radical Y'—$R^{C2}$ and 0, 1, 2, 3 or 4, in particular 0, 1 or 2 radicals $R^{C3}$, where $R^{C3}$, $R^{C2}$ and Y' are as defined herein and where Y', if present, is preferably a chemical bond.

If $R^1$ is a group (ii) radical, $R^1$ is even more particularly selected from the group consisting of 3-pyridyl, 4-pyridyl, 4-fluorophenyl, 5-pyrimidinyl, pyrazol-4-yl, 1-methylpyrazol-5-yl and 4-methoxyphenyl, especially selected from the group consisting of 4-pyridyl and 4-fluorophenyl.

If $R^1$ is a group (ii) radical, Z—$R^1$ is even more particularly selected from the group consisting of 3-pyridyl, 4-pyridyl, 4-fluorophenyl, 5-pyrimidinyl, pyrazol-4-yl, 1-methylpyrazol-5-yl and 4-methoxyphenyl, especially selected from the group consisting of 4-pyridyl and 4-fluorophenyl.

In formula I and likewise in formulae I.A, I.B, I.C, I.A.a, I.B.a and I.C.a, the radical $R^2$ is in particular selected from the group consisting of hydrogen, $C_1$-$C_6$-alkyl, $C_1$-$C_4$-alkyl-OR$^{21}$, $C_1$-$C_4$-alkyl-NR$^{23}$R$^{24}$, $C_1$-$C_6$-fluoroalkyl, $C_3$-$C_6$-cycloalkyl-$C_1$-$C_4$-alkyl, where the cycloalkyl moiety is unsubstituted, partially or completely fluorinated, or substituted by 1, 2 or 3 methyl groups and phenyl-$C_1$-$C_4$-alkyl, wherein phenyl in the last mentioned radicals are unsubstituted or carry 1 or 2 radicals selected from halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)R$^h$, benzyl, Z'—C(O)OR$^b$, Z'—C(O)NR$^c$R$^d$, S(O)$_2$NR$^c$R$^d$ and Z'—NR$^e$R$^f$, where Z', $R^{21}$, $R^{23}$, $R^{24}$, $R^h$, $R^b$, $R^e$, $R^d$, $R^e$ and $R^f$ are as defined herein.

In formula I and likewise in formulae I.A, I.B, I.C, I.A.a, I.B.a and I.C.a, the radical $R^2$ is more particularly selected from the group consisting of hydrogen, $C_1$-$C_6$-alkyl, $C_1$-$C_4$-alkoxy-$C_1$-$C_4$-alkyl, $C_1$-$C_6$-fluoroalkyl, $C_3$-$C_6$-cycloalkyl-$C_1$-$C_4$-alkyl, and phenyl-$C_1$-$C_4$-alkyl, wherein phenyl in the last mentioned radical is unsubstituted or carries 1 or 2 radicals selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl and $C_1$-$C_4$-fluoroalkoxy.

In formula I and likewise in formulae I.A, I.B, I.C, I.A.a, I.B.a and I.C.a, the radical $R^2$ is even more particularly selected from the group consisting of $C_1$-$C_3$-alkyl, $C_1$-$C_3$-fluoroalkyl, $C_1$-$C_2$-alkoxy-$C_1$-$C_2$-alkyl, and benzyl, wherein phenyl in benzyl is unsubstituted or carries 1 or 2 radicals selected from the group consisting of halogen, OH, CN, $C_1$-$C_2$-alkyl, $C_1$-$C_2$-alkoxy, hydroxy-$C_1$-$C_2$-alkyl, $C_1$-$C_2$-alkoxy-$C_1$-$C_2$-alkyl, cyano-$C_1$-$C_2$-alkyl, $C_1$-$C_2$-fluoroalkyl and $C_1$-$C_2$-fluoroalkoxy.

In formula I and likewise in formulae I.A, I.B, I.C, I.A.a, I.B.a and I.C.a, the radical $R^3$ is in particular selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl.

In formula I and likewise in formulae I.A, I.B, I.C, I.A.a, I.B.a and I.C.a, the radical $R^3$ is especially hydrogen.

In formula I and likewise in formulae I.A, I.B, I.C, I.A.a, I.B.a and I.C.a, the radicals $R^4$ and $R^5$, independently of each other, are in particular selected from the group consisting of hydrogen, fluorine and $C_1$-$C_2$-alkyl, or the moiety C($R^4$, $R^5$)-A is a cyclopropane-1,2-diyl. In formula I and likewise in formulae I.A, I.B, I.C, I.A.a, I.B.a and I.C.a, the radicals $R^4$ and $R^5$, independently of each other, are more particularly selected from the group consisting of hydrogen, fluorine and methyl. In formula I and likewise in formulae I.A, I.B, I.C, I.A.a, I.B.a and I.C.a, the moiety C($R^4$,$R^5$) is especially CH$_2$ or CF$_2$.

In formula I and likewise in formulae I.A and I.A.a, the radicals $R^{y1}$ and $R^{y2}$, independently of each other, are in particular selected from the group consisting of hydrogen and fluorine. In formula I and likewise in formulae I.A and I.A.a, the moiety C($R^{y1}$,$R^{y2}$) is especially CH$_2$ or CF$_2$.

In formula I and likewise in formulae I.B and I.B.a, the radicals $R^{x1}$ and $R^{x2}$, independently of each other, are in particular selected from the group consisting of hydrogen and fluorine. In formula I and likewise in formulae I.B and I.B.a, the moiety C($R^{x1}$,$R^{x2}$) is especially CH$_2$ or CF$_2$.

In formula I and likewise in formulae I.A, I.B, I.C, I.A.a, I.B.a and I.C.a, the radical Het is in particular selected from the group consisting of C-bound 5- or 6-membered monocyclic hetaryl, which has 1 or 2 nitrogen atoms as ring members, benzofuryl and C-bound, 9- or 10-membered fused bicyclic hetaryl, which has 1 or 2 nitrogen atoms as ring members and optionally a further heteroatom selected from the group consisting of O, S and N as ring member, where monocyclic hetaryl, benzofuryl and bicyclic hetaryl may be unsubstituted or may carry 1, 2, 3 or 4 substituents $R^a$. More particularly, Het is selected from the group consisting of C-bound 5- or 6-membered monocyclic hetaryl, which has 1 or 2 nitrogen atoms as ring members, and C-bound, fused 9- or 10-membered bicyclic hetaryl, which has 1, 2 or 3 nitrogen atoms as ring members, monocyclic hetaryl and bicyclic hetaryl may be unsubstituted or may carry 1, 2, 3 or 4 substituents $R^a$. In particular Het is unsubstituted or carries 1 or 2 substituents $R^a$.

The radical Het in formulae I, I.A, I.B, I.C, I.A.a, I.B.a and I.C.a in particular has at least one imino-nitrogen as ring member, which is located in the position adjacent to the carbon atom which is bound to the moiety C($R^4$R$^5$). More particularly, Het has at least one imino-nitrogen as ring member, which is located in the position adjacent to the carbon atom which is bound to the moiety C($R^4$R$^5$) and is selected from the group consisting of C-bound 5- or 6-membered monocyclic hetaryl, which has 1 or 2 nitrogen atoms as ring members, and C-bound, fused 9- or 10-membered bicyclic hetaryl, which has 1, 2 or 3 nitrogen atoms as ring members, monocyclic hetaryl and bicyclic hetaryl may be unsubstituted or may carry 1, 2, 3 or 4 substituents $R^a$. In particular Het is unsubstituted or carries 1 or 2 substituents $R^a$.

In this context, $R^a$, if present, is in particular selected from the group consisting of halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl, and fluorinated $C_3$-$C_6$-cycloalkyl. In this regard, $R^a$ is especially selected from the group consisting of fluorine, chlorine, methyl, fluoromethyl, difluoromethyl, trifluoromethyl, methoxy, fluoromethoxy, difluoromethoxy, trifluoromethoxy, cyclopropyl and fluorinated cyclopropyl.

Especially, the radical Het in formulae I, I.A, I.B, I.C, I.A.a, I.B.a and I.C.a is selected from the group consisting of 2-pyridyl, 2-pyrimidinyl, 4-pyrimidinyl, 2-pyrazinyl, 3-pyridazinyl, 2-imidazolyl, 4-imidazolyl, 3-pyrazolyl, 2-thiazolyl, 4-thiazolyl, 2-quinolinyl, 3-isoquinolinyl, 2-quinazolinyl, 2-quinoxalinyl, 1,5-naphthyridin-2-yl, 1,8-naphthyridin-2-yl, benzothiazol-1-yl, benzoxazol-1-yl, benzimidazol-2-yl, 1-methylbenzimidazol-2-yl, imidazo[1,2-a]pyridine-2-yl, pyrrolo[2,3-b]pyridine-6-yl, thieno[3,2-b]pyridine-5-yl, imidazo-[2,1-b]-thiazol-6-yl and 1,2,4-triazolo[1,5-a]pyridine-2-yl, where the aforementioned radicals may carry 1, 2 or 3 radicals $R^a$ which are as defined above, and in particular selected from the group consisting of halogen, $C_1$-$C_4$-alkyl, $C_1$-$C_2$-fluoroalkyl, $C_1$-$C_4$-alkoxy, $C_1$-$C_2$-fluoralkoxy, $C_3$-$C_6$-cycloalkyl and fluorinated $C_3$-$C_6$-cycloalkyl and especially selected from the group consisting of selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

Apart from that, the variables R', $R^{C1}$, $R^{C2}$, $R^{C3}$, $R^{C4}$, $R^a$, $R^{aa}$, $R^{x1}$, $R^{x2}$, $R^{y1}$, $R^{y2}$, $R^b$, $R^c$, $R^d$, $R^e$, $R^f$, $R^g$, $R^h$, $R^{11}$, $R^{12}$, $R^{13}$, $R^{14}$, $R^{15}$, $R^{21}$, $R^{22}$, $R^{23}$, $R^{24}$, $R^{31}$, $R^{32}$, $R^{33}$, $R^{34}$, $R^{35}$ Z', $R^z$ and $R^{y'}$, particularly have, irrespectively of their occurrence and with regard to the formulae I, I.A, I.B, I.C, I.A.a, I.B.a and I.C.a and with regard to each of the above mentioned embodiments, groups of embodiments and particularly preferred embodiments one of the following meanings, if not stated otherwise:

R' is in particular hydrogen or $C_1$-$C_4$-alkyl, especially hydrogen, methyl, ethyl, n-propyl or isopropyl.

$R^{C1}$ is in particular selected from the group consisting of fluorine, chlorine, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)NH$_2$ and NH$_2$, or if $R^{C1}$ is bound to phenyl, two radicals $R^{C1}$ which are bound to adjacent carbon atoms or phenyl, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl. $R^{C1}$ is in particular selected from the group consisting of fluorine, chlorine, CN, methyl, difluoromethyl, trifluoromethyl, methoxy and NH$_2$.

$R^{C2}$ is in particular selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, where phenyl the saturated or aromatic heteromonocyclic radical is unsubstituted or carries 1, 2 or 3 radicals $R^{C4}$. $R^{C2}$ is especially phenyl, pyridyl, pyrimidinyl, 1-pyrazolyl, 1-imidazolyl, 1-piperidinyl, 1-piperazinyl, 4-methyl-1-piperazinyl or 4-morpholinyl.

$R^{C3}$ is in particular selected from the group consisting of $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)NH$_2$ and NH$_2$, especially from the group consisting of fluorine, chlorine, OH, CN, methyl, difluoromethyl, trifluoromethyl, methoxy, 2-methoxyethyl, C(O)NH$_2$, C(O)OCH$_3$ and NH$_2$, or, if $R^1$ is phenyl, two radicals $R^{C3}$ which are bound to adjacent carbon atoms, together with the phenyl ring to which they are bound, form a bicyclic heterocyclic radical, which is selected from 5- or 6-indolyl, 5- or 6-benzimidazolyl, 5- or 6-benzopyrazolyl, 5- or 6-benzotriazolyl, 5- or 6-benzofuranyl, 2,3-dihydrobenzofuran-5-yl, 2,3-dihydrobenzofuran-6-yl, 1,3-dihydroindol-2-on-5-yl, 1,3-dihydroindol-2-on-6-yl, 5- or 6-quinolinyl, 5- or 6-isoquinolinyl, 5- or 6-quinazolinyl, 2-amino-5-quinazolinyl, and 2-amino-6-quinazolinyl.

$R^{C4}$ is in particular selected from fluorine, chlorine, CN, methyl, difluoromethyl, trifluoromethyl, methoxy, OH and NH$_2$.

$R^a$ is in particular selected from the group consisting of halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl and fluorinated $C_3$-$C_6$-cycloalkyl and especially selected from the group consisting of selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

$R^{aa}$ is in particular selected from the group consisting of halogen, $C_1$-$C_4$-alkyl, $C_1$-$C_2$-fluoroalkyl, $C_1$-$C_4$-alkoxy, $C_1$-$C_2$-fluoroalkoxy, $C_3$-$C_6$-cycloalkyl, fluorinated $C_3$-$C_6$-cycloalkyl, phenyl, pyridyl, pyrimidinyl, imidazolyl, pyrazolyl and oxazolyl, and especially selected from the group consisting of selected from fluorine, chlorine, methyl, fluoromethyl, difluoromethyl, trifluoromethyl, methoxy, fluoromethoxy, difluoromethoxy, trifluoromethoxy, cyclopropyl, optionally substituted by 1, 2 or 3 methyl groups, and fluorinated cyclopropyl.

$R^{x1}$ and $R^{x2}$ are independently of each other in particular selected from hydrogen, fluorine and $C_1$-$C_2$-alkyl. In particular $R^{x1}$ and $R^{x2}$ are both hydrogen.

$R^{y1}$ and $R^{y2}$ are independently of each other in particular selected from hydrogen, fluorine and $C_1$-$C_2$-alkyl. In particular $R^{y1}$ and $R^{y2}$ are both hydrogen.

Y is in particular a bond, CH$_2$ or C(O);

$R^{C1}$ is in particular selected from the group consisting of fluorine, chlorine, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)NH$_2$ and NH$_2$, or if $R^{C1}$ is bound to phenyl, two radicals $R^{C1}$ which are bound to adjacent carbon atoms or phenyl, together with the phenyl ring to which they are bound, form a bicyclic heterocyclic radical, which is selected from 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

$R^{C2}$ is in particular selected from the group consisting of phenyl, $C_3$-$C_6$-cycloalkyl, optionally substituted by 1, 2, or 3 methyl groups, fluorinated $C_3$-$C_6$-cycloalkyl, and 5- or 6-membered saturated or aromatic heteromonocyclic radicals, having 1, 2 or 3 heteroatoms as ring members, which are selected from O, S and N, such as 1-piperidinyl, 1-piperazinyl, 4-methyl-1-piperazinyl, 4-morpholinyl, pyridyl, pyrimidinyl, 1-pyrazolyl, or 1-imidazolyl, where phenyl the saturated or aromatic heteromonocyclic radical are unsubstituted or carry 1, 2 or 3 radicals $R^{C4}$, which are as defined above and which are preferably selected from the group consisting of fluorine, chlorine, CN, methyl, difluoromethyl, trifluoromethyl, methoxy and $NH_2$.

$R^{C3}$ is in particular selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)O—$C_1$-$C_4$-alkyl, C(O)$NH_2$ and $NH_2$, especially from the group consisting of fluorine, chlorine, OH, CN, methyl, difluoromethyl, trifluoromethyl, methoxy, 2-methoxyethyl, C(O)$NH_2$, C(O)$OCH_3$ and $NH_2$, or, if $R^1$ is phenyl, two radicals $R^{C3}$ which are bound to adjacent carbon atoms, together with the phenyl ring to which they are bound, form a bicyclic heterocyclic radical, which is selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

$R^{C4}$ is in particular selected from fluorine, chlorine, CN, methyl, difluoromethyl, trifluoromethyl, methoxy, OH and $NH_2$.

$R^b$ is in particular hydrogen, $C_1$-$C_4$-alkyl or fluorinated $C_1$-$C_2$-alkyl;

$R^c$ and $R^d$ are, independently of each other, in particular selected from hydrogen, $C_1$-$C_2$-alkyl, $C_1$-$C_2$-alkoxy;

$R^e$ and $R^f$ are, independently of each other, in particular selected from hydrogen,
$C_1$-$C_2$-alkyl, hydroxyl-$C_1$-$C_2$-alkyl, $C_1$-$C_2$-alkoxy-$C_1$-$C_2$-alkyl;

$R^g$ is in particular in particular hydrogen or $C_1$-$C_4$-alkyl, in particular hydrogen or methyl, $R^h$ is in particular $C_1$-$C_4$-alkyl or fluorinated $C_1$-$C_2$-alkyl, in particular methyl or trifluoromethyl;

$R^{11}$, $R^{21}$, $R^{31}$, independently of each other, are in particular hydrogen, $C_1$-$C_2$-alkyl, $C_1$-$C_2$-fluoroalkyl, especially methyl, ethyl, difluoromethyl, trifluoromethyl, cyclopropyl, cyclobutyl or cyclopropylmethyl.

$R^{12}$, $R^{22}$, $R^{32}$, independently of each other, are in particular $C_1$-$C_4$-alkyl or $C_1$-$C_4$-fluoroalkyl, especially methyl, ethyl, difluoromethyl or trifluoromethyl.

$R^{13}$, $R^{23}$, $R^{33}$, independently of each other, are in particular hydrogen or $C_1$-$C_4$-alkyl, especially hydrogen, methyl, ethyl, propyl or isopropyl.

$R^{14}$, $R^{24}$, $R^{34}$, independently of each other, are in particular hydrogen or $C_1$-$C_4$-alkyl, especially hydrogen, methyl, ethyl, propyl or isopropyl.

$R^{13}$ and $R^{14}$, $R^{23}$ and $R^{24}$, $R^{34}$ and $R^{34}$, respectively, together with the nitrogen atom to which they are bound may also form a saturated N-bound heterocyclic radical, selected from the group consisting of pyrrolidin-1-yl, piperidin-1-yl, morpholin-4-yl, thiomorpholin-4-yl, piperazin-1-yl and 4-methylpiperazin-1-yl, where the 6 aforementioned heterocyclic radicals may carry 1, 2, 3 or 4 substituents, selected from methyl.

$R^{15}$, $R^{35}$, independently of each other, are in particular hydrogen or $C_1$-$C_4$-alkyl, especially hydrogen, methyl, ethyl or propyl or isopropyl.

$R^{y'}$ is in particular selected from the group consisting of hydrogen and methyl;

$R^z$ is in particular hydrogen or methyl;

$Z'$ is in particular a bond, $CH_2$ or $CH_2CH_2$.

Particular embodiment of the invention relates to the compounds of formula I, to the N-oxides, the prodrugs, the hydrates and the tautomers thereof and to the pharmaceutically suitable salts thereof, where the compounds of the formula I are selected from the group consisting of:

5-Methyl-7-morpholin-4-yl-2-(2-quinolin-2-yl-ethyl)-5H-pyrrolo[3,4-c]pyridine-1,3,6-trione, 5-Methyl-7-(4-methyl-piperazin-1-yl)-2-(2-quinolin-2-yl-ethyl)-5H-pyrrolo[3,4-c]pyridine-1,3,6-trione, 5-Methyl-7-(1,1-dioxo-thiomorpholin-4-yl)-2-(2-quinolin-2-yl-ethyl)-5H-pyrrolo[3,4-c]pyridine-1,3,6-trione, 5-Methyl-7-(4-pyridyl)-2-(2-quinolin-2-yl-ethyl)-5H-pyrrolo[3,4-c]pyridine-1,3,6-trione, 5-Methyl-7-morpholin-4-yl-2-(2-[1,2,4]triazolo[1,5-a]pyridin-2-yl-ethyl)-5H-pyrrolo[3,4-c]pyridine-1,3,6-trione, 5-Methyl-7-morpholin-4-yl-2-(2-quinolin-2-yl-ethyl)-1,2-dihydro-5H-pyrrolo[3,4-c]pyridine-3,6-dione, 5-Methyl-7-(4-methyl-piperazin-1-yl)-2-(2-quinolin-2-yl-ethyl)-1,2-dihydro-5H-pyrrolo[3,4-c]pyridine-3,6-dione, 5-Methyl-7-pyridin-4-yl-2-(2-quinolin-2-yl-ethyl)-1,2-dihydro-5H-pyrrolo[3,4-c]pyridine-3,6-dione, 5-Methyl-7-morpholin-4-yl-2-(2-quinolin-2-yl-ethyl)-3,5-dihydro-2H-pyrrolo[3,4-c]pyridine-1,6-dione, 5-Methyl-7-(4-methyl-piperazin-1-yl)-2-(2-quinolin-2-yl-ethyl)-3,5-dihydro-2H-pyrrolo[3,4-c]pyridine-1,6-dione, 5-Methyl-7-pyridin-4-yl-2-(2-quinolin-2-yl-ethyl)-3,5-dihydro-2H-pyrrolo[3,4-c]pyridine-1,6-dione, 5-Methyl-7-(1,1-dioxo-thiomorpholin-4-yl)-2-(2-quinolin-2-yl-ethyl)-3,5-dihydro-2H-pyrrolo[3,4-c]pyridine-1,6-dione, 5-Methyl-7-pyridin-3-yl-2-(2-quinolin-2-yl-ethyl)-3,5-dihydro-2H-pyrrolo[3,4-c]pyridine-1,6-dione, 5-(4-Methoxy-benzyl)-7-morpholin-4-yl-2-(2-quinolin-2-yl-ethyl)-3,5-dihydro-2H-pyrrolo[3,4-c]pyridine-1,6-dione, 7-Morpholin-4-yl-2-(2-quinolin-2-yl-ethyl)-3,5-dihydro-2H-pyrrolo[3,4-c]pyridine-1,6-dione, 5-Ethyl-7-morpholin-4-yl-2-(2-quinolin-2-yl-ethyl)-3,5-dihydro-2H-pyrrolo[3,4-c]pyridine-1,6-dione, 5-Isopropyl-7-morpholin-4-yl-2-(2-quinolin-2-yl-ethyl)-3, 5-dihydro-2H-pyrrolo[3,4-c]pyridine-1,6-dione, 5-(2-Methoxy-ethyl)-7-morpholin-4-yl-2-(2-quinolin-2-yl-ethyl)-3,5-dihydro-2H-pyrrolo[3,4-c]pyridine-1,6-dione, 5-(2-Hydroxy-ethyl)-7-morpholin-4-yl-2-(2-quinolin-2-yl-ethyl)-3,5-dihydro-2H-pyrrolo[3,4-c]pyridine-1,6-dione, 5-Methyl-2-[2-(1-methyl-1H-benzoimidazol-2-yl)-ethyl]-7-morpholin-4-yl-3,5-dihydro-2H-pyrrolo[3,4-c]pyridine-1,6-dione, 5-Methyl-2-[2-(1-methyl-1H-benzoimidazol-2-yl)-ethyl]-7-pyridin-3-yl-3,5-dihydro-2H-pyrrolo[3,4-c]pyridine-1,6-dione, 2-(2-Imidazo[1,2-a]pyridin-2-yl-ethyl)-5-methyl-7-morpholin-4-yl-3,5-dihydro-2H-pyrrolo[3,4-c]pyridine-1,6-dione, 2-(2-Imidazo[1,2-a]pyridin-2-yl-ethyl)-5-methyl-7-morpholin-4-yl-3,5-dihydro-2H-pyrrolo[3,4-c]pyridine-1,6-dione, 5-Methyl-7-morpholin-4-yl-2-(2-[1,2,4]triazolo[1,5-a]pyridin-2-yl-ethyl)-3,5-dihydro-2H-pyrrolo[3,4-c]pyridine-1, 6-dione, 5-Methyl-7-morpholin-4-yl-2-[2-(5,6,7,8-tetrahydro-[1,2,4]triazolo[1,5-a]pyridin-2-yl)-ethyl]-3,5-dihydro-2H-pyrrolo[3,4-c]pyridine-1,6-dione, 5-Methyl-7-pyridin-3-yl-2-(2-[1,2,4]triazolo[1,5-a]pyridin-2-yl-ethyl)-3,5-dihydro-2H-pyrrolo[3,4-c]pyridine-1,6-dione, 7-(4-Fluoro-phenyl)-5-methyl-2-(2-quinolin-2-yl-ethyl)-3,5-dihydro-2H-pyrrolo[3,4-c]pyridine-1,6-dione, 5-Methyl-7-pyrimidin-5-yl-2-(2-quinolin-2-yl-ethyl)-3,5-dihydro-2H-pyrrolo[3,4-c]pyridine-1,6-dione, 5-Methyl-7-(1H-pyrazol-4-yl)-2-(2-quinolin-2-yl-ethyl)-3,5-dihydro-2H-pyrrolo[3,4-c]pyridine-1,6-dione, 5-Methyl-7-(2-methyl-2H-pyrazol-3-yl)-2-(2-quinolin-2-yl-ethyl)-3,5-dihydro-2H-pyrrolo[3,4-c]pyridine-1,6-dione, 7-(4-Methoxy-phenyl)-5-methyl-2-(2-quinolin-2-yl-ethyl)-3,5-dihydro-2H-pyrrolo[3,4-c]pyridine-1,6-dione, 2-[2-(1,3-benzothiazol-2-yl)ethyl]-5-methyl-7-(4-pyridyl)-3,5-dihydro-2H-pyrrolo[3,4-c]pyridine-1,6-dione, 2-[2-(1,3-benzothiazol-2-yl)ethyl]-5-methyl-7-morpholin-4-yl-3,5-dihydro-2H-pyrrolo[3,4-c]pyridine-1,6-dione, 2-(2,2-Difluoro-2-quinolin-2-yl-ethyl)-5-methyl-7-morpholin-4-yl-3,5-dihydro-2H-pyrrolo[3,4-c]pyridine-1,6-dione and 3,3-Difluoro-5-methyl-7-morpholin-4-yl-2-(2-quinolin-2-yl-ethyl)-3,5-dihydro-2H-pyrrolo[3,4-c]pyridine-1,6-dione.

The compounds of the invention of the general formula I and the starting materials used to prepare them can be prepared in analogy to known processes of organic chemistry as are described in standard works of organic chemistry, e.g. Houben-Weyl, "Methoden der Organischen Chemie", Thieme-Verlag, Stuttgart, Jerry March "Advanced Organic Chemistry", 5$^{th}$ edition, Wiley & Sons and the literature cited therein, and R. Larock, "Comprehensive Organic Transformations", 2$^{nd}$ edition, Weinheim, 1999 and the literature cited therein. The compounds of the invention of the general formula I are advantageously prepared by the methods described below and/or in the experimental section.

Compounds of the formula I, wherein Q is oxygen, can be prepared e.g. by reacting a compound of the formula II

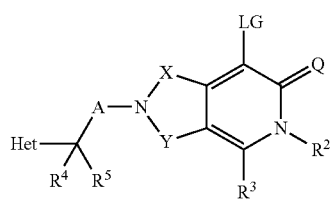
(II)

wherein Het, A, X, Y, R$^2$, R$^3$, R$^4$ and R$^5$ are as defined for formula I, LG is a leaving group such as chlorine, bromine or iodine;

with a compound of formula III,

M-Z—R$^1$     (III)

where Z is in particular CH$_2$, 1,2-ethanediyl, 1,2-ethenediyl or 1,2-ethynediyl or especially a bond, and R$^1$ has one of the meanings given herein; wherein M is a Li, B(OR$^{B1}$)(OR$^{B2}$) radical or an Sn(R$^{Sn}$)$_3$ radical, where R$^{B1}$ and R$^{B2}$ are, independently of each other, hydrogen or C$_1$-C$_4$-alkyl or R$^{B1}$ and R$^{B2}$ together form a C$_2$-C$_6$-alkanediyl moietyl, e.g. ethane-1,2-diyl, propane-1,3-diyl or 1,1,2,2-tetramethylethane-1,2-diyl, and wherein R$^{Sn}$ is C$_1$-C$_6$-alkyl, C$_3$-C$_6$-cycloalkyl or phenyl.

Amongst the compounds of formula III, particular preference is given to the compounds of formula IIIa and, if R$^{B1}$ and R$^{B2}$ are hydrogen, the trimers thereof

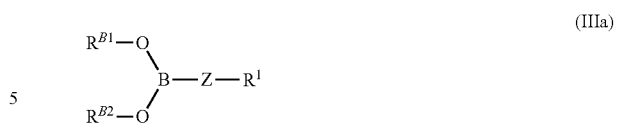
(IIIa)

The reaction of the compound II with the compound III or IIIa, respectively, can be performed by analogy to known coupling reactions in the presence of suitable transition metal catalysts, in particular palladium catalysts. Typical reactions conditions are those of Stille coupling (see e.g. Stille et al. Angew. Chem. Int. Ed. Engl. 1986, 25, 508; J. Eluguero et al.; Synthesis 1997, 5, 563-566) or Suzuki coupling (see e.g. A. Suzuki et al, Chem. Rev. 1995, 95, 2457-2483, N. Zhe et al.; J. Med. Chem. 2005, 48 (5), 1569-1609; Young et al.; J. Med. Chem. 2004, 47 (6), 1547-1552; C. Slee et al.; Bioorg. Med. Chem. Lett. 2001, 9, 3243-3253).

In a similar manner, compounds of the formula I, where Z is NH or O, as well as compounds of the formula I, were R$^1$ is an N-bound heterocycle and Z is a single bond, can be prepared by reacting a compound of the formula II, as defined above, with a compound of the formula III'

H—Z—R$^1$     (III')

The reaction of compound II with compound III' is preferably carried out in an aprotic solvent, such as dimethylsulfoxide, acetonitrile, N-methylpyrrolidone, dimethylformamide, dimethylacetamide, tetramethyl urea, or mixtures thereof or mixtures thereof with halogenated hydrocarbons such as dichloromethane. The reaction is preferably carried out in the presence of a suitable base, e.g. an alkalimetal carbonate such as lithium carbonate, sodium carbonate, potassium carbonate or caesium carbonate or an alkalimetal alkoxide.

Compounds of the formula I, where Q is O, can also be prepared e.g. by reacting a compound of the formula IIa

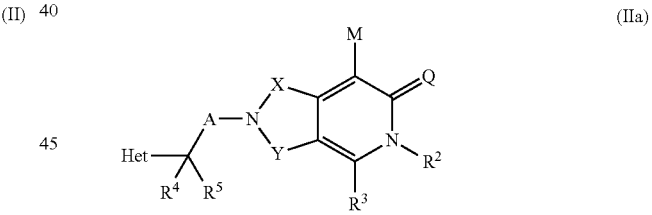
(IIa)

wherein Het, A, X, Y, R$^2$, R$^3$, R$^4$ and R$^5$ are as defined for formula I, and M is a metal or semi-metal containing moiety as defined for formula III and M is in particular Li, MgHal' or ZnHal' or a B(OR$^{B1}$)(OR$^{B2}$) radical;

with a compound of formula IIIb or IIIc,

Hal-Z—R$^1$     (IIIb)

H—Z—R$^1$     (IIIc)

where Z and R$^1$ are as defined herein and where Z in formula IIIb is in particular a single bond, CH$_2$, 1,2-ethanediyl, ethenediyl and where Z in formula IIIc is in particular a single bond or ethynediyl, and wherein Hal is bromine or iodine.

The reaction of the compound IIa with the compound Ma or IIIb can be performed by analogy to the reaction of compound II with compound III.

The compounds II and IIa, are known or can be prepared by standard methods of organic chemistry. Compounds of the formula IIa can be prepared from compounds of the formula II by a halogen metal exchange, optionally followed by transmetallation reaction.

Compounds of the formula I, where Z—$R^1$ is a N-bound radical can be obtained by a coupling reaction between the compound II and the corresponding amine in the presence of a palladium catalyst in terms of a Buchwald-Hartwig reaction. Suitable palladium catalyst are for example tris-(dibenzylideneacetone)dipalladium(0) ($Pd_2(dba)_3$), [1,1-bis(diphenylphosphino)ferrocene]dichloropalladium(II) ($PdCl_2$ (dppf)) or palladium acetate ($Pd(OAc)_2$). The reaction is usually carried out in the presence of a tri(substituted)phosphine, e.g. a triarylphosphine such as triphenylphosphine, tritolylphosphine or 2,2'-bis(diphenylphosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base such as an alkaline alkoxide, earth alkine alkoxide, alkaline carbonate or earth alkaline carbonate such as or sodium tert-butoxide or cesium carbonate.

Compounds of the formula I and likewise compounds of the formula II can be prepared by reacting a compound of the formula IV or IV' with an amine compound of the formula V:

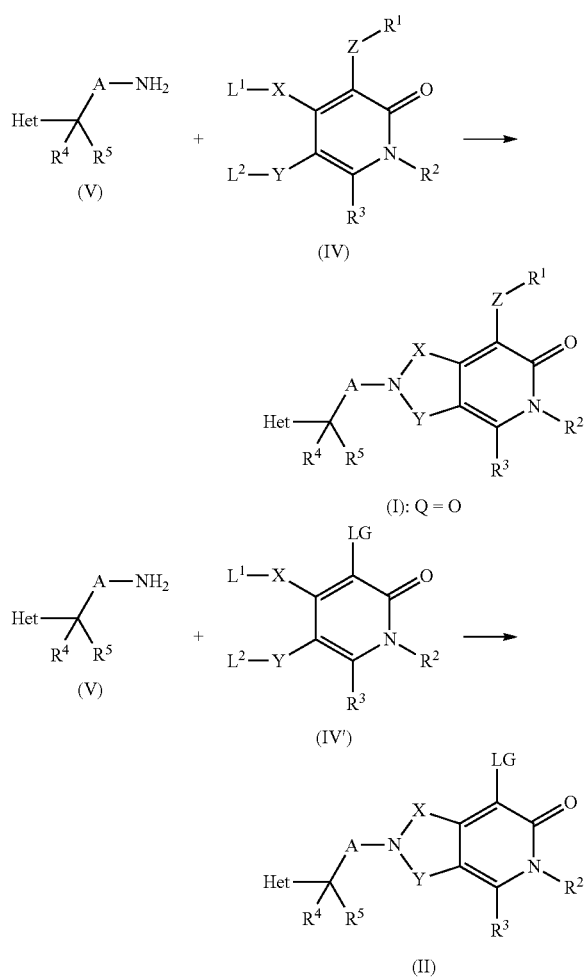

In the above schemes Het, LG, A, X, Y, Z, $R^1$, $R^2$, $R^3$, $R^4$ and $R^5$ are as defined above, $L^1$ is halogen or $C_1$-$C_4$-alkoxy, e.g. methoxy or ethoxy, if X is C(O) or $L^1$ is a suitable leaving group, e.g. chlorine, bromine, alkylsulfonyloxy such as methan-sulfonyloxy or arylsulfonyloxy such as phenylsulfonyloxy or p-tolylsulfonyloxy, if X is C($R^{x1}$,$R^{x2}$), and $L^2$ is halogen or $C_1$-$C_4$-alkoxy, e.g. methoxy or ethoxy, if X is C(O) or $L^2$ is a suitable leaving group, e.g. chlorine, bromine, alkylsulfonyloxy such as methan-sulfonyloxy or arylsulfonyloxy such as phenylsulfonyloxy or p-tolylsulfonyloxy, if Y is C($R^{y1}$,$R^{y2}$). Suitable reaction conditions are given in the examples. $R^{x1}$, $R^{x2}$, $R^{y1}$ and $R^{y2}$ are as defined above.

Compounds of the formulae I and II, where X is C(O) and Y is $CH_2$ can be prepared from compounds of the formulae I and II, respectively, where both X and Y are C(O), by selective reduction, e.g. by first reacting the compounds of formula I, where both X and Y are C(O), with Lawesson's reagent to obtain a compound of formula I or II, where X is C(O) and Y is C(S), followed by treatment with a suitable reducing agent such as Raney nickel. Similarly, compounds of the formulae I and II, where Y is C(O) and X is $CH_2$ can be prepared from compounds of the formulae I and II, respectively, where both X and Y are C(O), by selective reduction, e.g. by first reacting the compounds of formula I, where both X and Y are C(O), with zinc in acetic acid to obtain a compound of formula I or II, where X is CHOH and Y is C(O), followed by treatment with a trialkylsilane in the presence of a Lewis acid such as $BF_3$-etherate or by direct reduction with Zn in acetic acid.

Apart from that, compounds of the formula I and likewise compounds of the formula II, where X or Y are $CF_2$ can be prepared by successively reacting compounds of the formulae I and II, where both X or Y are C=O with a suitable sulfurizing agent, such as Laweson's reagent or $P_2S_5$, obtain a compound of the formula I or II, where one of X and Y is C(=S) and then reacting the obtained thio-compound with a suitable fluorinating agent, e.g. HF or HF adduct of tetraalkylamonium fluoride in the presence of N-bromosuccinimide [Tet. Lett. 35(23), 3983-4 (1994)].

Apart from that, compounds of the formula I and likewise compounds of the formula II, where Q is S can be prepared by successively reacting compounds of the formulae I and II, where Q is O with a suitable sulfurizing agent, such as Laweson's reagent or $P_2S_5$.

The N-oxides of compound I may be prepared from the compounds of formula I according to conventional oxidation methods, for example by treating said compounds with an organic peracid; such as metachloroperbenzoic acid or 3-chloroperbenzoic acid [Journal of Medicinal Chemistry 38(11), 1892-1903 (1995), WO 03/64572]; or with inorganic oxidizing agents; such as hydrogen peroxide [cf. Journal of Heterocyclic Chemistry 18 (7), 1305-1308 (1981)] or oxone [cf. Journal of the American Chemical Society 123(25), 5962-5973 (2001)]. The oxidation may lead to pure mono-N-oxides or to a mixture of different N-oxides, which can be separated by conventional methods; such as chromatography.

The compounds of the formulae III, III', IIIa, IIIb, IIIc, IV, IV' and V are well known in the art or can be prepared by analogy to well established reactions of organic synthetic chemistry or by analogy to the methods as described in standard works of organic chemistry, e.g. Houben-Weyl, "Methoden der Organischen Chemie", Thieme-Verlag, Stuttgart, Jerry March "Advanced Organic Chemistry", $5^{th}$ edition, Wiley & Sons and the literature cited therein, and R. Larock, "Comprehensive Organic Transformations", $2^{nd}$ edition, Weinheim, 1999 and the literature cited therein. The reactions are usually performed in an organic solvent, including aprotic organic solvent, e.g. substituted amides, lactames and ureas; such as dimethylformamide, dimethylacetamide, N-methylpyrrolidone, tetramethyl urea, cyclic ethers; such as dioxane, tetrahydrofurane, halogenated hydrocarbons; such as dichloromethane, and mixtures thereof as well as mixtures thereof with $C_1$-$C_6$-alkanols and/or water.

The reactions described above will be usually performed at temperatures ranging from −10° C. to 100° C., depending on the reactivity of the used compounds.

The reaction mixtures are worked up in a conventional way, e.g. by mixing with water, separating the phases and, where appropriate, purifying the crude products by chromatography. The intermediates and final products in some cases result in the form of colorless or pale brownish, viscous oils which are freed of volatiles or purified under reduced pressure and at moderately elevated temperature. If the intermediates and final products are obtained as solids, the purification can also take place by recrystallization or digestion.

Due to their capability of inhibiting PDE10A at low concentrations, the compounds of the formula I, their N-oxides, their hydrates, their tautomers and their prodrugs and the pharmaceutically acceptable salts thereof, are particularly suitable for treating disorders or conditions, which can be treated by inhibition of phosphodiesterase type 10A. The terms "treating" and "treatment" in terms of the present invention have to be understood to include both curative treatment of the cause of a disease or disorder, the treatment of the symptoms associated with a disease or disorder, i.e. controlling the disease or disorder or ameliorating the conditions or symptoms associated with a disease or disorder, and prophylactic treatment, i.e. a treatment for reducing the risk of a disease or disorder.

Neurological and psychiatric disorders or conditions which can be treated by inhibition of PDE10A, including curative treatment, control or amelioration and prophylaxis, include CNS disorders, in particular schizophrenia, depression, bipolar disorders, cognitive dysfunctions associated with schizophrenia, cognitive dysfunctions associated with Alzheimer's disease, Huntington's disease (Huntington chorea), anxiety and substance-related disorders, especially substance use disorder, substance tolerance conditions associated with substance withdrawal. Disorders or conditions which can be treated by inhibition of PDE10A, including curative treatment, control or amelioration and prophylaxis, also include treatment of diet induced obesity.

Thus, the invention relates to the use of compounds of formula I, their N-oxides, their hydrates, their tautomers and their prodrugs and the pharmaceutically acceptable salts thereof, for treatment of disorders or conditions, which can be treated by inhibition of phosphodiesterase type 10A, i.e. the invention relates to the use of such compounds for curative treatment of such a disease or disorder, controlling such a disease or disorder, ameliorating the symptoms associated with such a disease or disorder and reducing the risk for such a disease or disorder.

The present invention also relates to a method for the treatment of a medical disorder, selected from neurological and psychiatric disorders which can be treated by inhibition of phosphodiesterase type 10A, said method comprising administering an effective amount of at least one compound, selected from the group of compounds of formula I, their N-oxides, their hydrates, their tautomers, their prodrugs and the pharmaceutically acceptable salts thereof, to a mammal in need thereof.

The present invention in particular relates to:
a method for treating, controlling, ameliorating or reducing the risk of schizophrenia in a mammalian;
a method for treating, controlling, ameliorating or reducing the risk of cognitive disturbances associated with schizophrenia in a mammalian;
a method for treating, controlling, ameliorating or reducing the risk of depression in a mammalian;
a method for treating, controlling, ameliorating or reducing the risk of bipolar disorders in a mammalian;
a method for treating or ameliorating the symptoms associated with substance use disorders in a mammalian;
a method for treating or ameliorating the symptoms associated with diet-induced obesity in a mammalian;
a method for treating, controlling, ameliorating or reducing the risk of cognitive disturbances associated with Alzheimer's disease in a mammalian;
a method for treating, controlling, ameliorating or reducing the risk of behavioral symptoms in Alzheimer's disease;
a method for treating, controlling, ameliorating or reducing the risk of anxiety in a mammalian;
a method for treating, controlling, ameliorating or reducing the risk of Huntington's disease in a mammalian;
which methods comprising administering an effective amount of at least one compound, selected from the group of compounds of formula I, their N-oxides, their hydrates, their tautomers, their prodrugs and the pharmaceutically acceptable salts thereof, to a mammal in need thereof.

The subject treated in the present methods is generally a mammal, preferably a human being, male or female, in whom inhibition of PDE10A is desired. The terms "effective amount" and "therapeutically effective amount" mean the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes, wherein there may be a slowing, interrupting, arresting, controlling, or stopping of the progression of the disorders described herein, but does not necessarily indicate a total elimination of all disorder symptoms, as well as the prophylactic therapy of the mentioned conditions, particularly in a patient who is predisposed to such disease or disorder. The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of and or "administering a" compound should be understood to mean providing a compound of the invention or a prodrug of a compound of the invention to the individual in need of treatment.

A preferred embodiment of the present invention provides a method for treating schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating cognitive disturbances associated with schizophrenia, comprising: administering to a patient in need thereof an effective amount of at least one compound, selected from the group of compounds of formula I, their N-oxides, their hydrates, their tautomers, their prodrugs and the pharmaceutically acceptable salts thereof.

At present, the fourth edition of the Diagnostic and Statistical Manual of Mental Disorders (DSM-IV) (1994, American Psychiatric Association, Washington, D.C.), provides a diagnostic tool including schizophrenia and other psychotic disorders. These include: disorders having psychotic symptoms as the defining feature. The term psychotic refers to delusions, prominent hallucinations, disorganized speech, disorganized or catatonic behavior. The disorder includes: paranoid, disorganized, catatonic, undifferentiated, and residual schizophrenia, schizophreniform disorder, schizoaffective disorder, delusional disorder, brief psychotic disorder, shared psychotic disorder, psychotic disorder due to a general medical condition, substance-induced psychotic disorder, and psychotic disorder not otherwise specified. The skilled artisan will recognize that there are alternative nomenclatures, nosologies, and classification systems for neurological and psychiatric disorders, and particular schizophrenia, and that these systems evolve with medical scientific progress. Thus, the term "schizophrenia" is intended to include like disorders that are described in other diagnostic sources.

In another preferred embodiment, the present invention provides a method for treating substance-related disorders, comprising: administering to a patient in need thereof an effective amount of at least one compound, selected from the group of compounds of formula I, their N-oxides, their hydrates, their tautomers, their prodrugs and the pharmaceutically acceptable salts thereof.

In another preferred embodiment, the present invention provides a method for treating anxiety, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein the term "anxiety" includes treatment of those anxiety disorders and related disorder as described in the DSM-IV. The skilled artisan will recognize that there are alternative nomenclatures, nosologies, and classification systems for neurological and psychiatric disorders, and particular anxiety, and that these systems evolve with medical scientific progress. Thus, the term "anxiety" is intended to include like disorders that are described in other diagnostic sources.

In another preferred embodiment, the present invention provides a method for treating depression, comprising: administering to a patient in need thereof an effective amount of at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including depression and related disorders. Depressive disorders include, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder. As used herein the term "depression" includes treatment of those depression disorders and related disorder as described in the DSM-IV.

In another preferred embodiment, the present invention provides a method for treating substance-related disorders, especially substance dependence, substance abuse, substance tolerance, and substance withdrawal, comprising: administering to a patient in need thereof an effective amount at least one compound, selected from the group of compounds of formula I, their N-oxides, their hydrates, their tautomers, their prodrugs and the pharmaceutically acceptable salts thereof. At present, the fourth edition of the Diagnostic and Statistical Manual of Mental Disorders (DSM-IV) (1994, American Psychiatric Association, Washington, D.C.), provides a diagnostic tool including disorders related to taking a drug of abuse (including alcohol), to the side effects of a medication, and to toxin exposure. Substances include alcohol, amphetamine and similarly acting sympathomimetics, caffeine, cannabis, cocaine, hallucinogens, inhalants, nicotine, opioids, phencyclidine (PCP) or similarly acting arylcyclohexylamines, and sedatives, hypnotics, or anxiolytics. Also, polysubstance dependence and other unknown substance-related disorders are included. The skilled artisan will recognize that there are alternative nomenclatures, nosologies, and classification systems for neurological and psychiatric disorders, and particular substance-related disorders, and that these systems evolve with medical scientific progress. Thus, the term "substance-related disorder" is intended to include like disorders that are described in other diagnostic sources.

In the treatment, prevention, control, amelioration, or reduction of risk of conditions which require inhibition of PDE10A an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. When treating, preventing, controlling, ameliorating, or reducing the risk of neurological and psychiatric disorders or other diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams, in the case of a 70 kg adult human, the total daily dose will generally be from about 7 milligrams to about 350 milligrams. This dosage regimen may be adjusted to provide the optimal therapeutic response. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be administered by conventional routes of administration, including parenteral (e.g., intramuscular, intrapentoneal, intravenous, ICV, intracisternal injection or infusion, subcutaneous injection, or implant), oral, by inhalation spray, nasal, vaginal, rectal, sublingual, or topical routes of administration.

The compounds according to the present invention are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The present invention also relates to pharmaceutical compositions (i.e. medicaments) which comprise at least one compound of the present invention and, where appropriate, one or more suitable excipients.

These excipients/drug carriers are chosen according to the pharmaceutical form and the desired mode of administration.

The compounds of the present invention can be used to manufacture pharmaceutical compositions for parenteral (e.g., intramuscular, intrapentoneal, intravenous, ICV, intracisternal injection or infusion, subcutaneous injection, or implant), oral, sublingual, intratracheal, intranasal, topical, transdermal, vaginal or rectal administration, and be administered to animals or humans in unit dose forms, mixed with conventional pharmaceutical carriers, for the prophylaxis or treatment of the above impairments or diseases.

In the pharmaceutical compositions, the at least one compound of the present invention may be formulated alone or together with further active compounds, in suitable dosage unit formulations containing conventional excipients, which generally are non-toxic and/or pharmaceutically acceptable. Carriers or excipients can be solid, semisolid or liquid materials which serve as vehicles, carriers or medium for the active compound. Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Kantor-Verlag, 1996.

Suitable unit dose forms include forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

If a solid composition is prepared in the form of tablets, the main ingredient is mixed with a pharmaceutical carrier such as gelatin, starch, lactose, magnesium stearate, talc, silicon dioxide or the like.

The tablets may be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active ingredient with an extender and taking up the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable coloring.

The water-dispersible powders or granules may comprise the active ingredients mixed with dispersants, wetting agents or suspending agents such as polyvinylpyrrolidones, and sweeteners or taste improvers.

Rectal administration is achieved by the use of suppositories which are prepared with binders which melt at the rectal temperature, for example cocobutter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The active basic ingredient may also be formulated as microcapsules or liposomes/centrosomes, if suitable with one or more carriers or additives.

In addition to the compounds of the general formula I, their prodrugs, their N-oxides, their tautomers, their hydrates or their pharmaceutically suitable salts, the compositions of the invention may comprise further active basic ingredients which may be beneficial for the treatment of the impairments or diseases indicated above.

The present invention thus further relates to pharmaceutical compositions in which a plurality of active basic ingredients are present together, where at least one thereof is a compound of the invention.

When producing the pharmaceutical compositions, the compounds according to the invention are optionally mixed or diluted with one or more carriers.

The compounds of the invention also include those compounds in which one or more atoms have been replaced by their stable, non-radioactive isotopes, for example, a hydrogen atom by deuterium.

Stable isotopes (e.g., deuterium, $^{13}C$, $^{15}N$, $^{18}O$) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labelling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labelled molecule are different from those of the unlabelled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behaviour of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labelled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The following examples are intended for further illustration of the present invention.

Abbreviations which have been used in the descriptions of the schemes and the Examples that follow are: $BF_3.OEt_2$ for boron trifluoride etherate; $BH_3$-THF for borane tetrahydrofuran complex; $Cs_2CO_3$ for caesium carbonate; $CHCl_3$ for chloroform; DCM for dichloromethane; DEAD for diethyl azodicarboxylate; DIAD for diisopropyl azodicarboxylate; DIPEA for N,N-diisopropylethylamine; DME for dimethoxyethane; DMF for dimethylformamide; DMSO for dimethylsulfoxide; EA for ethyl acetate; Et for ethyl; EtOH for ethanol; EX. for EXAMPLE; HCl for hydrochloric acid; HMPA for hexamethylphosphoramide; i-Pr for isopropyl; $K_2CO_3$ for potassium carbonate; Lawesson's reagent for 2,4-bis(4-methoxyphenyl)-1,3,2,4-dithiadiphosphetane-2,4-dithione; MeCN for acetonitrile; MeOH for methanol; $NaBH_4$ for sodium borohydride; PE for petroleum ether; $Pd_2(dba)_3$ for tris (dibenzylideneacetone)dipalladium(0); $PdCl_2$(dppf) for 1,1'-bis(diphenylphosphino)ferrocene-palladium (II)-dichloride; PMB for 4-methoxybenzyl; PyBOP for benzotriazol-1-yl-oxytripyrrolidinophosphonium hexafluorophosphate; $R_t$ for retention time; r.t. for room temperature, $SOCl_2$ for thionyl chloride; TEA for triethylamine; TFA for trifluoroacetic acid; THF for tetrahydrofuran; TMSCl for trimethylsilyl chloride; Xantphos for 4,5-Bis(diphenylphosphino)-9,9-dimethylxanthene.

LC-MS measurements were run on Agilent 1200 HPLC/6100 SQ System.

PREPARATION EXAMPLES

I. Preparation of Intermediates

The starting materials used in the examples are either commercially available or can be synthesized by the average skilled person trained in organic chemistry following routine laboratory practice as outlined, for example in the examples below.

a) Preparation of Compounds of the General Formula Het-$CR^4R^5$-A-$NH_2$ a1) 2-Quinolin-2-yl-ethanamine a1.1) Quinolin-2-yl-acetic acid ethyl ester To a suspension of vacuum dried Zn dust (6.0 g, 93.8 mmol) in dry THF (100 ml) was added TMSCl (0.5 ml) dropwise over 5 min under $N_2$ atmosphere and under stirring. The mixture was stirred for 30 min and warmed to 45° C. Ethyl bromoacetate (5.2 ml, 46.9 mmol) was added dropwise via a syringe. After addition, the mixture was stirred at the same temperature for 1 h. After sedation at r. t. for 2 h, a clear orange solution was formed. The orange solution (50 ml) was carefully sucked into a syringe through a long needle and added to a mixture of 2-bromoquinoline (2.0 g, 9.6 mmol) and $PdCl_2$(dppf) (200 mg, 0.27 mmol) in a three-neck flask. The mixture was refluxed under $N_2$ for 3 h. The reaction was monitored with LC-MS. Ethyl acetate (200 ml) was added to dilute the mixture and water (50 ml) was added to quench the reaction. The mixture was filtered through a celite pad. The filtration was partitioned between brine and ethyl acetate. The organic layer was separated, washed with brine (100 ml), dried over sodium sulfate and concentrated. The residue was purified with silica column (PE/EA=3: 1) to give the title compound as orange oil (1.0 g, 48%). LC-MS (ESI+): m/e 216 (M+H)$^+$, $R_t$: 0.62 min.

a1.2) 2-Quinolin-2-yl-ethanol

To a cold (0° C.) solution of the compound from Example a1.1 (10 g, 45 mmol) in THF (200 ml) was added LiAlH$_4$ (2.65 mg, 70 mmol) in small portions over a period of 5 min. The resulting mixture was stirred for 1 h. Water was added dropwise very slowly. Then more water and EA were added. The organic phase was collected, dried and concentrated. The residue was purified by silica gel chromatography (PE/EA=2: 1) to give the title compound as a yellow solid (2.5 g, 30%). LC-MS (ESI+): m/e 174 (M+H)$^+$, $R_t$: 0.75 min.

a1.3) 1-Succinimidyl-2-quinolin-2-yl-ethane

The compound from Example a1.2 (2.5 g, 15 mmol), pyrrolidine-2,5-dione (2 g, 20 mmol) and PPh$_3$ (5.25 g, 20 mmol) were dissolved in THF (50 ml). The solution was added DEAD (6.1 g, 35 mmol). The mixture was stirred at r.t. overnight. The solvent was evaporated and the residue was purified by silica gel chromatography (PE/EA=2/1) to get the title compound as yellow oil (2.5 g, 66%). LC-MS (ESI+): m/e 255 (M+H)+, $R_t$: 1.15 min.

a1.4) 2-Quinolin-2-yl-ethanamine

A flask was charged with the compound from Example a1.3 (2.5 g, 20 mmol) and methanol (50 ml). To the mixture was added aqueous hydrazine (85%, 25 ml). The solution was stirred at reflux overnight. The solvent was evaporated and the residue was purified by silica gel chromatography (DCM/MeOH=10/1) to give the title compound as yellow solid (1.5 g, 43%). LC-MS (ESI+): m/e 173 (M+H)+, $R_t$: 1.42 min.

a2) 2-Quinolin-2-yl-ethanamine a2.1) 2-(Chloromethyl)quinoline

To a suspension of 2-(chloromethyl)quinoline hydrochloride (10 g, 46.7 mmol) in EA/water (150 ml: 75 ml) was added sodium hydrogencarbonate powder portionwise until gas evolution ceased. The organic layer was collected, washed with brine (3×50 ml), dried over sodium sulfate and concentrated. The obtained crude title compound was used in without further purification (8 g, 96% yield).

LC-MS (ESI+): m/e 178 (M+H)+, $R_t$: 1.79 min.

a2.2) 2-(Cyanomethyl)quinoline 2-(Chloromethyl)quinoline (41.2 g, 232 mmol, see Example a2.1)) was dissolved in a mixture of EtOH/water (200 ml: 100 ml). Sodium cyanide (11.48 g, 234 mol) was added. The mixture was heated to 50° C. and stirred overnight. Ethanol was removed under reduced pressure. The residue was extracted with EA (3×200 ml). The remaining aqueous phase was treated with 1M iron(II) sulfate solution (200 ml). The combined organic layer was washed with water (3×50 ml), dried over sodium sulfate and concentrated. The residue was purified on a silica column (PE/EA=5:1) to afford the title compound 5 (34 g 87% yield).

LC-MS (ESI+): m/e 169 (M+H)+, $R_t$: 1.79 min.

a2.3) 2-Quinolin-2-yl-ethanamine

A solution of 2-(cyanomethyl)quinoline (50 g, 2971 mmol, see Example a2.2)) in ethanol (400 ml) was added Raney nickel (1.7 g) and aqueous ammonia (concentrated, 250 ml). The mixture was hydrogenated with hydrogen gas (pressure: 35 psi) overnight. The mixture was filtered and concentrated. The residue was dissolved in water (500 ml).and the pH value was adjusted to 1 with concentrated aqueous HCl solution. The mixture was then extracted with ethyl acetate (3×400 ml) to remove impurities. The pH value of the aqueous layer was adjusted to 6-8 by adding aqueous sodium hydroxide. Afterwards the aqueous layer was extracted with DCM (3×300 ml) to remove impurities. The aqueous layer was then concentrated. DCM (200 ml) and MeOH (50 ml) were added to the solid, the mixture was filtered through a Bühner funnel. The solution was concentrated to dryness to afford the title compound 6 (18 g, 35% yield).

LC-MS (ESI+): m/e 173 (M+H)+, $R_t$: 0.95 min; $^1$H-NMR (400 MHz, DMSO-d6): δ=3.32 (s, 4H); 7.50 (d, J=8.4 Hz, 1H); 7.59 (t, J=7.4 Hz, 1H); 7.76 (t, J=7.6 Hz, 1H); 7.97 (d, J=8 Hz, 1H); 8.02 (d, J=8.8 Hz, 1H); 8.27 (br, 2H); 8.34 (d, J=8.4 Hz, 1H).

a3) 2,2-Difluoro-2-(quinolin-2-yl)ethanamine a3.1) 2,2-Difluoro-2-(quinolin-2-yl)-acetic acid ethyl ester A mixture of 2-bromoquinoline (5.0 g, 24.0 mmol), ethyl 2-bromo-2,2-difluoroacetate (5.8 g, 28.8 mmol) and copper power (3.5 g, 55.2 mmol) in DMSO (20 ml) was stirred at 55° C. for 5 hours. The solid was filtered off and water (100 ml) and EA (150 ml) were added. The organic layer was separated and evaporated to give the title product (4.2 g, 70%) which was used for the next step without further purification. LC-MS (ESI+): m/e 252 (M+H)+, $R_t$: 0.934 min/2.5 min.

a3.2) 2,2-Difluoro-2-(quinolin-2-yl)ethanol

To a solution of the compound from Example a2.1 (2 g, 7.9 mmol) in ethanol (20 ml) was added NaBH$_4$ (317 mg, 1.0 mmol) at 0° C. under N$_2$. The mixture was stirred for 1 h at 0° C., then at r.t. for 1.5 h. The solution was quenched with diluted HCl solution, extracted with EA (2×200 ml). The organic layer was dried over Na$_2$SO$_4$ and concentrated. The residue was purified by column chromatography on silica gel (PE:EA=10:1) to give the title compound (0.7 g, 44%). LC-MS (ESI+): m/e 210 (M+H)+, $R_t$: 0.747 min/2.5 min.

a2.3) 2,2-Difluoro-2-(quinolin-2-yl)ethyl trifluoromethanesulfonate

To a solution of the compound from Example a2.2 (300 mg, 1.4 mmol) and TEA (217 mg, 2.1 mmol) in anhydrous DCM (5 ml) was added dropwise trifluoromethanesulphonic acid anhydride (606 mg, 2.1 mmol) at −70° C. and the mixture was stirred for 1 h. The resulting solution was warmed slowly to r.t. and stirred for 1 h. The solid was filtered off and water was added. The organic layer was separated and evaporated to give the crude title compound (450 mg, 92%) which was used for the next step without further purification. LC-MS (ESI+): m/e 342 (M+H)+, $R_t$: 1.006 min.

a2.4) 2,2-Difluoro-2-(quinolin-2-yl)ethanamine

In a 500 ml round-bottomed flask, the crude product of the compound from Example a2.3 (15 g, 44 mmol) was added to 100 ml EtOH and 100 ml ammonia water to give a yellow suspension under nitrogen atmosphere, then heated to 90° C. over night. The mixture was evaporated to remove the EtOH, then extract with 500 ml EA, concentrated and purified by silical gel (EA:PE=1:1) to give 3.5 g of the title compound (35% yield) as white oil. LC-MS (ESI+): m/e 209 (M+H)+, $R_t$: 1.48 min/2.5 min; $^1$H-NMR (DMSO-d, 400 MHz): δ=8.58~8.56 (d, J=8.8 Hz, 1H), 8.11~8.07 (m, 2H), 7.88~7.84 (m, 1H), 7.83~7.81 (d, J=9.2 Hz, 1H), 7.74~7.71 (m, 1H), 3.42 (t, J=14.8 Hz, 2H), 1.72 (brs, 2H).

b) Preparation of Compounds of the Following General Formulae,

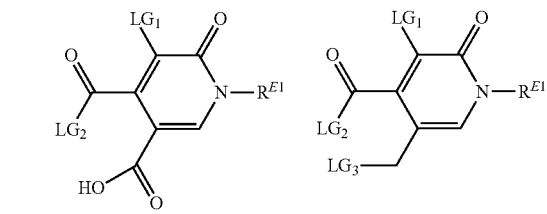

wherein LG$_1$, LG$_2$ and LG$_3$ are suitable leaving groups and R$^{E1}$ is R$^2$ as defined herein or is a suitable protecting group.

b1) Dimethyl 5-chloro-1-methyl-6-oxo-1,6-dihydropyridine-3,4-dicarboxylate (3), 1-methyl-2-oxo-1,2-dihydro-3-chloro-4-methoxycarbonyl-pyridine-5-carboxylic acid (4) and 1-methyl-2-oxo-1,2-dihydro-3-chloro-4-methoxycarbonyl-5-chloromethyl-pyridine (6)

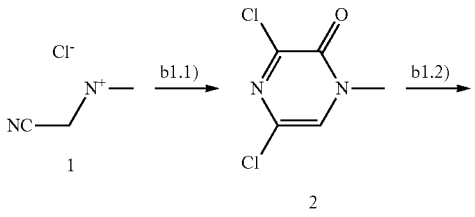

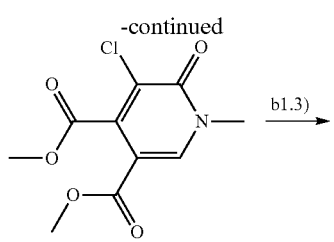

3

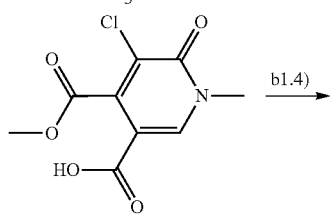

4

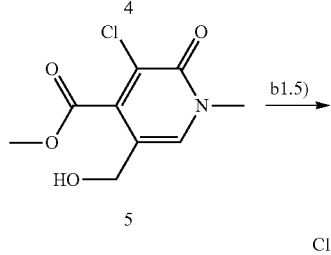

5

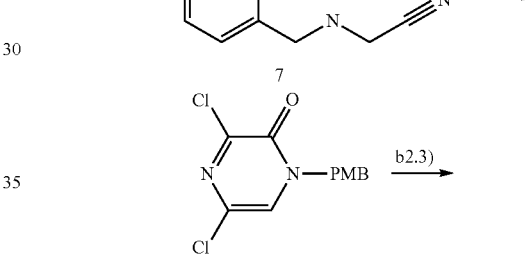

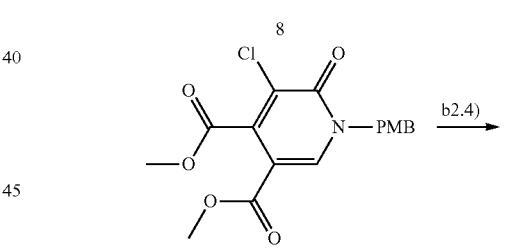

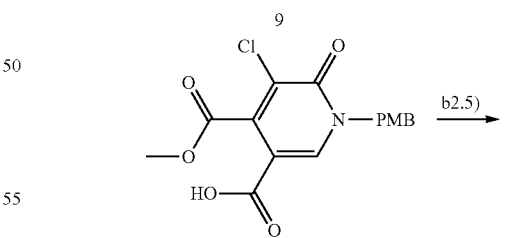

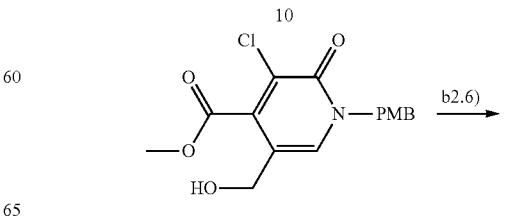

bottomed flask. The resulting solution was stirred at r.t. overnight. MeOH was added drop wise via dropping funnel to the solution. The solution was concentrated. Ethanol (100 ml) was added and the solution was concentrated to dryness to give yellow oil. Ether (50 ml) was added and the oil solidified into a solid which was ground into powder. The mixture was filtered to afford compound (5) (20.4 g, 79% yield). LC-MS (ESI+): m/e 232 (M+H)$^+$, R$_t$:1.21 min.

b1.5) 1-Methyl-2-oxo-1,2-dihydro-3-chloro-4-methoxycarbonyl-5-chloromethyl-pyridine (6)

SOCl$_2$ (22.2 ml, 305 mmol) and DMF (0.5 ml, 6.46 mmol) were added to a suspension of compound (5) (14.1 g, 60.9 mmol) in CHCl$_3$ (100 ml) and the reaction was stirred at 68° C. for 16 h. The solvent was removed and the resulting mixture was purified on a silica column (DCM/MeOH=100:1) to afford compound (6) (5.55 g, 35% yield). MS (ESI+): m/e 250 (M+H)$^+$, R$_t$:1.58 min.

b2) 1-(4-Methoxy-benzyl)-2-oxo-1,2-dihydro-3-chloro-4-methoxycarbonyl-5-chloromethyl-pyridine (12)

b1.1) Compound (2)

To a solution of cyano-N-methylmethanaminium chloride (6.4 g, 39.9 mmol) in chlorobenzene (50 ml) was added dropwise oxalyl chloride (12 ml, 137 mmol) at r. t., then the resulting solution was heated slowly to 90° C. and stirred overnight. The solvent was removed, the residue was purified by column chromatography on silica gel (PE:EA=10:1) to give the title compound as yellow oil (5 g, 70% yield). LC-MS (ESI+): m/e 178 (M+H)$^+$, R$_t$: 1.54 min.

b1.2) Compound (3)

A solution of compound (2) (40 g, 223 mmol) and 2-butynedioic acid dimethyl ester (950 g, 670 mmol) in xylene (400 ml) was heated at 145° C. overnight. The mixture was allowed to cool to r.t. The reaction mixture was filtered to afford compound (3) (29.5 g, 50.8% yield). LC-MS (ESI+): m/e 260 (M+H)$^+$, R$_t$: 1.50 min; $^1$H-NMR (DMSO-d6, 400 MHz): δ=3.60 (s, 3H), 3.79 (s, 3H), 3.87 (s, 3H), 8.67 (s, 1H).

b1.3) 1-Methyl-2-oxo-1,2-dihydro-3-chloro-4-methoxycarbonyl-pyridine-5-carboxylic acid (4)

Lithium hydroxide (3.69 g, 154 mmol) was added to a solution of compound (3) (20 g, 77 mmol) in MeOH (200 ml)/water (40 ml) and the mixture was stirred for 3 h. The reaction solution was adjusted to pH 6 with diluted HCl. The solid product was filtered off and washed with cold ether to afford compound (4) (17 g, 90% yield). LC-MS (ESI+): m/e 246 (M+H)$^+$, R$_t$: 1.29 min.

b1.4) Compound (5)

A BH$_3$-THF solution (300 ml, 300 mmol) was added carefully to compound (4) (27.4 g, 112 mmol) in a 250 ml round- -continued

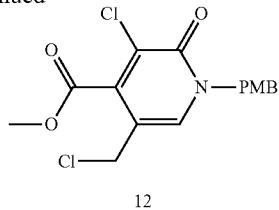

12 b2.1) 2-(4-Methoxybenzylamino)-acetonitrile (7)

A mixture of TEA (55.9 ml, 401 mmol), (4-methoxyphenyl)methanamine (50 g, 364 mmol) and 2-bromoacetonitrile (43.7 g, 364 mmol) in THF (500 ml) was stirred at about 10° C. for about 12 h in a 500 ml round-bottomed flask. The reaction was filtered through a pad of silica gel. The crude material was deposited onto silica gel, loaded onto a silica gel column and eluted with Hex/EtOAc (1:1) to afford the title compound (49 g, 278 mmol, 76% yield). $^1$H-NMR (CDCl$_3$, 400 MHz): δ=3.55 (s, 2H), 3.81 (s, 3H), 3.87 (s, 2H), 6.88 (d, 2H, J=8.4 Hz), 7.26 (d, 2H, J=8.0 Hz)

b2.2) 3,5-Dichloro-1-(4-methoxybenzyl)pyrazin-2(1H)-one (8)

Oxalyl chloride (17.5 ml, 200 mmol) was added dropwise via a dropping funnel to a mixture of compound (7) (8.5 g, 48.2 mmol) in chlorobenzene (60 ml). The reaction was heated at about 90° C. for about 16 h. The solvent was removed. The resulting mixture was deposited onto silica gel and loaded onto a silica gel column and eluted with Hex/EtOAc (10:1) to afford 3,5-dichloro-1-(4-methoxybenzyl)pyrazin-2(1H)-one (4.0 g, 13.33 mmol, 27.6% yield).

b2.3) Dimethyl 5-chloro-1-(4-methoxybenzyl)-6-oxo-1,6-dihydropyridine-3,4-dicarboxylate (9)

Compound (8) (2.0 g, 7.01 mmol) and 2-butynedioic acid dimethyl ester (2.99 g, 21.04 mmol) were added to xylene (40 ml). The reaction was heated at about 150° C. for about 16 h. The reaction was cooled to about 25° C. The reaction mixture was filtered through a Büchner funnel to afford the title compound (0.9 g, 2.338 mmol, 33.3% yield). LC-MS (ESI+): m/e 366 (M+H)$^+$, R$_t$: 1.98 min; $^1$H-NMR (DMSO-d6, 400 MHz): δ=3.73 (s, 3H), 3.79 (s, 3H), 3.88 (s, 3H), 5.21 (s, 2H), 6.91 (d, 2H, J=6.8 Hz), 7.34 (d, 2H, J=6.8 Hz), 8.81 (s, 1H).

b2.4) 1-(4-Methoxybenzyl)-2-oxo-1,2-dihydro-3-chloro-4-methoxycarbonyl-pyridine-5-carboxylic acid (10)

Lithium hydroxide (1.884 g, 44.8 mmol) was added to a solution of compound (9) (8.2 g, 22.42 mmol) in MeOH (150 ml)/water (100 ml). The reaction was stirred for about 12 h at r. t. and the reaction solution was adjusted to pH=2 with diluted aqueous HCl. The solid was filtered and washed with cold ether to give the title compound (8.4 g, 21.49 mmol, 96% yield). LC-MS (ESI+): m/e 352(M+H)$^+$, R$_t$: 1.73 min; $^1$H-NMR (DMSO-d6, 400 MHz): δ=3.75 (s, 3H), 3.83 (s, 3H), 5.20 (s, 2H), 6.93 (d, 2H, J=8.8 Hz), 7.33 (d, 2H, J=8.8 Hz), 8.68 (s, 1H), 13.39 (br, 1H).

b2.5) 1-(4-Methoxybenzyl)-2-oxo-1,2-dihydro-3-chloro-4-methoxycarbonyl-5-hydroxymethyl-pyridine (11)

A BH$_3$-THF solution (100 ml, 100 mmol) was added carefully to compound (10) (8.4 g, 23.88 mmol) in a 100 ml round-bottomed flask. The resulting solution was stirred at about r. t. overnight. MeOH was added. The solution was concentrated to dryness to give the title compound (8.15 g, 23.89 mmol, 100% yield) as a yellow solid. LC-MS (ESI+): m/e 338(M+H)$^+$, R$_t$: 1.65 min.

b2.6) 1-(4-Methoxybenzyl)-2-oxo-1,2-dihydro-3-chloro-4-methoxycarbonyl-5-chloromethyl-pyridine (12)

SOCl$_2$ (0.1 ml, 1.370 mmol) and DMF (0.1 ml, 1.291 mmol) were each slowly added in sequence to a suspension of compound (11) (360 mg, 1.066 mmol) in CHCl$_3$ (10 ml) and the reaction was stirred at 70° C. for about 3 h. The solvent was removed and the resulting mixture was deposited onto silica gel, loaded onto a silica gel column and eluted with MeOH/DCM (1:100) to afford the title compound (110 mg, 0.309 mmol, 29.0% yield). $^1$H-NMR (CDCl$_3$, 400 MHz): δ=3.80 (s, 3H), 3.98 (s, 3H), 4.37 (s, 2H), 5.09 (s, 2H), 6.89 (d, 2H, J=8.0 Hz), 7.28 (d, 2H, J=8.0 Hz).

b3) 1-Methyl-2-oxo-1,2-dihydro-3-(4-pyridyl)-4-methoxycarbonyl-pyridine-5-carboxylic acid b3.1) Dimethyl 5-(4-pyridyl)-1-methyl-6-oxo-1,6-dihydropyridine-3,4-dicarboxylate To a mixture of compound (4) (3.5 g, 13.5 mmol), pyridine-4-yl-boronic acid (4.9 g, 40.4 mmol), Pd(dppf)Cl$_2$ (1.1 g, 1.3 mmol) and Cs$_2$CO$_3$ (13.1 g, 40.4 mmol) in DME/water (4/1, 80 ml) was stirred at 90° C. overnight. The solution was concentrated and purified by column chromatography on silica gel (DCM/MeOH=100:1) to give title compound as off-white solid (1.6 g, 40%). LC-MS (ESI+): m/e 303 (M+H)$^+$, R$_t$: 0.561 min.

b3.2) 1-Methyl-2-oxo-1,2-dihydro-3-(4-pyridyl)-4-methoxycarbonyl-pyridine-5-carboxylic acid To a solution of 1-methyl-2-oxo-1,2-dihydro-3-(4-pyridyl)-4-methoxycarbonyl-pyridine-5-carboxylic acid (1.0 g, 3.3 mmol, see Example b3.1)) and lithium hydroxide (159 mg, 6.6 mmol) in MeOH (20 ml) and water (4 ml) was stirred at 30° C. for 3 hours, the reaction solution was adjusted pH=6 with dilute HCl and the solid was filtered off and washed with cold THF to give the title compound as white solid (650 mg, 68%). LC-MS (ESI+): m/e 289 (M+H)$^+$, R$_t$: 0.431 min.

c) Preparation of Compounds of the Following General Formula,

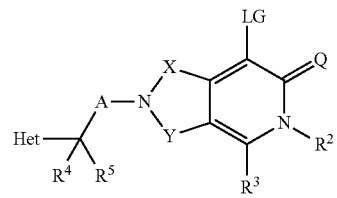

wherein LG is a suitable leaving groups and R$^2$, R$^3$, R$^4$, R$^5$, X, Y, Q, A and Het are as defined herein.

c1) 7-Chloro-5-methyl-2-(2-quinolin-2-yl-ethyl)-5H-pyrrolo[3,4-c]pyridine-1,3,6-trione 2-Quinolin-2-yl-ethanamine (2 g, 11.64 mmol, see Example a1)), DIPEA (5.55 ml, 31.8 mmol) and PyBOP (7.16 g, 13.76 mmol) were each added to a suspension of compound (4) (2.6 g, 10.59 mmol) in DCM and the reaction was stirred at r.t. for 16 h. The reaction was filtered to afford the title compound (3.17 g, 81% yield).

LC-MS (ESI+): m/e 368 (M+H)$^+$, R$_t$: 1.68 min; $^1$H-NMR (400 MHz, DMSO-d6): δ=3.23 (t, J=7 Hz, 2H); 3.58 (s, 3H); 4.01 (t, J=7.2 Hz, 2H); 7.47 (d, J=8.4 Hz, 1H); 7.55 (t, J=7 Hz, 1H); 7.71 (t, J=7 Hz, 1H); 7.84 (d, J=8.4 Hz, 1H); 7.93 (d, J=8 Hz, 1H); 8.28 (d, J=8 Hz, 1H); 8.63 (s, 1H).

c2) 7-Chloro-5-methyl-2-(2-[1,2,4]triazolo[1,5-a]pyridin-2-yl-ethyl)-5H-pyrrolo[3,4-c]pyridine-1,3,6-trione The title compound was prepared in analogy to the process described in Example c1) starting from 2-([1,2,4]triazolo[1,5-a]pyridin-2-yl)ethanamine and compound (4).

MS (ESI+): m/e 380.00 (M+Na)$^+$ and 358.05 (M+H)$^+$.

c3) 7-Chloro-5-methyl-2-(2-quinolin-2-yl-ethyl)-1,2-dihydro-5H-pyrrolo[3,4-c]pyridine-3,6-dione c3.1) 7-Chloro-5-methyl-2-(2-quinolin-2-yl-ethyl)-1-hydroxyl-1,2-dihydro-5H-pyrrolo[3,4-c]pyridine-3,6-dione Zinc (0.44 g, 6.8 mmol) was added to a solution of 7-chloro-5-methyl-2-(2-quinolin-2-yl-ethyl)-5H-pyrrolo[3,4-c]pyridine-1,3,6-trione (1 g, 2.72 mmol, see Example c1)) in acetic acid (10 ml) and the reaction was stirred for 3 h under reflux. The reaction was cooled to r.t. and brine (20 ml) was added. The aqueous layer was extracted with THF (3×25 ml) and the combined organic phase was concentrated to dryness. The mixture was diluted with THF (30 ml)/MeOH (5 ml), filtered through a pad of silica gel and concentrated to give crude product (1.4 g 139% yield), which was used in the next steps without further purification.

LC-MS (ESI): m/e 370 (M+H)$^+$, $R_t$: 1.62 min.

c3.2) 7-Chloro-5-methyl-2-(2-quinolin-2-yl-ethyl)-1,2-dihydro-5H-pyrrolo[3,4-c]pyridine-3,6-dione BF$_3$.OEt$_2$ (1.234 ml, 9.73 mmol) and triethylsilane (5.18 ml, 32.4 mmol) were added to a suspension of 7-Chloro-5-methyl-2-(2-quinolin-2-yl-ethyl)-1-hydroxyl-1,2-dihydro-5H-pyrrolo[3,4-c]pyridine-3,6-dione (1.2 g, 3.24 mmol, see Example c3.1)) in DCM (5 ml) at 0° C. and the reaction stirred at 0° C. for 3 h, which was then warmed to r.t. and stirred overnight. The solvent was removed and the resulting mixture was purified via preparative HPLC (Waters 2767 PHW003, eluent: MeCN/aqueous 0.05% solution of ammonium hydrogen carbonate (gradient: 20:80 to 40:60 over 14 min), column: Hanbon Benetnach C18, 10 μm, 20×250 mm) to afford the title compound (65 mg, 6.5% yield).

LC-MS (ESI)$^+$: m/e 354 (M+H)$^+$, $R_t$: 1.32 min; $^1$H-NMR (400 MHz, CDCl$_3$): δ=3.35 (t, J=7.2 Hz, 2H); 3.65 (s, 3H); 4.08 (t, J=7 Hz, 2H); 4.41 (s, 2H); 7.36 (d, J=8.4 Hz, 1H); 7.51 (t, J=7.4 Hz, 1H); 7.70 (t, J=7.6 Hz, 1H); 7.79 (d, J=8 Hz, 1H); 7.85 (s, 1H); 7.99 (d, J=8.4 Hz, 1H); 8.10 (d, J=8.4 Hz, 1H).

c4) 7-Chloro-5-methyl-2-(2-quinolin-2-yl-ethyl)-3,5-dihydro-2H-pyrrolo[3,4-c]pyridine-1,6-dione TEA (4.18 ml, 30.0 mmol) and 2-quinolin-2-yl-ethanamine (1.89 g, 11 mmol, see Example a1)) were each rapidly added in sequence to a suspension of 1-methyl-2-oxo-1,2-dihydro-3-chloro-4-methoxycarbonyl-5-chloromethyl-pyridine (2.5 g, 10.00 mmol, see compound (6) of Example b1.5)) in EtOH (10 ml). The reaction was heated in a microwave at about 80° C. for about 20 min. The reaction was cooled to r.t. and the mixture was filtered and washed with a little EtOH to afford the title compound (1.35 g, 38.2% yield). MS (ESI+): m/e 418 (M+H)$^+$, $R_t$:1.67 min; $^1$H-NMR (400 MHz, CDCl$_3$): δ=3.28 (t, J=7.2 Hz, 2H); 3.53 (s, 3H); 3.97 (t, J=7.2 Hz, 2H); 4.31 (s, 2H); 7.49 (d, J=8.4 Hz, 1H); 7.56 (t, J=7.3 Hz, 1H); 7.73 (t, J=7.6 Hz, 1H); 7.92-7.95 (m, 2H); 7.98 (s, 1H); 8.30 (d, J=8.4 Hz, 1H).

c5) 7-Chloro-2-(2-imidazo[1,2-a]pyridin-2-yl-ethyl)-5-methyl-3,5-dihydro-2H-pyrrolo[3,4-c]pyridine-1,6-dione TEA (5 ml, 36 mmol) was added to a suspension of 2-(imidazo[1,2-a]pyridine-2-yl)ethanamine (1.934 g, 12 mmol) and 1-methyl-2-oxo-1,2-dihydro-3-chloro-4-methoxycarbonyl-5-chloromethyl-pyridine (3 g, 12 mmol, see compound (6) of Example b1)) in MeCN (5 ml). The reaction was heated in a CEM microwave at about 100° C. for about 40 min. The solvent was removed and the resulting mixture was deposited onto silica gel, loaded onto a silica gel column and eluted with DCM/MeOH (50:1) to give 2.9 g of crude product. The crude product was washed with water, dried to afford the title compound (2 g, 5.76 mmol, 48.1% yield).

LC-MS (ESI)$^+$: m/e 343 (M+H)$^+$, $R_t$: 1.43 min; $^1$H-NMR (400 MHz, DMSO-d6): δ=3.03 (t, J=7.2 Hz, 2H); 3.54 (s, 3H); 3.84 (t, J=7.2 Hz, 2H); 4.26 (s, 2H); 6.84 (t, J=7 Hz, 1H); 7.19 (t, J=7.8 Hz, 1H); 7.47 (d, J=7.8 Hz, 1H); 7.77 (s, 1H); 7.97 (s, 1H); 8.47 (d, J=6.4 Hz, 1H).

c6) 7-Chloro-5-methyl-2-(2-[1,2,4]triazolo[1,5-a]pyridin-2-yl-ethyl)-3,5-dihydro-2H-pyrrolo[3,4-c]pyridine-1,6-dione TEA (3.01 ml, 21.59 mmol) was added rapidly to a solution of 2-([1,2,4]triazolo[1,5-a]pyridin-2-yl)ethanamine (1.167 g, 7.20 mmol) and 1-methyl-2-oxo-1,2-dihydro-3-chloro-4-methoxycarbonyl-5-chloromethyl-pyridine (1.8 g, 7.20 mmol, see compound (6) of Example b1)) in MeCN (15 ml). The reaction was heated in a microwave at about 100° C. for about 40 min. The reaction was cooled to r.t. and the mixture was filtered through a Büchner funnel. The residue solid was triturated with water (2×20 ml). The resulting solid was filtered off on a Büchner funnel to afford the title compound (1.3 g, 3.78 mmol, 52.5% yield).

LC-MS (ESI)$^+$: m/e 344 (M+H)$^+$, $R_t$: 1.36 min; $^1$H-NMR (400 MHz, DMSO-d6): δ=3.17 (t, J=7.2 Hz, 2H), 3.54 (s, 3H), 3.92 (t, J=7 Hz, 2H), 4.32 (s, 2H), 7.13-7.16 (m, 1H); 7.63 (t, J=8 Hz, 1H); 7.75 (d, J=8.8 Hz, 1H); 7.99 (s, 1H); 7.87 (d, J=7.2 Hz, 1H).

c7) 7-Chloro-5-(4-methoxy-benzyl)-2-(2-quinolin-2-yl-ethyl)-3,5-dihydro-2H-pyrrolo[3,4-c]pyridine-1,6-dione A solution of 2-(quinolin-2-yl)ethanamine (48.4 mg, 0.281 mmol, see Example a1)), methyl 3-chloro-5-(chloromethyl)-1-(4-methoxybenzyl)-2-oxo-1,2-dihydropyridine-4-carboxylate (100 mg, 0.281 mmol) and TEA (0.117 ml, 0.842 mmol) were dissolved in EtOH (3.0 ml) in a 5 ml microwave reaction vial. The suspension was heated in a Biotage microwave at about 100° C. for about 20 min. After cooling, it was verified by LC-MS that the reaction was almost completed. The solution was concentrated to dryness and recrystallized from EtOH to give the title compound (69 mg, 0.150 mmol, 53.4% yield) as a yellow solid.

LC-MS (ESI+): m/e 460 (M+H)$^+$, $R_t$: 1.91 min; $^1$H-NMR (CDCl$_3$, 400 MHz): δ=3.35 (t, 2H, J1=6.4 Hz, J2=7.2 Hz), 3.79 (s, 3H), 4.10 (m, 2H), 4.16 (s, 2H), 5.12 (s, 2H), 6.86 (d, 2H, J1=8.4 Hz, J2=2.8 Hz), 7.28 (m, 3H), 7.35 (d, 1H, J=8.8 Hz), 7.53 (m, 1H), 7.68 (m, 1H), 7.79 (m, 1H), 7.98 (m, 1H), 8.09 (m, 1H).

c8) 7-Chloro-5-methyl-2-[2-(1-methyl-1H-benzoimidazol-2-yl)-ethyl]-3,5-dihydro-2H-pyrrolo[3,4-c]pyridine-1,6-dione K$_2$CO$_3$ (8.35 g, 60.4 mmol) was added rapidly to a suspension of 2-(1-methyl-1H-benzo[d]imidazol-2-yl)ethanamine dihydrochloride (5 g, 20.15 mmol) in MeOH (50 ml) and the reaction was stirred for about 5 h. The mixture was filtered and the filtrate was concentrated. The residue and TEA (28.1 ml, 201 mmol) were added to a solution of 1-methyl-2-oxo-1,2-dihydro-3-chloro-4-methoxycarbonyl-5-chloromethyl-pyridine (5.04 g, 20.15 mmol, see compound (6) of Example b1)) in MeCN (100 ml). The mixture was heated at about 90° C. overnight. The reaction was cooled to r.t. and the mixture was filtered through a sintered glass funnel. The solid was washed with water and dried to afford the title compound (3.9 g, 10.93 mmol, 54.2% yield).

LC-MS (ESI+): m/e 357 (M+H)$^+$, $R_t$: 1.55 min; $^1$H-NMR (400 MHz, DMSO-d6): δ=3.24 (t, J=7.4 Hz, 2H); 3.54 (s, 3H); 3.77 (s, 3H); 3.97 (t, J=7.2 Hz, 2H); 4.38 (s, 2H); 7.13-7.23 (m, 2H); 7.50 (d, J=7.6 Hz, 1H); 7.55 (d, J=7.2 Hz, 1H); 8.01 (s, 1H).

II. Preparation of Compounds of the Formula I

II.1 Preparation of Compounds of the Formula I in which X and Y are Both C(O)

Example 1

5-Methyl-7-morpholin-4-yl-2-(2-quinolin-2-yl-ethyl)-5H-pyrrolo[3,4-c]pyridine-1,3,6-trione Morpholine (0.355 ml, 4.08 mmol) was added to a solution of 7-chloro-5-methyl-2-(2-quinolin-2-yl-ethyl)-5H-pyrrolo[3,4-c]pyridine-1,3,6-trione (0.5 g, 1.36 mmol, see Example c1)) in EtOH (30 ml) and the reaction was stirred at 90° C. for 16 h. The solvent was removed to give the title compound (0.7 g, 123% yield), which was used in the next steps without further purification.

LC-MS (ESI+): m/e 419 (M+H)$^+$, $R_t$: 2.18 min; $^1$H-NMR (400 MHz, CDCl$_3$): δ=3.30 (t, J=7.2 Hz, 2H); 3.48 (t, J=4.4 Hz, 4H); 3.54 (s, 3H); 3.72 (t, J=4.6 Hz, 4H); 4.12 (t, J=7.2 Hz, 2H); 7.34 (d, J=8.4 Hz, 1H); 7.46-7.51 (m, 2H); 7.65 (t, J=7.6 Hz, 1H); 7.77 (d, J=8.4 Hz; 1H); 7.92 (d, J=8.8 Hz, 1H); 8.08 (d, J=8.4 Hz, 1H).

Example 2

5-Methyl-7-(4-methyl-piperazin-1-yl)-2-(2-quinolin-2-yl-ethyl)-5H-pyrrolo[3,4-c]pyridine-1,3,6-trione The title compound was prepared in analogy to the process described in Example 1 starting from 7-chloro-5-methyl-2-(2-quinolin-2-yl-ethyl)-5H-pyrrolo[3,4-c]pyridine-1,3,6-trione (see Example c1)) and 1-methyl-piperazine.

LC-MS (ESI): m/e 432 (M+H)$^+$, $R_t$: 1.80 min.

Example 3

5-Methyl-7-(1,1-dioxo-thiomorpholin-4-yl)-2-(2-quinolin-2-yl-ethyl)-5H-pyrrolo[3,4-c]pyridine-1,3,6-trione K$_2$CO$_3$ (1.127 g, 8.16 mmol), Pd$_2$(dba)$_3$ (0.249 g, 0.272 mmol) and dicyclohexyl[2',4',6'-tris(1-methylethyl)[1,1'-biphenyl]-2-yl]-phosphine (0.13 g, 0.272 mmol) were subsequently added to a suspension of 7-chloro-5-methyl-2-(2-quinolin-2-yl-ethyl)-5H-pyrrolo[3,4-c]pyridine-1,3,6-trione (1 g, 2.72 mmol, see Example c1)) and thiomorpholine 1,1-dioxide (0.551 g, 4.08 mmol) in toluene (10 ml) and the mixture was stirred for 4 h under reflux. The solvent was removed and the resulting mixture was purified on a silica column (DCM/MeOH=50:1) to afford the title compound (0.8 g, 63% yield).

LC-MS (ESI+): m/e 467 (M+H)$^+$, $R_t$: 1.42 min.

Example 4

5-Methyl-7-(4-pyridyl)-2-(2-quinolin-2-yl-ethyl)-5H-pyrrolo[3,4-c]pyridine-1,3,6-trione To a mixture of 1-methyl-2-oxo-1,2-dihydro-3-(4-pyridyl)-4-methoxycarbonyl-pyridine-5-carboxylic acid (500 mg, 1.7 mmol, see Example b3)), 2-aminoethyl quinoline (358 mg, 2.0 mmol), PyBOP (1.2 g, 2.2 mmol) and DIPEA (671 mg, 5.2 mmol) in DCM (20 ml) was stirred at r.t. overnight. The solvent was removed, the residue was purified by column chromatography on silica gel (PE:EA=10:1) to give the title compound as a white solid (600 mg, 84%).

LC-MS (ESI+): m/e 411 (M+H)$^+$, $R_t$: 1.715 min.

Example 5

5-Methyl-7-morpholin-4-yl-2-(2-[1,2,4]triazolo[1,5-a]pyridin-2-yl-ethyl)-5H-pyrrolo[3,4-c]pyridine-1,3,6-trione The title compound was prepared in analogy to the process described in Example 1 starting from 7-chloro-5-methyl-2-(2-[1,2,4]triazolo[1,5-a]pyridin-2-yl-ethyl)-5H-pyrrolo[3,4-c]pyridine-1,3,6-trione (see Example c2)).

MS (ESI+): m/e 447.05 (M+Na)$^+$, 425.10 (M+H)$^+$.

II.2 Preparation of Compounds of the Formula I in which X is CH$_2$ and Y is C(O)

Example 6

5-Methyl-7-morpholin-4-yl-2-(2-quinolin-2-yl-ethyl)-1,2-dihydro-5H-pyrrolo[3,4-c]pyridine-3,6-dione Zinc (0.375 g, 5.74 mmol) was added to a solution of 5-methyl-7-morpholin-4-yl-2-(2-quinolin-2-yl-ethyl)-5H-pyrrolo[3,4-c]pyridine-1,3,6-trione (0.8 g, 1.91 mmol, see Example 1) in acetic acid (15 ml) and the reaction was stirred for 8 h under reflux. The solvent was removed and the resulting mixture was purified via preparative HPLC (Waters system, eluent: MeCN/ammonium acetate buffer (gradient: 10:90 to 80:20 over 20 min), column: Hanbon Benetnach C18, 10 μm, 21.2×250 mm) to afford the title compound (47 mg, 6% yield).

LC-MS (ESI+): m/e 405 (M+H)$^+$, $R_t$:1.69 min; $^1$H-NMR (400 MHz, CDCl$_3$): δ=3.12 (t, J=4.4 Hz, 4H); 3.35 (t, J=7 Hz, 2H); 3.56 (s, 3H); 3.75 (t, J=4.6 Hz, 4H); 4.05 (t, J=7 Hz, 2H); 4.43 (s, 2H); 7.28 (d, J=8.4 Hz, 1H); 7.52 (t, J=7.4 Hz, 1H); 7.70 (t, J=7.4 Hz, 2H); 7.80 (d, J=8.4 Hz, 1H); 7.98 (d, J=8.4 Hz, 1H); 8.10 (d, J=8 Hz, 1H).

Example 7

5-Methyl-7-(4-methyl-piperazin-1-yl)-2-(2-quinolin-2-yl-ethyl)-1,2-dihydro-5H-pyrrolo[3,4-c]pyridine-3,6-dione

7.1 5-Methyl-7-(4-methyl-piperazin-1-yl)-2-(2-quinolin-2-yl-ethyl)-1-hydroxyl-1,2-dihydro-5H-pyrrolo[3,4-c]pyridine-3,6-dione Zinc (0.38 g, 5.8 mmol) was added rapidly to a solution of 5-methyl-7-(4-methyl-piperazin-1-yl)-2-(2-quinolin-2-yl-ethyl)-5H-pyrrolo[3,4-c]pyridine-1,3,6-trione (1 g, 2.318 mmol, see Example 2) in acetic acid (30 ml). The reaction was heated at about 110° C. for about 4 h. The solvent was removed. The residue was purified on a silica column (DCM/MeOH=10:1) to afford the title compound (0.5 g, 49.8% yield).

LC-MS (ESI+): m/e 416 (M−18)$^+$, $R_t$: 1.61 min.

7.2 5-Methyl-7-(4-methyl-piperazin-1-yl)-2-(2-quinolin-2-yl-ethyl)-1,2-dihydro-5H-pyrrolo[3,4-c]pyridine-3,6-dione The title compound was prepared in analogy to the process described in Example c3.2) starting from 5-methyl-7-(4-methyl-piperazin-1-yl)-2-(2-quinolin-2-yl-ethyl)-1-hydroxyl-1,2-dihydro-5H-pyrrolo[3,4-c]pyridine-3,6-dione (see Example 7.1)).

LC-MS (ESI): m/e 418 (M+H)$^+$, R$_t$: 1.67 min; $^1$H-NMR (400 MHz, CDCl$_3$): δ=2.25 (s, 3H); 2.42 (s, 4H); 3.10 (t, J=4.8 Hz, 4H); 3.27 (t, J=7.2 Hz, 2H); 3.48 (s, 3H); 3.97 (t, J=7 Hz, 2H); 4.36 (s, 2H); 7.30 (d, J=8 Hz, 1H); 7.44 (t, J=7.4 Hz, 1H); 7.60-7.64 (m, 2H); 7.20 (d, J=8.4 Hz, 1H); 7.92 (d, J=8.4 Hz, 1H); 8.03 (d, J=8.4 Hz, 1H).

Example 8

5-Methyl-7-pyridin-4-yl-2-(2-quinolin-2-yl-ethyl)-1,2-dihydro-5H-pyrrolo[3,4-c]pyridine-3,6-dione A mixture of 5-methyl-7-(4-pyridyl)-2-(2-quinolin-2-yl-ethyl)-5H-pyrrolo[3,4-c]pyridine-1,3,6-trione (60 mg, 0.15 mmol, see Example 4) and zinc power (28 mg, 0.4 mmol) in acetic acid (3 ml) was stirred at 110° C. for 3 hours. The solution was concentrated and purified by column chromatography on silica gel (EA:MeOH=5:1) to give the title compound as a white solid (23 mg, 40%).

LC-MS (ESI+): m/e 397 (M+H)$^+$, R$_t$: 1.630 min; $^1$H-NMR (400 MHz, CDCl$_3$): δ=8.63 (d, J=5.6 Hz, 2H), 8.10 (d, J=8.4 Hz, 1H), 7.96 (d, J=8.0 Hz, 1H), 7.94 (s, 1H), 7.80 (d, J=8.4 Hz, 1H). 7.72-7.68 (m, 1H), 7.53 (t, J=7.2 Hz, 1H), 7.37-7.30 (m, 3H), 4.37 (s, 2H), 4.05 (t, J=6.8 Hz, 2H), 3.65 (s, 3H), 3.34 (t, J=6.8 Hz, 2H).

II.3 Preparation of Compounds of the Formula Ia

Example 9

5-Methyl-7-morpholin-4-yl-2-(2-quinolin-2-yl-ethyl)-3,5-dihydro-2H-pyrrolo[3,4-c]pyridine-1,6-dione

9.1 5-Methyl-7-morpholin-4-yl-2-(2-quinolin-2-yl-ethyl)-1,6-dioxo-5H-pyrrolo[3,4-c]pyridine-3-thione 5-Methyl-7-morpholin-4-yl-2-(2-quinolin-2-yl-ethyl)-5H-pyrrolo[3,4-c]pyridine-1,3,6-trione (0.7 g, 1.67 mmol, see Example 1) was dissolved in toluene (20 ml), stirred and heated to 120° C. and Lawesson's reagent (0.338 g, 0.836 mmol) was added. The reaction was stirred at 120° C. for 16 h. The reaction mixture was cooled to r.t., filtered though a pad of silica gel and concentrated to afford the crude title compound (0.65 g, 77% yield), which was used in the next steps without further purification.

MS (ESI+): m/e 435 (M+H)$^+$, R$_t$: 1.53 min.

9.2 5-Methyl-7-morpholin-4-yl-2-(2-quinolin-2-yl-ethyl)-3,5-dihydro-2H-pyrrolo[3,4-c]pyridine-1,6-dione Nickel (7.56 mg, 0.129 mmol) was added rapidly to a mixture of 5-methyl-7-morpholin-4-yl-2-(2-quinolin-2-yl-ethyl)-1,6-dioxo-5H-pyrrolo[3,4-c]pyridine-3-thione (0.56 g, 1.289 mmol, see Example 9.1) in EtOH (20 ml)/THF (5 ml). The mixture was allowed to stir under a hydrogen atmosphere (at a pressure of about 35 psi) at r.t. for about 16 h. The solvent was removed and the resulting mixture was purified via preparative HPLC (System: Isco Combi Flash Companion XL, eluent: MeCN/ammonium acetate buffer (gradient: 0:100 to 60:40 over 20 min), column: C-18, 21.2×250 mm) to afford the title compound (127 mg, 24.36% yield).

LC-MS (ESI+): m/e 405 (M+H)$^+$, R$_t$: 1.7 min; $^1$H-NMR (400 MHz, CDCl$_3$): δ=3.32 (t, J=7.2 Hz, 2H); 3.52-3.55 (m, 7H); 3.82 (t, J=4.4 Hz, 4H); 4.02 (t, J=7.2 Hz, 2H); 4.19 (s, 2H); 6.89 (s, 1H); 7.39 (d, J=8.4 Hz, 1H); 7.53 (t, J=7.4 Hz, 1H); 7.71 (t, J=7.8 Hz, 1H); 7.81 (d, J=8 Hz, 1H); 8.00 (d, J=8.4 Hz, 1H); 8.11 (d, J=8.4 Hz, 1H).

Example 10

5-Methyl-7-(4-methyl-piperazin-1-yl)-2-(2-quinolin-2-yl-ethyl)-3,5-dihydro-2H-pyrrolo[3,4-c]pyridine-1,6-dione

10.1 5-Methyl-7-(4-methyl-piperazin-1-yl)-2-(2-quinolin-2-yl-ethyl)-1,6-dioxo-5H-pyrrolo[3,4-c]pyridine-3-thione The title compound was prepared in analogy to the process described in Example 9.1 starting from 5-methyl-7-(4-methyl-piperazin-1-yl)-2-(2-quinolin-2-yl-ethyl)-5H-pyrrolo[3,4-c]pyridine-1,3,6-trione (see Example 2).

LC-MS (ESI+): m/e 448 (M+H)$^+$, R$_t$: 1.41 min.

10.2 5-Methyl-7-(4-methyl-piperazin-1-yl)-2-(2-quinolin-2-yl-ethyl)-3,5-dihydro-2H-pyrrolo[3,4-c]pyridine-1,6-dione The title compound was prepared in analogy to the process described in Example 9.2 starting from 5-methyl-7-(4-methyl-piperazin-1-yl)-2-(2-quinolin-2-yl-ethyl)-1,6-dioxo-5H-pyrrolo[3,4-c]pyridine-3-thione (see Example 10.1).

LC-MS (ESI+): m/e 418 (M+H)$^+$, R$_t$: 1.65 min; $^1$H-NMR (400 MHz, CDCl$_3$): δ=2.47 (s, 3H); 2.76 (s, 4H); 3.31 (t, J=7 Hz, 2H); 3.51 (s, 3H); 3.63 (t, J=4.8 Hz, 4H); 4.01 (t, J=7.2 Hz, 2H); 4.17 (s, 2H); 6.88 (s, 1H); 7.37 (d, J=8.8 Hz, 1H); 7.51 (t, J=7.2 Hz, 1H); 7.69 (t, J=7.8 Hz, 1H); 7.79 (d, J=8 Hz, 1H); 7.99 (d, J=8.4 Hz, 1H); 8.10 (d, J=8.4 Hz, 1H).

Example 11

5-Methyl-7-pyridin-4-yl-2-(2-quinolin-2-yl-ethyl)-3,5-dihydro-2H-pyrrolo[3,4-c]pyridine-1,6-dione

11.1 5-Methyl-7-pyridin-4-yl-2-(2-quinolin-2-yl-ethyl)-1,6-dioxo-5H-pyrrolo[3,4-c]pyridine-3-thione To a mixture of 5-methyl-7-(4-pyridyl)-2-(2-quinolin-2-yl-ethyl)-5H-pyrrolo[3,4-c]pyridine-1,3,6-trione (50 mg, 0.12 mmol) and Lawesson's reagent (25 mg, 0.06 mmol) in toluene (5 ml) was stirred at 110° C. for 12 hours. The solution was concentrated and the residue was purified by preparative thin-layer chromatography (EA:MeOH=5:1) to give the title compound as a yellow solid (10 mg, 19%).

LC-MS (ESI+): m/e 427 (M+H)$^+$, R$_t$: 0.602 min.

11.2 5-Methyl-7-pyridin-4-yl-2-(2-quinolin-2-yl-ethyl)-3,5-dihydro-2H-pyrrolo[3,4-c]pyridine-1,6-dione To a mixture of 5-methyl-7-pyridin-4-yl-2-(2-quinolin-2-yl-ethyl)-1,6-dioxo-5H-pyrrolo[3,4-c]pyridine-3-thione (40 mg, 0.09 mmol, see Example 11.1), Raney nickel (about 400 mg) in EtOH (12 ml) was stirred at r.t. under nitrogen for 3 hours. The Raney nickel was filtered off and the filtrate was concentrated and purified by preparative thin-layer chromatography (EA:MeOH=5:1) to give the title compound as a white solid (10 mg, 26%).

LC-MS (ESI+): m/e 397 (M+H)⁺, $R_t$: 1.136 min; ¹H-NMR (400 MHz, CDCl₃): δ=8.63 (d, J=5.6 Hz, 2H), 8.08 (d, J=8.8 Hz, 1H), 7.98 (d, J=8.4 Hz, 1H), 7.80 (d, J=8.0 Hz, 1H), 7.72-7.68 (m, 1H), 7.54-7.44 (m, 1H), 7.33 (s, 1H), 7.32-7.30 (m, 3H), 4.30 (s, 2H), 4.05 (t, J=6.8 Hz, 2H), 3.62 (s, 3H), 3.32 (t, J=7.2 Hz, 2H).

Example 12

5-Methyl-7-(1,1-dioxo-thiomorpholin-4-yl)-2-(2-quinolin-2-yl-ethyl)-3,5-dihydro-2H-pyrrolo[3,4-c]pyridine-1,6-dione 12.1 5-Methyl-7-(1,1-dioxo-thiomorpholin-4-yl)-2-(2-quinolin-2-yl-ethyl)-1,6-dioxo-5H-pyrrolo[3,4-c]pyridine-3-thione A suspension of 5-methyl-7-(1,1-dioxo-thiomorpholin-4-yl)-2-(2-quinolin-2-yl-ethyl)-5H-pyrrolo[3,4-c]pyridine-1,3,6-trione (0.8 g, 1.715 mmol, see Example 3) in toluene (30 ml) was heated to 120° C., Lawesson's reagent (0.347 g, 0.857 mmol) was added and the reaction was stirred at 120° C. for 16 h. The solvent was removed and the resulting mixture was purified on a silica column (DCM/MeOH=50:1) to afford the title compound (0.5 g, 60% yield).

LC-MS (ESI+): m/e 483 (M+H)⁺, $R_t$: 1.53 min.

12.2 5-Methyl-7-(1,1-dioxo-thiomorpholin-4-yl)-2-(2-quinolin-2-yl-ethyl)-3,5-dihydro-2H-pyrrolo[3,4-c]pyridine-1,6-dione Raney nickel (0.012 g, 0.207 mmol) was added to s suspension of 5-methyl-7-(1,1-dioxo-thiomorpholin-4-yl)-2-(2-quinolin-2-yl-ethyl)-1,6-dioxo-5H-pyrrolo[3,4-c]pyridine-3-thione (0.1 g, 0.207 mmol, see Example 12.1) in EtOH (5 ml)/THF (5 ml) and the reaction was allowed to stir under an hydrogen atmosphere (pressure of about 35 psi) at r.t. for 16 h. The reaction was filtered through a pad of celite and concentrated. The resulting mixture was purified by preparative HPLC (Waters system, eluent: MeCN/ammonium acetate buffer (gradient: 12:88 to 45:55 over 15 min), column: Boston Analytics, C-18, 10 μm, 10×250 mm) to afford the title compound (45 mg, 48.0% yield).

MS (ESI+): m/e 453 (M+H)⁺, $R_t$: 1.63 min; ¹H-NMR (400 MHz, CDCl₃): δ=3.15 (t, J=4.8 Hz, 4H); 3.37 (t, J=7 Hz, 2H); 3.55 (s, 3H); 3.75 (t, J=5 Hz, 4H); 4.03 (t, J=6.8 Hz, 2H); 4.28 (s, 2H); 7.04 (s, 1H); 7.46 (d, J=8.8 Hz, 1H); 7.57 (t, J=7.6 Hz, 1H); 7.73 (t, J=7.6 Hz, 1H); 7.85 (d, J=8 Hz, 1H); 8.04 (d, J=8.4 Hz, 1H); 8.20 (d, J=8.4 Hz, 1H).

Example 13

5-Methyl-7-pyridin-3-yl-2-(2-quinolin-2-yl-ethyl)-3,5-dihydro-2H-pyrrolo[3,4-c]pyridine-1,6-dione Bis(triphenylphosphine)palladium(II) dichloride (14.88 mg, 0.021 mmol) and K₂CO₃ (176 mg, 1.27 mmol) were added to a suspension of 7-chloro-5-methyl-2-(2-quinolin-2-yl-ethyl)-3,5-dihydro-2H-pyrrolo[3,4-c]pyridine-1,6-dione (150 mg, 0.424 mmol, see Example c4)) and pyridine-3-ylboronic acid (104 mg, 0.848 mmol) in DMF (3 ml)/water (0.6 ml) and the mixture was heated in a microwave at 130° C. for 30 min. The solvent was removed and the resulting solid was purified by preparative HPLC (system: Gilson 281 (PHG008), eluent: MeCN/aqueous 0.1% TFA solution (gradient: 30:70 to 80:20 over 15 min), column: Boston symmetrix ODS-R, C-18, 10 nm, 21.2×250 mm) to afford the title compound (150 mg, 89% yield).

LC-MS (ESI+): m/e 397 (M+H)⁺, $R_t$: 1.21 min; ¹H-NMR (400 MHz, CDCl₃): δ=3.68 (s, 3H); 3.77 (t, J=6.4 Hz, 2H); 4.12 (t, J=6.6 Hz, 2H); 4.59 (s, 2H); 7.73-7.78 (m, 2H); 7.86 (t, J=7.8 Hz, 1H); 7.94 (d, J=8.8 Hz, 1H); 8.04 (t, J=7.4 Hz, 1H); 8.12 (d, J=8.4 Hz, 1H); 8.44 (d, J=8.4 Hz, 1H); 8.51 (d, J=8 Hz, 1H); 8.69 (d, J=5.2 Hz, 1H); 8.81 (s, 1H); 8.87 (d, J=8.4 Hz, 1H).

Example 14

5-(4-Methoxy-benzyl)-7-morpholin-4-yl-2-(2-quinolin-2-yl-ethyl)-3,5-dihydro-2H-pyrrolo[3,4-c]pyridine-1,6-dione A mixture of 7-chloro-5-(4-methoxy-benzyl)-2-(2-quinolin-2-yl-ethyl)-3,5-dihydro-2H-pyrrolo[3,4-c]pyridine-1,6-dione (65 mg, 0.141 mmol, see Example c7)), morpholine (12.31 mg, 0.141 mmol), Xantphos (82 mg, 0.141 mmol), palladium diacetate (31.7 mg, 0.141 mmol) and Cs₂CO₃ (138 mg, 0.424 mmol) in dioxane (5 ml) was heated in a CEM microwave at about 120° C. for about 30 min. The solvent was removed and the crude material was purified via preparative thin-layer chromatography (MeOH/DCM=5:95) to give the title compound (30 mg, 0.056 mmol, 39.5% yield).

LC-MS (ESI+): m/e 511(M+H)⁺, $R_t$: 1.95 min; ¹H-NMR (CDCl₃, 400 MHz): δ=1.26 (m, 4H), 3.28 (t, 2H, J1=6.4 Hz, J2=7.2 Hz), 3.54 (m, 2H), 3.81 (m, 5H), 3.99 (m, 2H), 4.13 (s, 2H), 5.04 (s, 2H), 6.86 (d, 2H, J1=8.8 Hz, J2=8.8 Hz), 7.24 (m, 2H), 7.36 (d, 1H, J=8.8 Hz), 7.51 (m, 1H), 7.69 (m, 1H), 7.79 (m, 1H), 7.97 (m, 1H), 8.09 (m, 1H).

Example 15

7-Morpholin-4-yl-2-(2-quinolin-2-yl-ethyl)-3,5-dihydro-2H-pyrrolo[3,4-c]pyridine-1,6-dione 5-(4-Methoxy-benzyl)-7-morpholin-4-yl-2-(2-quinolin-2-yl-ethyl)-3,5-dihydro-2H-pyrrolo[3,4-c]pyridine-1,6-dione (30 mg, 0.059 mmol, see Example 14) was dissolved in TFA (30 ml), stirred and heated to about 100° C. for about 12 h. LC-MS analysis indicated complete conversion. The crude material was purified via preparative thin-layer chromatography (MeOH/DCM=10:90) to give the title compound (17 mg, 0.043 mmol, 73.4% yield).

LC-MS (ESI+): m/e 391(M+H)⁺, $R_t$: 1.62 min; ¹H-NMR (CDCl₃, 400 MHz): δ=3.32 (t, 2H, J1=6.8 Hz, J2=6.8 Hz), 3.51 (m, 4H), 3.80 (m, 4H), 4.03 (m, 2H), 4.19 (s, 2H), 6.88 (s, 1H), 7.37 (m, 1H), 7.51 (m, 1H), 7.69 (m, 1H), 7.79 (m, 1H), 8.00 (m, 1H), 8.09 (m, 1H), 11.38 (br, 1H).

Example 16

5-Ethyl-7-morpholin-4-yl-2-(2-quinolin-2-yl-ethyl)-3,5-dihydro-2H-pyrrolo[3,4-c]pyridine-1,6-dione Potassium carbonate (2.5 g, 18.09 mmol), iodoethane (0.103 ml, 1.281 mmol) and 7-morpholin-4-yl-2-(2-quinolin-2-yl-ethyl)-3,5-dihydro-2H-pyrrolo[3,4-c]pyridine-1,6-dione (0.5 g, 1.281 mmol, see Example 15) were suspended in acetonitrile (30 ml). The suspension was heated in a three-neck round bottom flask at about 60° C. for about 2 h. After cooling to r.t. LC-MS analysis indicated complete conversion. The reaction mixture was diluted with water. The aqueous layer was extracted with DCM (2×100 ml). The organic layer was dried over sodium sulfate, filtered and concentrated to give a yellow solid which was purified by preparative HPLC to give the title compound (190 mg, 0.454 mmol, 35.5 yield) as a yellow solid.

LC-MS (ESI+): m/e 419 (M+H)$^+$, $R_t$: 1.75 min; $^1$H-NMR (CDCl$_3$, 400 MHz): δ=1.34 (t, 2H, J1=7.2 Hz, J2=6.8 Hz), 3.31 (t, 2H, J1=7.2 Hz, J2=7.2 Hz), 3.53 (m, 4H), 3.82 (m, 4H), 3.94~4.04 (m, 4H), 4.16 (s, 2H), 6.87 (s, 1H), 7.38 (m, 1H), 7.52 (m, 1H), 7.70 (m, 1H), 7.80 (m, 1H), 7.99 (m, 1H), 8.10 (m, 1H).

The hydrochloride of the title compound was prepared according to standard procedures.

MS (ESI+): m/e 441.20 (M+Na)$^+$, 419.20 (M+H)$^+$.

Example 17

5-Isopropyl-7-morpholin-4-yl-2-(2-quinolin-2-yl-ethyl)-3,5-dihydro-2H-pyrrolo[3,4-c]pyridine-1,6-dione A solution of potassium carbonate (2.5 g, 18.09 mmol), 2-iodopropane (1.0 ml, 10.00 mmol) and 7-morpholin-4-yl-2-(2-quinolin-2-yl-ethyl)-3,5-dihydro-2H-pyrrolo[3,4-c]pyridine-1,6-dione (0.5 g, 1.281 mmol, see Example 15) were dissolved in acetonitrile (30 ml). The suspension was stirred at about 105° C. for about 24 h. After cooling to r.t., LC-MS analysis indicated complete conversion. The crude product was purified by preparative HPLC to afford the title compound (70 mg, 0.162 mmol, 12.64% yield).

LC-MS (ESI+): m/e 433 (M+H)$^+$, $R_t$: 1.83 min; $^1$H-NMR (CDCl$_3$, 400 MHz): δ=1.32 (d, 6H, J=6.8 Hz), 3.33 (s, 2H), 3.53 (m, 4H), 3.82 (m, 4H), 4.03 (t, 2H, J1=7.2 Hz, J2=7.2 Hz), 4.22 (s, 2H), 5.28 (m, 1H), 6.92 (s, 1H), 7.40 (m, 1H), 7.54 (m, 1H), 7.72 (m, 1H), 7.81 (m, 1H), 8.02 (m, 1H), 8.12 (m, 1H).

Example 18

5-(2-Methoxy-ethyl)-7-morpholin-4-yl-2-(2-quinolin-2-yl-ethyl)-3,5-dihydro-2H-pyrrolo[3,4-c]pyridine-1,6-dione A solution of 1-bromo-2-methoxyethane (32.0 mg, 0.231 mmol), potassium carbonate (159 mg, 1.153 mmol) and 7-morpholin-4-yl-2-(2-quinolin-2-yl-ethyl)-3,5-dihydro-2H-pyrrolo[3,4-c]pyridine-1,6-dione (90 mg, 0.231 mmol, see Example 15) were suspended in acetonitrile (50 ml) in a round-bottomed flask. The suspension was stirred at about 120° C. for about 12 h. The obtained crude material was purified by preparative HPLC to give the title compound (5 mg, 0.011 mmol, 4.84% yield).

LC-MS (ESI+): m/e 449 (M+H)$^+$, $R_t$: 1.91 min; $^1$H-NMR (CDCl$_3$, 400 MHz): δ=3.29~3.32 (m, 5H), 3.52 (m, 3H), 3.68 (m, 2H), 3.81 (m, 3H), 4.00-4.09 (m, 4H), 4.20 (s, 2H), 6.95 (s, 1H), 7.38 (m, 1H), 7.53 (m, 1H), 7.70 (m, 1H), 7.80 (m, 1H), 7.99 (m, 1H), 8.10 (m, 1H).

Example 19

5-(2-Hydroxy-ethyl)-7-morpholin-4-yl-2-(2-quinolin-2-yl-ethyl)-3,5-dihydro-2H-pyrrolo[3,4-c]pyridine-1,6-dione Boron tribromide (0.5 ml, 0.445 mmol) and 5-(2-methoxy-ethyl)-7-morpholin-4-yl-2-(2-quinolin-2-yl-ethyl)-3,5-dihydro-2H-pyrrolo[3,4-c]pyridine-1,6-dione (50 mg, 0.111 mmol, see Example 18) were dissolved in DCM (30 ml) in a round-bottomed flask. The reaction was stirred at about 0° C. for about 3 h, diethyl ether and afterwards water were added. The obtained crude material was purified by preparative HPLC to give the title compound (20 mg, 0.046 mmol, 41.3% yield).

LC-MS (ESI+): m/e 435 (M+H)$^+$, $R_t$: 1.62 min; $^1$H-NMR (CDCl$_3$, 400 MHz): δ=3.30 (m, 3H), 3.51 (m, 4H), 3.80 (m, 4H), 3.95-4.08 (m, 4H), 4.09 (m, 2H), 4.18 (s, 2H), 6.93 (s, 1H), 7.37 (m, 1H), 7.52 (m, 1H), 7.69 (m, 1H), 7.79 (m, 1H), 7.98 (m, 1H), 8.10 (m, 1H)

Example 20

5-Methyl-2-[2-(1-methyl-1H-benzoimidazol-2-yl)-ethyl]-7-morpholin-4-yl-3,5-dihydro-2H-pyrrolo[3,4-c]pyridine-1,6-dione Palladium diacetate (189 mg, 0.841 mmol), Xantphos (486 mg, 0.841 mmol) and Cs$_2$CO$_3$ (822 mg, 2.52 mmol) were each rapidly added in sequence to a suspension of 7-chloro-5-methyl-2-[2-(1-methyl-1H-benzoimidazol-2-yl)-ethyl]-3,5-dihydro-2H-pyrrolo[3,4-c]pyridine-1,6-dione (300 mg, 0.841 mmol, see Example c8)) and morpholine (220 mg, 2.52 mmol) in dioxane (1 ml). The reaction was heated in a microwave at about 120° C. for about 40 min. The solvent was removed and the resulting mixture was purified by preparative HPLC (system: Waters 2767 PHW003, eluent: MeCN/ammonium acetate buffer (gradient: 10:90 to 35:65 over 15 min), column: Boston Analytics, C-18, 10 μm, 21×250 mm) to afford the title compound (30 mg, 0.074 mmol, 8.76% yield)

LC-MS (ESI+): m/e 408 (M+H)$^+$, $R_t$: 1.57 min; $^1$H-NMR (400 MHz, CDCl$_3$): δ=3.26 (t, J=7 Hz, 2H); 3.49 (t, J=5 Hz, 7H); 3.78 (t, J=4.2 Hz, 7H); 4.01 (t, J=6.8 Hz, 2H); 4.27 (s, 2H); 6.88 (s, 1H); 7.23-7.32 (m, 3H); 7.67 (d, J=7.2 Hz, 1H).

Example 21

5-Methyl-2-[2-(1-methyl-1H-benzoimidazol-2-yl)-ethyl]-7-pyridin-3-yl-3,5-dihydro-2H-pyrrolo[3,4-c]pyridine-1,6-dione K$_2$CO$_3$ (232 mg, 1.682 mmol) and bis(triphenylphosphine) palladium(II) dichloride (39.3 mg, 0.056 mmol) were each rapidly added in sequence to a suspension of 7-chloro-5-methyl-2-[2-(1-methyl-1H-benzoimidazol-2-yl)-ethyl]-3,5-dihydro-2H-pyrrolo[3,4-c]pyridine-1,6-dione (200 mg, 0.561 mmol, see Example c8) and pyridin-3-ylboronic acid (103 mg, 0.841 mmol) in DMF (3 ml)/water (0.600 ml). The reaction was heated in a microwave at about 120° C. for about 20 min. The reaction was cooled to r.t., DCM (15 ml) and DMF (1 ml) were added, the resulting mixture was filtered and the filtrate was concentrated by evaporating DCM. The concentrate was cooled to r.t., the crystallized solid was filtered off, washed with water and dried to afford the title compound (50 mg, 0.125 mmol, 22.33% yield).

LC-MS (ESI+): m/e 400 (M+H)$^+$, $R_t$: 1.54 min; $^1$H-NMR (400 MHz, MeOD-d4): δ=3.25 (t, J=6.8 Hz, 2H); 3.55 (s, 3H); 3.74 (s, 3H); 3.88 (t, J=6.8 Hz, 2H); 4.32 (s, 2H); 7.11-7.22 (m, 3H); 7.37-7.44 (m, 3H); 7.83 (s, 1H); 8.31 (s, 2H).

Example 22

2-(2-Imidazo[1,2-a]pyridin-2-yl-ethyl)-5-methyl-7-morpholin-4-yl-3,5-dihydro-2H-pyrrolo[3,4-c]pyridine-1,6-dione Palladium diacetate (65.5 mg, 0.292 mmol), Xantphos (169 mg, 0.292 mmol) and Cs$_2$CO$_3$ (285 mg, 0.875 mmol)

were each rapidly added in sequence to a suspension of 7-chloro-2-(2-imidazo[1,2-a]pyridin-2-yl-ethyl)-5-methyl-3,5-dihydro-2H-pyrrolo[3,4-c]pyridine-1,6-dione (100 mg, 0.292 mmol, see Example c5)) and morpholine (76 mg, 0.875 mmol) in dioxane (1 ml). The reaction was heated in a microwave at about 120° C. for about 40 min. The solvent was removed and the resulting mixture was purified by preparative HPLC (system: Waters 2767 PHW003, eluent: MeCN/ammonium acetate buffer (gradient: 10:90 to 35:65 over 15 min), column: Boston Analytics, C-18, 10 µm, 21×250 mm) to afford the title compound (24.1 mg, 0.061 mmol, 21.00% yield).

LC-MS (ESI+): m/e 394 (M+H)+, $R_t$: 1.50 min; $^1$H-NMR (400 MHz, CDCl$_3$): δ=3.12 (t, J=7.2 Hz, 2H); 3.51 (s, 3H); 3.58 (t, J=4.6 Hz, 4H); 3.84 (t, J=4.4 Hz, 4H); 3.91 (t, J=7 Hz, 2H); 4.15 (s, 2H); 6.75 (t, J=6.6 Hz, 1H); 6.89 (s, 1H); 7.13-7.17 (m, 1H); 7.44 (s, 1H); 7.51 (d, J=9.2 Hz, 1H); 8.05 (d, J=6.8 Hz, 1H).

Example 23

2-(2-Imidazo[1,2-a]pyridin-2-yl-ethyl)-5-methyl-7-morpholin-4-yl-3,5-dihydro-2H-pyrrolo[3,4-c]pyridine-1,6-dione K$_2$CO$_3$ (121 mg, 0.875 mmol) and bis(triphenylphosphine)palladium(II) dichloride (20.48 mg, 0.029 mmol) were each rapidly added in sequence to a suspension of 7-chloro-2-(2-imidazo[1,2-a]pyridin-2-yl-ethyl)-5-methyl-3,5-dihydro-2H-pyrrolo[3,4-c]pyridine-1,6-dione (100 mg, 0.292 mmol, see Example c5)) and pyridin-3-ylboronic acid (53.8 mg, 0.438 mmol) in DMF (1 ml)/water (0.200 ml). The reaction mixture was heated in a microwave at about 120° C. for about 20 min. The reaction was cooled to r.t. DCM (15 ml) and DMF (1 ml) were added, the resulting mixture was filtered and the filtrate was concentrated by evaporating DCM. The concentrate was cooled to r.t., the crystallized solid was filtered and dried to afford the title compound (40 mg, 0.104 mmol, 35.6% yield).

LC-MS (ESI+): m/e 386 (M+H)+, $R_t$: 1.44 min; $^1$H-NMR (400 MHz, CDCl$_3$): δ=3.14 (t, J=7 Hz, 2H); 3.63 (s, 3H); 3.96 (t, J=7 Hz, 2H); 4.25 (s, 2H); 6.75 (t, J=6.6 Hz, 1H); 7.16 (t, J=7.8 Hz, 1H); 7.31-7.35 (m, 1H); 7.43 (d, J=7.6 Hz, 2H); 7.51 (d, J=8.8 Hz, 1H); 7.82-7.85 (m, 1H); 8.05 (d, J=6.8 Hz, 1H); 8.58 (dd, J=4.6 Hz, 1H); 8.68 (d, J=2.4 Hz, 1H).

Example 24

5-Methyl-7-morpholin-4-yl-2-(2-[1,2,4]triazolo[1,5-a]pyridin-2-yl-ethyl)-3,5-dihydro-2H-pyrrolo[3,4-c]pyridine-1,6-dione Palladium diacetate (65.3 mg, 0.291 mmol), Xantphos (168 mg, 0.291 mmol) and Cs$_2$CO$_3$ (284 mg, 0.873 mmol) were each rapidly added in sequence to a suspension of 7-chloro-5-methyl-2-(2-[1,2,4]triazolo[1,5-a]pyridin-2-yl-ethyl)-3,5-dihydro-2H-pyrrolo[3,4-c]pyridine-1,6-dione (100 mg, 0.291 mmol, see Example c6)) and morpholine (25.3 mg, 0.291 mmol) in dioxane (5 ml). The reaction mixture was heated in a microwave at about 120° C. for about 40 min. The solvent was removed and the resulting mixture was purified by preparative HPLC (system: Waters 2767 PHW003, eluent: MeCN/ammonium acetate buffer (gradient: 7:93 to 30:70 over 15 min), column: Boston Analytics, C-18, 10 µm, 10×250 mm) to afford the title compound (17 mg, 0.043 mmol, 14.82% yield).

LC-MS (ESI+): m/e 395 (M+H)+, $R_t$: 1.43 min; $^1$H-NMR (400 MHz, CDCl$_3$): δ=3.18 (t, J=7 Hz, 2H); 3.45 (s, 3H); 3.49 (t, J=4.6 Hz, 4H); 3.75 (t, J=4.2 Hz, 4H); 3.95 (t, J=6.8 Hz, 2H); 4.12 (s, 2H); 6.82 (s, 1H); 6.92 (t, J=6.8 Hz, 1H); 7.43 (t, J=8 Hz, 1H); 7.59 (d, J=9.2 Hz, 1H); 8.43 (d, J=6.8 Hz, 1H).

Example 25

5-Methyl-7-morpholin-4-yl-2-[2-(5,6,7,8-tetrahydro-[1,2,4]triazolo[1,5-a]pyridin-2-yl)-ethyl]-3,5-dihydro-2H-pyrrolo[3,4-c]pyridine-1,6-dione The title compound was prepared in analogy to the processes of Examples c6) and 24.

$^1$H NMR (500 MHz, DMSO-d6): δ=7.42 (s br, 1H), 4.22 (s, 2H), 4.00 (t, 2H), 3.64-3.68 (m, 6H), 3.42 (s, 3H), 3.37 (m, 4H), 2.82 (t, 2H), 2.74 (t, 2H), 1.94 (m br, 2H), 1.85 (m br, 2H).

Example 26

5-Methyl-7-pyridin-3-yl-2-(2-[1,2,4]triazolo[1,5-a]pyridin-2-yl-ethyl)-3,5-dihydro-2H-pyrrolo[3,4-c]pyridine-1,6-dione K$_2$CO$_3$ (60.3 mg, 0.436 mmol) and bis(triphenylphosphine)palladium(II) dichloride (10.21 mg, 0.015 mmol) were each rapidly added in sequence to a suspension of 7-chloro-5-methyl-2-(2-[1,2,4]triazolo[1,5-a]pyridin-2-yl-ethyl)-3,5-dihydro-2H-pyrrolo[3,4-c]pyridine-1,6-dione (50 mg, 0.145 mmol, see Example c6)) and pyridin-3-ylboronic acid (19.67 mg, 0.160 mmol) in DMF (1 ml)/water (0.200 ml). The reaction mixture was heated in a microwave at about 120° C. for about 20 min. The mixture was purified by preparative HPLC (system: Waters 2767 PHW003, eluent: MeCN/ammonium acetate buffer (gradient: 5:95 to 30:70 over 15 min), column: Boston Analytics, C-18, 10 µm, 21×250 mm) to afford the title compound (25 mg, 0.065 mmol, 44.5% yield).

LC-MS (ESI+): m/e 387 (M+H)+, $R_t$: 1.37 min; $^1$H-NMR (400 MHz, CDCl$_3$): δ=3.26 (t, J=6.6 Hz, 2H); 3.64 (s, 3H); 4.05 (t, J=7 Hz, 2H); 4.32 (s, 2H); 6.98-7.02 (m, 1H); 7.30-7.33 (m, 1H); 7.46 (s, 1H); 7.49-7.53 (m, 1H); 7.67 (d, J=9.2 Hz, 1H); 7.80-7.83 (m, 1H); 8.50 (d, J=6.8 Hz, 1H); 8.56 (dd, J=4.6 Hz, 1H); 8.67 (d, J=2 Hz, 1H).

Example 27

7-(4-Fluoro-phenyl)-5-methyl-2-(2-quinolin-2-yl-ethyl)-3,5-dihydro-2H-pyrrolo[3,4-c]pyridine-1,6-dione The title compound was prepared in analogy to the process of Example 13 starting from 7-chloro-5-methyl-2-(2-quinolin-2-yl-ethyl)-3,5-dihydro-2H-pyrrolo[3,4-c]pyridine-1,6-dione (see Example c4)) and 4-fluorophenylboronic acid.

MS (ESI+): m/e 414.10 (M+H)+.

Example 28

5-Methyl-7-pyrimidin-5-yl-2-(2-quinolin-2-yl-ethyl)-3,5-dihydro-2H-pyrrolo[3,4-c]pyridine-1,6-dione The title compound was prepared in analogy to the process of Example 13 starting from 7-chloro-5-methyl-2-(2-quinolin-2-yl-ethyl)-3,5-dihydro-2H-pyrrolo[3,4-c]pyridine-1,6-dione (see Example c4)) and pyrimidin-5-ylboronic acid.

MS (ESI+): m/e 398.10 (M+H)+.

Example 29

5-Methyl-7-(1H-pyrazol-4-yl)-2-(2-quinolin-2-yl-ethyl)-3,5-dihydro-2H-pyrrolo[3,4-c]pyridine-1,6-dione The title compound was prepared in analogy to the process of Example 13 starting from 7-chloro-5-methyl-2-(2-quinolin-2-yl-ethyl)-3,5-dihydro-2H-pyrrolo[3,4-c]pyridine-1,6-dione (see Example c4)) and 1H-pyrazol-4-ylboronic acid.

$^1$H NMR (500 MHz, DMSO-d6): δ=12.80 (br. s., 1H), 8.40 (br. s., 1H), 8.29 (d, 2H), 7.93 (d, 2H), 7.81 (s, 1H), 7.71 (t, 1H), 7.56 (t, 1H), 7.49 (d, 1H), 4.30 (s, 2H), 3.97 (t, 2H), 3.52 (s, 3H), 3.27 (t, 2H).

Example 30

5-Methyl-7-(2-methyl-2H-pyrazol-3-yl)-2-(2-quinolin-2-yl-ethyl)-3,5-dihydro-2H-pyrrolo[3,4-c]pyridine-1,6-dione The title compound was prepared in analogy to the process of Example 13 starting from 7-chloro-5-methyl-2-(2-quinolin-2-yl-ethyl)-3,5-dihydro-2H-pyrrolo[3,4-c]pyridine-1,6-dione (see Example c4)) and 2-methyl-2H-pyrazol-3-ylboronic acid.

$^1$H NMR (500 MHz, DMSO-d6): δ=8.28 (d, 1H), 8.12 (s, 1H), 7.93 (d, 1H), 7.89 (d, 1H), 7.71 (t, 1H), 7.55 (t, 1H), 7.46 (d, 1H), 7.34 (s, 1H), 6.08 (s, 1H), 4.39 (br. m., 2H), 3.92 (br. m., 2H), 3.53 (s, 3H), 3.34 (s, 3H), 3.25 (t, 2H).

Example 31

7-(4-Methoxy-phenyl)-5-methyl-2-(2-quinolin-2-yl-ethyl)-3,5-dihydro-2H-pyrrolo[3,4-c]pyridine-1,6-dione The title compound was prepared in analogy to the process of Example 13 starting from 7-chloro-5-methyl-2-(2-quinolin-2-yl-ethyl)-3,5-dihydro-2H-pyrrolo[3,4-c]pyridine-1,6-dione (see Example c4)) and 4-methoxyphenylboronic acid.

MS (ESI+): m/e 426.20 (M+H)$^+$.

Example 32

2-[2-(1,3-benzothiazol-2-yl)ethyl]-5-methyl-7-(4-pyridyl)-3,5-dihydro-2H-pyrrolo[3,4-c]pyridine-1,6-dione The title compound was prepared in analogy to the processes of Examples c8) and 21.

MS (ESI+): m/e 403.10 (M+H)$^+$.

Example 33

2-[2-(1,3-benzothiazol-2-yl)ethyl]-5-methyl-7-morpholin-4-yl-3,5-dihydro-2H-pyrrolo[3,4-c]pyridine-1,6-dione The title compound was prepared in analogy to the processes of Examples c8) and 20.

MS (ESI+): m/e 411.10 (M+H)$^+$.

Example 34

2-(2,2-Difluoro-2-quinolin-2-yl-ethyl)-5-methyl-7-morpholin-4-yl-3,5-dihydro-2H-pyrrolo[3,4-c]pyridine-1,6-dione The title compound was prepared in analogy to the processes of Examples 1 and 9.

MS (ESI+): m/e 463.10 (M+Na)$^+$, 441.10 (M+H)$^+$.

Example 35

3,3-Difluoro-5-methyl-7-morpholin-4-yl-2-(2-quinolin-2-yl-ethyl)-3,5-dihydro-2H-pyrrolo[3,4-c]pyridine-1,6-dione The title compound was prepared in analogy to the processes of Examples c1) and 1 as well as standard procedures.

MS (ESI+): m/e 441.10 (M+H)$^+$.

Comparative Example

2-Ethyl-5-methyl-7-morpholin-4-yl-5H-pyrrolo[3,4-c]pyridine-1,3,6-trione

The title compound was prepared in analogy to the processes of Examples c1) and 1.

MS (ESI+): m/e 314.10 (M+Na)$^+$, 292.10 (M+H)$^+$.

Biological Tests a) Measurement of PDE Activity

The recombinant PDE proteins are used in in vitro enzymatic reaction for measurement of PDE activity. These recombinant proteins, including PDE10A (human, rat and mouse PDE10) and isoforms of PDEs 1, 3, 4, and 5, were purchased from commercial vendor BPS Bioscience. The enzymatic activity of PDEs was determined by cAMP measurement kit from CisBio (IBA) using HTRF technology.

The PDE enzymatic reaction was carried out in assay buffer (20 mM Tris-HCl pH7.5, 10 mM MgCl$_2$, 0.1% bovine serum albumin) containing enzyme and substrate. The PDE enzymes concentration ranged from 10 pM-250 pM, depending on each enzyme's specific activity. The substrate cyclic nucleotide (cAMP or cGMP) concentration used in the assay was 20 nM for PDE10, and 100 nM for other PDEs. The inhibitory effect of compound was determined by incubating various concentration of inhibitor in the enzymatic assay. Typically, compound was serial diluted in DMSO then further diluted in assay buffer. Next, the compound at varying concentration was mixed with PDE enzyme. The reaction was initiated by addition of cyclic nucleotide substrate, and incubated for 60 minutes at 29 C. The reaction was stopped by addition of lysis buffer from assay kit. The cAMP-d2 and anti-cAMP cryptate in the lysis buffer detected the level of cAMP left from the PDE hydrolysis reaction. The PDE activity is reversely correlated with the amount of cAMP left in the reaction and can be converted to the percent activity of an uninhibited control (100%). Thus, IC$_{50}$ value of inhibitor can be obtained by plotting inhibitor concentration against PDE activity at that concentration. The results are shown in Table 1.

TABLE 1

| Example | IC$_{50}$[1) |
|---|---|
| 1 | +++ |
| 5 | ○ |
| 6 | ○ |
| 7 | ○ |
| 8 | ○ |
| 9 | +++ |
| 11 | ++ |
| 12 | ++ |
| 13 | ○ |
| 14 | +++ |
| 15 | +++ |
| 16 | +++ |
| 17 | +++ |
| 18 | +++ |
| 19 | +++ |
| 20 | +++ |
| 21 | + |
| 22 | +++ |
| 23 | ○ |
| 24 | ○ |
| 25 | ○ |
| 26 | ○ |
| 27 | ++ |
| 28 | ++ |
| 29 | ○ |
| 30 | ○ |
| 31 | ++ |
| 32 | ○ |
| 33 | ++ |
| 34 | +++ |
| 35 | +++ |

[1)]+++: IC$_{50}$ < 100 nM ++: 100 nM ≤ IC$_{50}$ ≤ 200 nM +: 200 nM < IC$_{50}$ ≤ 500 nM ○: IC$_{50}$ > 500 nM b) Determination of the Microsomal Half-Life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomoleculur Screening, 2003, 453-462; Obach, D M D, 1999 vol 27. N 11, 1350-1359). The results are shown in Table 2.

TABLE 2

| Example | Rat mCl[2)] [µl min$^{-1}$ mg$^{-1}$] | Human mCl[2)] [µl min$^{-1}$ mg$^{-1}$] |
|---|---|---|
| 1 | ++ | ++ |
| 5 | +++ | +++ |
| 6 | ++ | ++ |
| 7 | +++ | ++ |
| 9 | ++ | ++ |
| 10 | +++ | +++ |
| 12 | +++ | ++ |
| 13 | ++ | ++ |
| 14 | + | ○ |
| 15 | ++ | ++ |
| 16 | ++ | ++ |
| 17 | ++ | ++ |
| 18 | ++ | ++ |
| 19 | +++ | ++ |
| 20 | ++ | ++ |
| 21 | ++ | ++ |
| 22 | ++ | +++ |
| 23 | +++ | +++ |
| 24 | ++ | ++ |
| 25 | +++ | +++ |
| 26 | ++ | +++ |
| 27 | ++ | +++ |
| 28 | ++ | ++ |
| 29 | ++ | +++ |
| 31 | ++ | ++ |
| 32 | +++ | +++ |
| 33 | +++ | +++ |
| 34 | ++ | ++ | mCl microsomal clearance

[2)]+++ <10 µl min$^{-1}$ mg$^{-1}$ ++: <100 µl min$^{-1}$ mg$^{-1}$ +: 100-220 µl min$^{-1}$ mg$^{-1}$ ○: >220 µl min$^{-1}$ mg$^{-1}$

We claim:
1. A compound of formula I

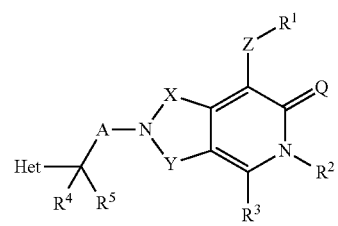

wherein

X is CR$^{x1}$R$^{x2}$ or C(O), where
 R$^{x1}$ and R$^{x2}$, independently of each other are selected from the group consisting of hydrogen, halogen, C$_1$-C$_4$-alkyl, trimethylsilyl, C$_1$-C$_4$-fluoroalkyl, C$_1$-C$_4$-fluoroalkoxy, C$_3$-C$_6$-cycloalkyl, optionally substituted by 1, 2 or 3 methyl groups, and fluorinated C$_3$-C$_6$-cycloalkyl, or the radicals R$^{x1}$ and R$^{x2}$, together with the carbon atom to which they are bound, form a saturated 3- to 6-membered carbocycle or a saturated 3- to 6-membered heterocycle having 1 or 2 non-adjacent heteroatoms, which are independently selected from the group consisting of O, S and N, as ring members, where the carbocycle and the heterocycle are unsubstituted or may carry 1, 2, 3 or 4 substituents independently selected from the group consisting of fluorine and methyl;

Y is CR$^{y1}$R$^{y2}$ or C(O), where
 R$^{y1}$ and R$^{y2}$, independently of each other are selected from the group consisting of hydrogen, halogen, C$_1$-C$_4$-alkyl, trimethylsilyl, C$_1$-C$_4$-fluoroalkyl, C$_1$-C$_4$-fluoroalkoxy, C$_3$-C$_6$-cycloalkyl, optionally substituted by 1, 2 or 3 methyl groups, and fluorinated C$_3$-C$_6$-cycloalkyl or the radicals R$^{y1}$ and R$^{y2}$, together with the carbon atom to which they are bound, form a saturated 3- to 6-membered carbocycle or a saturated 3- to 6-membered heterocycle having 1 or 2 non-adjacent heteroatoms, which are independently selected from the group consisting of O, S and N, as ring members, where the carbocycle and the heterocycle are unsubstituted or may carry 1, 2, 3 or 4 substituents independently selected from the group consisting of fluorine and methyl;

provided that one or both of X and Y is/are C(O);

A is O, $[C(R^6,R^7)]_k$ with k=1 or 2, $OC(R^6,R^7)$, $C(R^8)$=$C(R^9)$ or C≡C;

Het is independently selected from the group consisting of
  i. monocyclic 5- or 6-membered hetaryl having 1 or 2 nitrogen atoms and optionally a further heteroatom selected from the group consisting of O, S and N as ring members, which is unsubstituted or may carry 1, 2, 3 or 4 identical or different substituents $R^a$,
  ii. fused 8-, 9- or 10-membered bicyclic hetaryl having one heteroatom selected from the group consisting of O, S and N and optionally 1, 2 or 3 nitrogen atoms as ring members, where the fused bicyclic hetaryl is unsubstituted or may carry 1, 2, 3 or 4 identical or different substituents $R^a$, and
  iii. phenyl, which carries a monocyclic hetaryl radical having 1 or 2 nitrogen atoms and optionally a further heteroatom selected from the group consisting of O, S and N as ring members, which in addition to monocyclic hetaryl, may carry 1, 2 or 3 identical or different substituents $R^{aa}$, and where hetaryl is unsubstituted or carries 1, 2 or 3 radicals $R^a$;

$R^a$ is independently selected from the group consisting of halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, cyclopropyl substituted by 1, 2 or 3 methyl groups, fluorinated $C_3$-$C_6$-cycloalkyl, O—$C_3$-$C_6$-cycloalkyl, benzyloxy, C(O)O—($C_1$-$C_4$-alkyl), O—($C_1$-$C_4$-alkyl)-$CO_2H$, $C_1$-$C_4$-alkyl-$OR^{11}$, $C_1$-$C_4$-alkyl-$SR^{12}$, $C_1$-$C_4$-alkyl-$NR^{13}R^{14}$, $C_1$-$C_6$-alkoxy, $OC_1$-$C_4$-alkyl-$OR^{11}$, $OC_1$-$C_4$-alkyl-$SR^{12}$, $OC_1$-$C_4$-alkyl-$NR^{13}R^{14}$, $NR^{13}R^{14}$, C(O)$NR^{13}R^{14}$, $C_1$-$C_4$-alkyl-$NR^{13}R^{14}$, —$NR^{15}$—C(O)—$NR^{13}R^{14}$, $NR^{15}$—C(O)O—($C_1$-$C_4$-alkyl), —$NR^{15}$—$SO_2$—$R^{12}$, CN, —$SF_5$, —$OSF_5$, —$SO_2R^{12}$, —$SR^{12}$ and trimethylsilyl, or
  two radicals $R^a$, which are bound to adjacent ring atoms may also form linear $C_3$-$C_5$ alkanediyl, wherein 1 or 2 CH$_2$ moieties can be replaced by C=O, O, S, S(=O), S(=O)$_2$ or NR', and where alkanediyl is unsubstituted or may carry 1 or 2 radicals independently selected from the group consisting of halogen, $C_1$-$C_4$-alkyl, $C_1$-$C_4$-fluoroalkyl, $C_1$-$C_4$-alkoxy, and $C_1$-$C_4$-fluoroalkoxy;

$R^{aa}$ has one of the meanings given for $R^a$ or one radical $R^{aa}$ may also be phenyl or a 5- or 6-membered hetaryl having 1 or 2 nitrogen atoms and optionally a further heteroatom independently selected from the group consisting of O, S and N as ring members, where phenyl and hetaryl are unsubstituted or may carry 1, 2 or 3 radicals independently selected from the group consisting of halogen, OH, $C_1$-$C_4$-alkyl, $C_1$-$C_4$-haloalkyl, $C_1$-$C_4$-alkoxy and $C_1$-$C_4$-haloalkoxy;

Q is O or S;

Z is independently selected from the group consisting of a chemical bond, CH$_2$, O, O—CH$_2$, C(O)O, C(O), NR$^2$, NR$^2$—CH$_2$, S(O)$_2$—NR$^2$, C(O)—NR$^2$, S, S(O), S(O)$_2$, C(O)—O—CH$_2$, C(O)—NR$^2$—CH$_2$, 1,2-ethanediyl, 1,2-ethenediyl and 1,2-ethynediyl, where R$^2$ is selected from the group consisting of hydrogen, $C_1$-$C_4$-alkyl, $C_1$-$C_4$-alkylcarbonyl, $C_1$-$C_4$-alkylsulfonyl, and $C_1$-$C_4$-fluoroalkylsulfonyl;

$R^1$ is independently selected from the group consisting of phenyl, naphthyl, $C_3$-$C_3$-cycloalkyl, 3- to 8-membered saturated or partially unsaturated heteromonocyclic radicals, saturated or partially unsaturated 7- to 10-membered heterobicyclic radicals, 5- or 6-membered monocyclic hetaryl, and 8- to 10-membered bicyclic hetaryl, where the saturated or partially unsaturated heteromonocyclic and heterobicyclic radicals have 1, 2, 3 or 4 heteroatoms or heteroatom containing groups as ring members, which are selected from the group consisting of O, S, SO, SO$_2$ and N, and where the 5- or 6-membered monocyclic hetaryl and the 8- to 10-membered bicyclic hetaryl have 1, 2, 3 or 4 heteroatoms as ring members, which are selected from the group consisting of O, S and N, where $C_3$-$C_3$-cycloalkyl, the saturated or partially unsaturated heteromonocyclic and heterobicyclic radicals are unsubstituted or carry 1, 2, 3, 4 or 5 radicals $R^{C1}$ or one radical Y'—$R^{C2}$ and 0, 1, 2, 3 or 4 radicals $R^{C1}$;

where phenyl, naphthyl, the mono and bicyclic heteroaromatic radicals are unsubstituted or carry 1, 2, 3, 4 or 5 radicals $R^{C3}$ or one radical Y'—$R^{C2}$ and 0, 1, 2, 3 or 4 radicals $R^{C1}$; where $R^{C1}$ is independently selected from the group consisting of halogen, OH, CN, NO$_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$-alkyl, $C_1$-$C_4$-fluoroalkyl, $C_1$-$C_4$-fluoroalkoxy, $C_1$-$C_4$-alkylsulfonyl, C(O)$R^h$, Z'—C(O)O$R^b$, Z'—C(O)N$R^cR^d$, N$R^g$SO$_2R^h$, S(O)$_2$N$R^cR^d$ and Z'—N$R^eR^f$, where $R^b$, $R^g$ independently of each other are selected from the group consisting of hydrogen, $C_1$-$C_4$-alkyl, $C_2$-$C_4$-alkenyl and $C_1$-$C_4$-fluoroalkyl, $R^c$, $R^d$ independently of each other are selected from the group consisting of hydrogen, $C_1$-$C_4$-alkyl, $C_1$-$C_4$-fluoroalkyl, $C_1$-$C_4$-alkoxy and $C_1$-$C_4$-fluoroalkoxy, $R^e$, $R^f$ independently of each other are selected from the group consisting of hydrogen, $C_1$-$C_4$-alkyl, $C_1$-$C_4$-fluoroalkyl, $C_1$-$C_4$-hydroxyalkyl, $C_1$-$C_4$-alkoxy-$C_1$-$C_4$-alkyl, $C_1$-$C_4$-alkoxy and $C_1$-$C_4$-fluoroalkoxy, $R^h$ is independently selected from the group consisting of $C_1$-$C_4$-alkyl and $C_1$-$C_4$-fluoroalkyl, Z' is a covalent bond or $C_1$-$C_4$-alkanediyl, or two radicals $R^{C1}$ which are bound at adjacent carbon atoms may form a fused 5- or 6-membered carbocyclic radical or a fused 5- or 6-membered heterocyclic radical having 1, 2 or 3 heteroatoms as ring members, which are independently selected from the group consisting of O, S and N;

or two radicals $R^{C1}$ which are bound at the same carbon atom may form a spiro 5- or 6-membered carbocyclic radical or a spiro 5- or 6-membered heterocyclic radical having 1 or 2 heteroatoms as ring members, which are independently selected from the group consisting of O, S and N, or two radicals $R^{C1}$ which are bound at the same carbon atom may form an oxygen atom, where the fused and the spiro radicals are unsubstituted or carry 1, 2, 3 or 4 radicals $R^{C1}$;

Y' is a chemical bond, CH$_2$, O, O—CH$_2$, C(O), S(O)$_2$, N$R^{y'}$, N$R^{y'}$—CH$_2$ or N$R^{y'}$—S(O)$_2$, where $R^{y'}$ is independently selected from the group consisting of hydrogen, $C_1$-$C_4$-alkyl, $C_1$-$C_4$-alkylcarbonyl, $C_1$-$C_4$-alkylsulfonyl and $C_1$-$C_4$-fluoroalkylsulfonyl;

$R^{C2}$ is a carbocyclic or heterocyclic radical independently selected from the group consisting of phenyl, 3- to 7-membered saturated or partially unsaturated monocarbocyclic radicals, 3- to 7-membered saturated or partially unsaturated heteromonocyclic radicals, having 1, 2 or 3 heteroatoms as ring members, which are selected from the group consisting of O, S and N, and 5- or 6-membered heteroaromatic radicals, having 1, 2 or 3 heteroatoms as ring members, which are independently selected from the group consisting of O, S and N, where the carbocyclic and the heterocyclic radical are unsubstituted or carry 1, 2, 3, 4 or 5 radicals $R^{C4}$;

$R^{C3}$ is independently selected from the group consisting of halogen, OH, CN, $NO_2$, $C_1$-$C_4$-alkyl, $C_1$-$C_4$-alkoxy, $C_1$-$C_4$-alkylsulfanyl, hydroxy-$C_1$-$C_4$-alkyl, $C_1$-$C_4$-alkoxy-$C_1$-$C_4$-alkyl, $C_1$-$C_4$-alkoxy-$C_1$-$C_4$-alkoxy, cyano-$C_1$-$C_4$ alkyl, $C_1$-$C_4$-fluoroalkyl, $C_1$-$C_4$-fluoroalkoxy, $C_1$-$C_4$-alkylsulfonyl, $C(O)R^h$, $Z'$—$C(O)OR^b$, $Z'$—$C(O)NR^cR^d$, $NR^gSO_2R^h$, $S(O)_2NR^cR^d$ and $Z'$—$NR^eR^f$, or two radicals $R^{C3}$ which are bound at adjacent carbon atoms may form a saturated or partially unsaturated fused 5- or 6-membered carbocyclic radical or a saturated or partially unsaturated fused 5- or 6-membered heterocyclic radical having 1, 2 or 3 heteroatoms as ring members, which are independently selected from the group consisting of O, S and N, where the carbocyclic and the heterocyclic radical are unsubstituted or carry 1, 2, 3, 4 or 5 radicals $R^{C4}$;

$R^{C4}$ is independently selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^h$, benzyl, $Z'$—$C(O)OR^b$, $Z'$—$C(O)NR^cR^d$, $S(O)_2NR^cR^d$ and $Z'$—$NR^eR^f$, or two radicals $R^{C4}$ which are bound at the same atom may form an oxygen atom;

$R^2$ is independently selected from the group consisting of hydrogen, $C_1$-$C_6$-alkyl, $C_2$-$C_6$-alkenyl, $C_2$-$C_6$-alkynyl, $C_1$-$C_4$-alkyl-CN, $C_1$-$C_4$-alkyl-$OR^{21}$, $C_1$-$C_4$-alkyl-$SR^{22}$, $C_1$-$C_4$-alkyl-$NR^{23}R^{24}$, $C_1$-$C_6$-fluoroalkyl, $C_3$-$C_6$-cycloalkyl, $C_3$-$C_6$-cycloalkyl-$C_1$-$C_4$-alkyl, where the cycloalkyl moiety in the last two radicals is unsubstituted, partially or completely fluorinated, or substituted by 1, 2 or 3 methyl groups, phenyl, phenyl-$C_1$-$C_4$-alkyl, 5- or 6-membered hetaryl and 5- or 6-membered hetaryl-$C_1$-$C_4$-alkyl, where hetaryl has 1 heteroatom selected from the group consisting of O, S and N as ring member and 0, 1 or 2 further N atoms as ring members, and wherein phenyl and hetaryl in the last four mentioned radicals are unsubstituted or carry 1 or 2 radicals independently selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, $C(O)R^h$, benzyl, $Z'$—$C(O)OR^b$, $Z$—$C(O)NR^cR^d$, $S(O)_2NR^cR^d$ and $Z'$—$NR^eR^f$;

$R^3$ is independently selected from the group consisting of hydrogen, halogen, $C_1$-$C_4$-alkyl, $C_1$-$C_4$-alkoxy, $C_1$-$C_4$-fluoroalkyl, $C_1$-$C_4$-fluoroalkoxy, $C_3$-$C_6$-cycloalkyl, cyclopropyl substituted by 1, 2 or 3 methyl groups, fluorinated cyclopropyl, OH, hydroxy-$C_1$-$C_4$-alkyl, O—$C_3$-$C_6$-cycloalkyl, benzyloxy, $C(O)O$—$(C_1$-$C_4$-alkyl), O—$(C_1$-$C_4$-alkyl)-$CO_2H$, $C_1$-$C_4$-alkyl-$OR^{31}$, $C_1$-$C_4$-alkyl-$SR^{32}$, $C_1$-$C_4$-alkyl-$NR^{33}R^{34}$, $OC_1$-$C_4$-alkyl-$OR^{11}$, $OC_1$-$C_4$-alkyl-$SR^{32}$, $OC_1$-$C_4$-alkyl-$NR^{33}R^{34}$, $NR^{33}R^{34}$, $C(O)NR^{33}R^{34}$, $C_1$-$C_4$-alkyl-$NR^{33}R^{34}$, —$NR^{35}$—$C(O)$—$NR^{33}R^{34}$, $NR^{35}$—$C(O)$$O$—$(C_1$-$C_4$-alkyl), —$NR^{35}$—$SO_2$—$R^{32}$, phenyl, CN, —$SF_5$, —$OSF_5$, —$SO_2R^{32}$, —$SR^{32}$ and trimethylsilyl;

$R^4$, $R^5$ independently of each other are selected from the group consisting of hydrogen, halogen, $C_1$-$C_4$-alkyl, trimethylsilyl, $C_1$-$C_4$-fluoroalkyl, $C_1$-$C_4$-alkoxy, $C_1$-$C_4$-fluoroalkoxy, and $C_3$-$C_6$-cycloalkyl, or the radicals $R^4$, $R^5$ together with the carbon atom to which they are bound form a saturated 3- to 6-membered carbocycle or a saturated 3- to 6-membered heterocycle having 1 or 2 non-adjacent heteroatoms, which are independently selected from the group consisting of O, S and N, as ring members, where the carbocycle and the heterocycle are unsubstituted or may carry 1, 2, 3 or 4 substituents selected from the group consisting of fluorine and methyl;

$R^6$, $R^7$ independently of each other are selected from the group consisting of hydrogen, halogen, $C_1$-$C_4$-alkyl, trimethylsilyl, $C_1$-$C_4$-fluoroalkyl, $C_1$-$C_4$-alkoxy, $C_1$-$C_4$-fluoroalkoxy, and $C_3$-$C_6$-cycloalkyl, or the radicals $R^6$, $R^7$ together with the carbon atom to which they are bound form a saturated 3- to 6-membered carbocycle or a saturated 3- to 6-membered heterocycle having 1 or 2 non-adjacent heteroatoms, which are independently selected from the group consisting of O, S and N, as ring members, where the carbocycle and the heterocycle are unsubstituted or may carry 1, 2, 3 or 4 substituents selected from the group consisting of fluorine and methyl;

$R^8$, $R^9$ independently of each other are selected from the group consisting of hydrogen, halogen, $C_1$-$C_4$-alkyl and $C_1$-$C_4$-fluoroalkyl, the moiety $C(R^4,R^5)$-A may also form a moiety $C(R^8)$=$C(R^9)$, C≡C, $C(R^8)$=$C(R^9)$—$C(R^6,R^7)$ or C≡C—$C(R^6,R^7)$, the moiety $C(R^4,R^5)$-A may also form a cyclopropane-1,2-diyl or cyclopropane-1,2-diyl-$C(R^6,R^7)$, where the cyclopropane-1,2-diyl moiety is unsubstituted or carries 1 or 2 radicals independently selected from the group consisting of halogen, $C_1$-$C_4$-alkyl, trimethylsilyl, $C_1$-$C_4$-fluoroalkyl, $C_1$-$C_4$-alkoxy and $C_1$-$C_4$-fluoroalkoxy;

and where $R^{11}$, $R^{12}$, $R^{21}$, $R^{22}$, $R^{31}$ and $R^{32}$ independently of each other are selected from the group consisting of hydrogen, $C_1$-$C_4$-alkyl, $C_1$-$C_4$-fluoroalkyl, $C_3$-$C_6$-cycloalkyl, and $C_3$-$C_6$-cycloalkyl-$C_1$-$C_4$-alkyl, where $R^{11}$ may also be selected from the group consisting of $C_1$-$C_4$-alkylsulfonyl and $C_1$-$C_4$-fluoroalkylsulfonyl;

$R^{13}$, $R^{14}$ independently of each other are selected from the group consisting of hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl, or $R^{13}$ and $R^{14}$ together with the N atom to which they are attached form a 3- to 7-membered, nitrogen heterocycle which may have 1, 2 or 3 further different or identical heteroatoms or heteroatom containing groups independently selected from the group consisting of O, N, S, SO and $SO_2$ as ring members and which may carry 1, 2, 3, 4, 5 or 6 $C_1$-$C_4$-alkyl substituents;

$R^{23}R^{24}$, $R^{33}$ and $R^{34}$ have one of the meanings given for $R^{13}$, $R^{14}$;

$R^{15}$, $R^{35}$ independently of each other are selected from the group consisting hydrogen, $C_1$-$C_4$-alkyl, $C_1$-$C_4$-fluoroalkyl, $C_3$-$C_6$-cycloalkyl and $C_3$-$C_6$-cycloalkyl-$C_1$-$C_4$-alkyl; and R' is hydrogen, $C_1$-$C_4$-alkyl, $C_1$-$C_4$-fluoroalkyl, $C_3$-$C_6$-cycloalkyl or $C_3$-$C_6$-cycloalkyl-$C_1$-$C_4$-alkyl;

an N-oxide thereof, a tautomer thereof, a hydrate thereof, or a pharmaceutically acceptable salt thereof.

2. The compound of claim 1, where A is $C(R^6,R^7)$.

3. The compound of claim 2, where A is $CH_2$.

4. The compound of claim 1, where X is C(O).

5. The compound of claim 4, where Y is C ($R^{y1}$,$R^{y2}$).

6. The compound of claim 4, where $R^{y1}$ and $R^{y2}$, independently of each other, are selected from the group consisting of hydrogen, fluorine and methyl.

7. The compound of claim 1, where Y is C(O).

8. The compound of claim 1, where Z is a bond.

9. The compound of claim 1, which is a compound of formula I.A.a

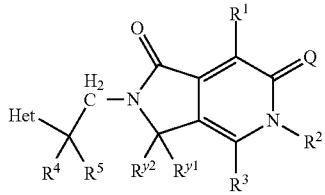

(I.A.a)

where Het, Q, $R^1$, $R^2$, $R^3$, $R^4$, $R^5$, $R^{y1}$ and $R^{y2}$ are as defined in claim 1, an N-oxide thereof, a tautomer thereof, a hydrate thereof, or a pharmaceutically acceptable salt thereof.

10. The compound of claim 1, where $R^1$ is selected from the group consisting of saturated 4-, 5-, 6-, 7- or 8-membered heteromonocycles and saturated 7-, 8-, 9- or 10-membered heterobicycles, where the heteromonocycles and the heterobicycles have one nitrogen or oxygen atom as ring member and may have one further heteroatom or heteroatom containing group as ring member, which is selected from the group consisting of O, S, S(=O), S(=O)$_2$ and N, where the saturated heteromonocycle and the saturated heterobicycle are unsubstituted or carry 1, 2, 3, 4 or 5 radicals $R^{C1}$ or one radical Y'—$R^{C2}$ and 0, 1, 2, 3 or 4 radicals $R^{C1}$, where $R^{C1}$, $R^{C2}$ and Y' are as defined in claim 1.

11. The compound of claim 10, where Z—$R^1$ is independently selected from the group consisting of 1-piperidinyl, 4,4-difluoro-1-piperidinyl, 4-hydroxylpiperidin-1-yl, 4-piperidinyl, 1-methyl-4-piperidinyl, 1-piperazinyl, 4-methyl-1-piperazinyl, 4-(tert.-butyloxycarbonyl)piperazin-1-yl, 1-piperazinylmethyl, 4-methyl-1-piperazinylmethyl, 1-piperazinylcarbonyl, 4-methyl-1-piperazinylcarbonyl, morpholin-4-yl, morpholin-4-ylmethyl, morpholin-4-ylcarbonyl, azepane-1-yl, 1,4-oxazepan-4-yl, thiomorpholin-4-yl, 1-oxothiomorpholin-4-yl, N-(oxetan-3-yl)amino, 1,1-dioxothiomorpholin-4-yl and oxetan-3-ylamino.

12. The compound of claim 1, where $R^1$ is independently selected from the group consisting of phenyl, 5- or 6 membered monocyclic hetaryl, and 9- or 10 membered bicyclic hetaryl, where hetaryl has one heteroatom, selected from the group consisting of O, S and N as ring member and optionally one or two further nitrogen atoms as ring members, where phenyl and the hetaryl radical are unsubstituted or either carry, independently of each other, 1, 2, 3, 4 or 5 radicals $R^{C3}$ or one radical Y'—$R^{C2}$ and 0, 1, 2, 3 or 4 radicals $R^{C3}$.

13. The compound of claim 12, where $R^1$ is independently selected from the group consisting of phenyl, 5- or 6-membered monocyclic hetaryl independently selected from the group consisting of pyridyl, pyrimidinyl, furyl, thienyl, pyrrolyl, imidazolyl, pyrazolyl, oxazolyl and thiazolyl, and 9- or 10-membered bicyclic hetaryl independently selected from the group consisting of indolyl, quinolinyl, isoquinolinyl, quinazolinyl, benzimidazolyl, 1,3-benzoxazolyl, 1,3-benzothiazolyl, benzotriazolyl, benzopyrazolyl, benzothienyl and benzofuryl, where phenyl and hetaryl are unsubstituted or carry 1, 2 or 3 radicals $R^{C3}$ which are independently selected from the group consisting of fluorine, chlorine, OH, CN, $C_1$-$C_4$-alkyl, $C_1$-$C_2$-fluoroalkyl, $C_1$-$C_4$-alkoxy, $C_1$-$C_2$-fluoroalkoxy, $C_1$-$C_4$-alkylsulfonylamino, $C_1$-$C_4$-alkylamino, di-$C_1$-$C_4$-alkylamino, $C_1$-$C_2$-alkoxy-$C_1$-$C_2$-alkyl, C(O)—O—$C_1$-$C_4$-alkyl, C(O)NH$_2$ and NH$_2$, or carry one radical Y'—$R^{C2}$, where Y' is a bond, CH$_2$ or C(O) and $R^{C2}$ is phenyl, pyridyl, pyrimidinyl, 1-imidzaolyl, 1-pyrazolyl, 1-piperidinyl, 1-piperazinyl, 4-methyl-1-piperazinyl or 4-morpholinyl, or, if $R^1$ is phenyl, two radicals $R^{C3}$ which are bound to adjacent carbon atoms, together with the phenyl ring to which they are bound, form a bicyclic heterocyclic radical, which is independently selected from the group consisting of 2,3-dihydrobenzofuran-5-yl, 2,3-dihydrobenzofuran-6-yl, 1,3-dihydroindol-2-on-5-yl, 1,3-dihydroindol-2-on-6-yl, benzo-1,3-dioxolan-5-yl, benzo-1,3-dioxolan-6-yl, benzo-1,4-dioxan-5-yl, benzo-1,4-dioxan-6-yl, benzo-1,5-dioxepan-6-yl and benzo-1,4-dioxepan-7-yl.

14. The compound of claim 1, where Z—$R^1$ is 4-pyridyl, 4-morpholinyl or 4-fluorophenyl.

15. The compound of claim 1, where $R^2$ is independently selected from the group consisting of hydrogen, $C_1$-$C_6$-alkyl, $C_1$-$C_4$-alkyl-OR$^{21}$, $C_1$-$C_4$-alkyl-NR$^{23}$R$^{24}$, $C_1$-$C_6$-fluoroalkyl, $C_3$-$C_6$-cycloalkyl-$C_1$-$C_4$-alkyl, where the cycloalkyl moiety is unsubstituted, partially or completely fluorinated, or substituted by 1, 2 or 3 methyl groups and phenyl-$C_1$-$C_4$-alkyl, wherein phenyl in the last mentioned radical is unsubstituted or carries 1 or 2 radicals independently selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl, $C_1$-$C_4$-fluoroalkoxy, $C_2$-$C_6$-alkenyl, C(O)R$^h$, benzyl, Z'—C(O)OR$^b$, Z'—C(O)NR$^c$R$^d$, S(O)$_2$NR$^d$ and Z'—NR$^e$R$^f$.

16. The compound of claim 15, where $R^2$ is independently selected from the group consisting of hydrogen, $C_1$-$C_6$-alkyl, $C_1$-$C_4$-alkoxy-$C_1$-$C_4$-alkyl, $C_1$-$C_6$-fluoroalkyl, $C_3$-$C_6$-cycloalkyl-$C_1$-$C_4$-alkyl, and phenyl-$C_1$-$C_4$-alkyl, wherein phenyl in the last mentioned radical is unsubstituted or carries 1 or 2 radicals independently selected from the group consisting of halogen, OH, CN, $C_1$-$C_4$-alkyl, $C_1$-$C_4$-alkoxy, hydroxy-$C_1$-$C_4$-alkyl, $C_1$-$C_4$-alkoxy-$C_1$-$C_4$-alkyl, cyano-$C_1$-$C_4$-alkyl, $C_1$-$C_4$-fluoroalkyl and $C_1$-$C_4$-fluoroalkoxy.

17. The compound of claim 1, where $R^3$ is independently selected from the group consisting of hydrogen, fluorine, $C_1$-$C_4$-alkyl, $C_1$-$C_2$-fluoroalkyl, $C_1$-$C_4$-alkoxy, $C_1$-$C_2$-fluoroalkoxy, cyclopropyl, optionally substituted by 1, 2 or 3 methyl groups, and fluorinated cyclopropyl.

18. The compound of claim 17, where $R^3$ is hydrogen.

19. The compound of claim 1, where $R^4$ and $R^5$, independently of each other, are independently selected from the group consisting of hydrogen, fluorine and methyl.

20. The compound of claim 1, where Het is independently selected from the group consisting of C-bound 5- or 6-membered monocyclic hetaryl, which has 1 or 2 nitrogen atoms as ring members, benzofuryl and C-bound, 9- or 10-membered fused bicyclic hetaryl, which has 1 or 2 nitrogen atoms as ring members and optionally a further heteroatom independently selected from the group consisting of O, S and N as ring member;

where monocyclic hetaryl, benzofuryl and bicyclic hetaryl may be unsubstituted or may carry 1, 2, 3 or 4 substituents Ra.

21. The compound of claim 20, where Het has at least one imino-nitrogen as a ring member, which is located in the position adjacent to the carbon atom which is bound to the moiety $C(R^4R^5)$.

22. The compound of claim 21, where Het is independently selected from the group consisting of 2-pyridyl, 2-pyrimidinyl, 4-pyrimidinyl, 2-pyrazinyl, 3-pyridazinyl, 2-imidazolyl, 4-imidazolyl, 3-pyrazolyl, 2-thiazolyl, 4-thiazolyl, 2-quinolinyl, 3-isoquinolinyl, 2-quinazolinyl, 2-quinoxalinyl, 1,5-naphthyridin-2-yl, 1,8-naphthyridin-2-yl, benzothiazol-2-yl, benzoxazol-2-yl, benzimidazol-2-yl, 1-methylbenzimidazol-2-yl, imidazo[1,2-a]pyridine-2-yl, pyrrolo[2,3-b]pyridine-6-yl, thieno[3,2-b]pyridine-5-yl, imidazo-[2,1-b]-thiazol-6-yl and 1,2,4-triazolo[1,5-a]pyridine-2-yl, where the aforementioned radicals may carry 1, 2 or 3 radicals independently selected from the group consisting of fluorine, chlorine, methyl, fluoromethyl, difluoromethyl, trifluoromethyl, methoxy, fluoromethoxy, difluoromethoxy, trifluoromethoxy, cyclopropyl optionally substituted by 1, 2 or 3 methyl groups, and fluorinated cyclopropyl.

23. The compound of claim 1, where Q is O.

24. The compound of claim 1, where $R^{x1}$, $R^{x2}$, $R^{y1}$ and $R^{y2}$, independently of each other are selected from the group consisting of hydrogen and fluorine.

25. The compound of claim 1, which is independently selected from the group consisting of 5-Methyl-7-morpholin-4-yl-2-(2-quinolin-2-yl-ethyl)-5H-pyrrolo[3,4-c]pyridine-1,3,6-trione;
5-Methyl-7-(4-methyl-piperazin-1-yl)-2-(2-quinolin-2-yl-ethyl)-5H-pyrrolo[3,4-c]pyridine-1,3,6-trione;
5-Methyl-7-(1,1-dioxo-thiomorpholin-4-yl)-2-(2-quinolin-2-yl-ethyl)-5H-pyrrolo[3,4-c]pyridine-1,3,6-trione;
5-Methyl-7-(4-pyridyl)-2-(2-quinolin-2-yl-ethyl)-5H-pyrrolo[3,4-c]pyridine-1,3,6-trione;
5-Methyl-7-morpholin-4-yl-2-(2-[1,2,4]triazolo[1,5-a]pyridin-2-yl-ethyl)-5H-pyrrolo[3,4-c]pyridine-1,3,6-trione;
5-Methyl-7-morpholin-4-yl-2-(2-quinolin-2-yl-ethyl)-1,2-dihydro-5H-pyrrolo[3,4-c]pyridine-3,6-dione;
5-Methyl-7-(4-methyl-piperazin-1-yl)-2-(2-quinolin-2-yl-ethyl)-1,2-dihydro-5H-pyrrolo[3,4-c]pyridine-3,6-dione;
5-Methyl-7-pyridin-4-yl-2-(2-quinolin-2-yl-ethyl)-1,2-dihydro-5H-pyrrolo[3,4-c]pyridine-3,6-dione;
5-Methyl-7-morpholin-4-yl-2-(2-quinolin-2-yl-ethyl)-3,5-dihydro-2H-pyrrolo[3,4-c]pyridine-1,6-dione;
5-Methyl-7-(4-methyl-piperazin-1-yl)-2-(2-quinolin-2-yl-ethyl)-3,5-dihydro-2H-pyrrolo[3,4-c]pyridine-1,6-dione;
5-Methyl-7-pyridin-4-yl-2-(2-quinolin-2-yl-ethyl)-3,5-dihydro-2H-pyrrolo[3,4-c]pyridine-1,6-dione;
5-Methyl-7-(1,1-dioxo-thiomorpholin-4-yl)-2-(2-quinolin-2-yl-ethyl)-3,5-dihydro-2H-pyrrolo[3,4-c]pyridine-1,6-dione;
5-Methyl-7-pyridin-3-yl-2-(2-quinolin-2-yl-ethyl)-3,5-dihydro-2H-pyrrolo[3,4-c]pyridine-1,6-dione;
5-(4-Methoxy-benzyl)-7-morpholin-4-yl-2-(2-quinolin-2-yl-ethyl)-3,5-dihydro-2H-pyrrolo[3,4-c]pyridine-1,6-dione;
7-Morpholin-4-yl-2-(2-quinolin-2-yl-ethyl)-3,5-dihydro-2H-pyrrolo[3,4-c]pyridine-1,6-dione;
5-Ethyl-7-morpholin-4-yl-2-(2-quinolin-2-yl-ethyl)-3,5-dihydro-2H-pyrrolo[3,4-c]pyridine-1,6-dione;
5-Isopropyl-7-morpholin-4-yl-2-(2-quinolin-2-yl-ethyl)-3,5-dihydro-2H-pyrrolo[3,4-c]pyridine-1,6-dione;
5-(2-Methoxy-ethyl)-7-morpholin-4-yl-2-(2-quinolin-2-yl-ethyl)-3,5-dihydro-2H-pyrrolo[3,4-c]pyridine-1,6-dione;
5-(2-Hydroxy-ethyl)-7-morpholin-4-yl-2-(2-quinolin-2-yl-ethyl)-3,5-dihydro-2H-pyrrolo[3,4-c]pyridine-1,6-dione;
5-Methyl-2-[2-(1-methyl-1H-benzoimidazol-2-yl)-ethyl]-7-morpholin-4-yl-3,5-dihydro-2H-pyrrolo[3,4-c]pyridine-1,6-dione;
5-Methyl-2-[2-(1-methyl-1H-benzoimidazol-2-yl)-ethyl]-7-pyridin-3-yl-3,5-dihydro-2H-pyrrolo[3,4-c]pyridine-1,6-dione;
2-(2-Imidazo[1,2-a]pyridin-2-yl-ethyl)-5-methyl-7-morpholin-4-yl-3,5-dihydro-2H-pyrrolo[3,4-c]pyridine-1,6-dione;
2-(2-Imidazo[1,2-a]pyridin-2-yl-ethyl)-5-methyl-7-morpholin-4-yl-3,5-dihydro-2H-pyrrolo[3,4-c]pyridine-1,6-dione;
5-Methyl-7-morpholin-4-yl-2-(2-[1,2,4]triazolo[1,5-a]pyridin-2-yl-ethyl)-3,5-dihydro-2H-pyrrolo[3,4-c]pyridine-1,6-dione;
5-Methyl-7-morpholin-4-yl-2-[2-(5,6,7,8-tetrahydro-[1,2,4]triazolo[1,5-a]pyridin-2-yl)-ethyl]-3,5-dihydro-2H-pyrrolo[3,4-c]pyridine-1,6-dione;
5-Methyl-7-pyridin-3-yl-2-(2-[1,2,4]triazolo[1,5-a]pyridin-2-yl-ethyl)-3,5-dihydro-2H-pyrrolo[3,4-c]pyridine-1,6-dione;
7-(4-Fluoro-phenyl)-5-methyl-2-(2-quinolin-2-yl-ethyl)-3,5-dihydro-2H-pyrrolo[3,4-c]pyridine-1,6-dione;
5-Methyl-7-pyrimidin-5-yl-2-(2-quinolin-2-yl-ethyl)-3,5-dihydro-2H-pyrrolo[3,4-c]pyridine-1,6-dione;
5-Methyl-7-(1H-pyrazol-4-yl)-2-(2-quinolin-2-yl-ethyl)-3,5-dihydro-2H-pyrrolo[3,4-c]pyridine-1,6-dione;
5-Methyl-7-(2-methyl-2H-pyrazol-3-yl)-2-(2-quinolin-2-yl-ethyl)-3,5-dihydro-2H-pyrrolo[3,4-c]pyridine-1,6-dione;
7-(4-Methoxy-phenyl)-5-methyl-2-(2-quinolin-2-yl-ethyl)-3,5-dihydro-2H-pyrrolo[3,4-c]pyridine-1,6-dione;
2-[2-(1,3-benzothiazol-2-yl)ethyl]-5-methyl-7-(4-pyridyl)-3,5-dihydro-2H-pyrrolo[3,4-c]pyridine-1,6-dione;
2-[2-(1,3-benzothiazol-2-yl)ethyl]-5-methyl-7-morpholin-4-yl-3,5-dihydro-2H-pyrrolo[3,4-c]pyridine-1,6-dione;
2-(2,2-Difluoro-2-quinolin-2-yl-ethyl)-5-methyl-7-morpholin-4-yl-3,5-dihydro-2H-pyrrolo[3,4-c]pyridine-1,6-dione; and
3,3-Difluoro-5-methyl-7-morpholin-4-yl-2-(2-quinolin-2-yl-ethyl)-3,5-dihydro-2H-pyrrolo[3,4-c]pyridine-1,6-dione;

an N-oxide thereof, a tautomer thereof, a hydrate thereof, or a pharmaceutically acceptable salt thereof.

26. A pharmaceutical composition which comprises at least one compound as claimed in claim 1 and at least one excipient.

* * * * *